United States Patent
Wang et al.

(10) Patent No.: US 9,963,480 B2
(45) Date of Patent: May 8, 2018

(54) NUCLEOSIDE PHOSPHORAMIDATE COMPOUND AND USE THEREOF

(71) Applicant: NANJING SANHOME PHARMACEUTICAL CO., LTD., Nanjing, Jiangsu (CN)

(72) Inventors: Yong Wang, Nanjing (CN); Liwen Zhao, Nanjing (CN); Xian Zhang, Nanjing (CN); Sheng Bi, Nanjing (CN); Yiping Gao, Nanjing (CN); Hongyan Chen, Nanjing (CN); Dezhong Wang, Nanjing (CN); Yang Nan, Nanjing (CN); Cang Zhang, Nanjing (CN); Yuxiu Li, Nanjing (CN); Di Zhang, Nanjing (CN)

(73) Assignee: NANJING SANHOME PHARMACEUTICAL CO., LTD., Jiangsu (CN)

( * ) Notice: Subject to any disclaimer, the term of this patent is extended or adjusted under 35 U.S.C. 154(b) by 174 days.

(21) Appl. No.: 14/764,865

(22) PCT Filed: Mar. 6, 2014

(86) PCT No.: PCT/CN2014/073004
§ 371 (c)(1),
(2) Date: Jul. 30, 2015

(87) PCT Pub. No.: WO2014/135107
PCT Pub. Date: Sep. 12, 2014

(65) Prior Publication Data
US 2015/0361123 A1 Dec. 17, 2015

(30) Foreign Application Priority Data

Mar. 8, 2013 (CN) .......................... 2013 1 0075423

(51) Int. Cl.
| | | |
|---|---|---|
| A01N 43/04 | (2006.01) | |
| A61K 31/70 | (2006.01) | |
| C07H 19/10 | (2006.01) | |
| C07H 19/048 | (2006.01) | |

(52) U.S. Cl.
CPC .................... C07H 19/10 (2013.01)

(58) Field of Classification Search
CPC .................................................. C07H 19/10
See application file for complete search history.

(56) References Cited

U.S. PATENT DOCUMENTS

| 7,405,204 B2 * | 7/2008 | Roberts | .............. | A61K 31/7076 |
| | | | | 514/42 |
| 8,871,737 B2 * | 10/2014 | Smith | .................... | C07H 19/06 |
| | | | | 514/47 |
| 9,108,999 B2 * | 8/2015 | Zhang | .................... | C07H 19/06 |
| 2006/0241064 A1 | 10/2006 | Roberts et al. | | |
| 2015/0361123 A1 | 12/2015 | Wang et al. | | |

FOREIGN PATENT DOCUMENTS

| AU | 2014225052 B2 | 11/2016 |
| CA | 2 810 928 A1 | 3/2012 |
| CN | 102695513 A | 9/2012 |
| WO | 2006/065335 A2 | 6/2006 |
| WO | 2008/121634 A2 | 10/2008 |
| WO | 2010/066699 A1 | 6/2010 |
| WO | 2010/075549 A2 | 7/2010 |
| WO | 2010/130726 A1 | 11/2010 |
| WO | 2015/101183 A1 | 7/2015 |

OTHER PUBLICATIONS

Jun. 16, 2014 Search Report issued in International Application No. PCT/CN2014/073004.
Nov. 11, 2015 Office Action issued in Australian Patent Application No. 2014225052.
Sep. 12, 2016 Office Action issued in Australian Patent Application No. 2014225052.
Aug. 1, 2016 Extended Search Report issued in European Patent Application No. 14760567.9.
Jul. 14, 2016 Office Action issued in Canadian Patent Application No. 2,899,763.
Oct. 4, 2016 Office Action issued in Japanese Patent Application No. 2015-560536.
Mar. 23, 2017 Office Action issued in U.S. Appl. No. 14/764,865.
Mar. 23, 2017 Office Action issued in U.S. Appl. No. 14/781,707.

* cited by examiner

*Primary Examiner* — Lawrence E Crane
(74) *Attorney, Agent, or Firm* — Oliff PLC

(57) ABSTRACT

A novel nucleoside phosphoramidate compound of the formula below, or a stereoisomer, salt, hydrate, solvate or crystal thereof for the treatment of Flaviviridae family viral infection, especially hepatitis C viral infection, and having a good anti-HCV effect; a pharmaceutical composition having the compound, or a stereoisomer, salt, hydrate, solvate or crystal thereof:

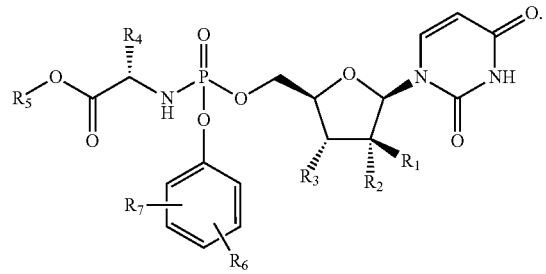

18 Claims, No Drawings

NUCLEOSIDE PHOSPHORAMIDATE COMPOUND AND USE THEREOF

CROSS-REFERENCE TO RELATED APPLICATIONS

This application is the 35 U.S.C. § 371 National Phase Application of International Application Serial No. PCT/CN2014/073004, filed on Mar. 6, 2014, which in turn claims priority to Chinese Patent Application No. CN 201310075423.5, filed on Mar. 8, 2013, which is hereby incorporated by reference in its entirety.

TECHNICAL FIELD

The present invention belongs to the field of pharmaceutical chemistry, and in particular relates to a series of new nucleoside phosphoramidate compounds, compositions containing the nucleoside phosphoramidate compounds, and use of said compounds or compositions as the medicament for treatment of viral infection diseases, especially as the medicament for treatment of viral hepatitis.

BACKGROUND

Hepatitis C virus (HCV) infection is a worldwide epidemic disease, and there are more than 200 million chronic infected individuals globally. Chronic infection rate of HCV is 15% in Egypt, 4.8% in Pakistan, and 3.2% in China, and these countries rank the world top three. Clinical manifestations of hepatitis C viral infection are diverse, ranging from mild symptoms such as inflammation to serious illnesses such as liver cirrhosis or liver cancer. Chronic hepatitis C can also be complicated by some extrahepatic manifestations, including rheumatoid arthritis, keratoconjunctivitis sicca, lichen planus, glomerulonephritis, mixed cryoglobulinemia, B-cell lymphoma and porphyria cutanea tarda, etc., which may be caused by the body's abnormal immune response. Furthermore, various complications can occur during the stage of HCV-induced cirrhosis decompensation, such as ascites, abdominal infections, upper gastrointestinal bleeding, hepatic encephalopathy, hepatorenal syndrome, liver failure and other symptoms.

HCV belongs to the Flaviviridae family *hepatovirus* genus, and its genetic structure is similar to the other two genera in Flaviviridae family, i.e. *pestivirus* genus and *flavivirus* genus. Currently, the standard methods of treatment of HCV infection include interferon alone, and combination therapy of interferon and ribavirin. However, only 50% patients respond to these methods, and interferon has significant side effects, such as flu-like symptoms, weight reduction, fatigue and weakness, and combination therapy of interferon and ribavirin has considerable side effects, including hemolysis, anemia and fatigue, etc.

In addition, drugs developed for the treatment of HCV infection include protease inhibitors, thiazolidine derivatives, thiazolidines and N-benzanilides, phenan-threnequinone, helicase inhibitors, nucleoside polymerase inhibitors and gliotoxin, antisense phosphorothioate oligodeoxynucleotides, inhibitors of IRES-dependent translation, ribozymes and nucleoside analogs, etc.

Currently, using nucleoside phosphate compounds for the treatment of infection with the virus from the Flaviviridae family, particularly for the treatment of HCV infection is an important research direction in this field. WO 2006/065335 disclosed a fluorinated pyrrolo[2,3,d]pyrimidine nucleoside compound for inhibiting HCV virus. US 2006/0241064 disclosed a nucleoside compound for treating viral infection caused by the virus from the Flaviviridae family, such as HCV. WO 2008/121634 disclosed a nucleoside phosphoramidate compound for treating viral infections of mammals.

Notwithstanding the above disclosure, there is still a great need for compounds effective for the treatment and/or prevention of HCV infection.

SUMMARY OF THE INVENTION

An objective of the present invention is to provide a novel nucleoside phosphoramidate compound of general formula I for the treatment and/or prevention of HCV infection:

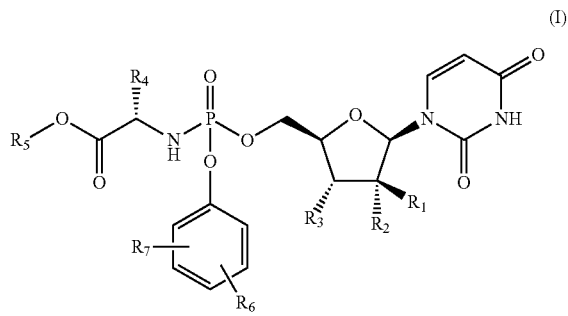

or a stereoisomer, salt, hydrate, solvate or crystal thereof, wherein
(1) $R_1$ is selected from $C_{1-6}$ alkyl;
(2) $R_2$ is selected from halogen;
(3) $R_3$ is selected from OH, H, and $C_{1-4}$ alkoxy;
(4) $R_4$ is selected from H, $C_{1-6}$ alkyl, and halogenated $C_{1-6}$ alkyl;
(5) $R_5$ is selected from $C_{1-6}$ alkyl, and halogenated $C_{1-6}$ alkyl;
(6) $R_6$ is selected from the following moieties:
  a) phenyl-Y—, wherein Y is absent or selected from $C_{1-6}$ alkyl, $C_{2-6}$ alkenyl, $C_{2-6}$ alkynyl, $C_{2-6}$ alkenyl-(CO)—, $C_{2-6}$ alkynyl-(CO)—, O, S, amino and —N($C_{1-6}$ alkyl), and wherein the phenyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO, or the phenyl and a five- or six-membered ring taken together form a benzo five-membered ring or benzo six-membered ring;
  b) heterocyclyl-Y—, wherein Y is absent or selected from $C_{1-6}$ alkyl, $C_{2-6}$ alkenyl, $C_{2-6}$ alkynyl, $C_{2-6}$ alkenyl-(CO)—, $C_{2-6}$ alkynyl-(CO)—, O, S, amino and —N($C_{1-6}$ alkyl), or the heterocyclyl together with Y to which it is attached form a bicyclic heterocycle, and wherein the heterocyclyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO;
  c) $C_{1-6}$ alkyl-O—C(O)—$C_{2-6}$ alkenyl- and $C_{1-6}$ alkyl-O—C(O)—$C_{2-6}$ alkenyl-C(O)—, wherein the $C_{1-6}$ alkyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO; and (7) $R_7$ is selected from H, halogen, $C_{1-6}$ alkyl, halogenated $C_{1-6}$ alkyl, $C_{1-6}$ alkoxy, halogenated $C_{1-6}$ alkoxy, $NO_2$, CN, $C_{1-6}$ alkyl-NH—CO—, hydroxy, mono-$C_{1-6}$ alkylamino, di-$C_{1-6}$ alkylamino, $C_{1-6}$ alkyl-S—, $C_{2-6}$ alkenyl-S—, $C_{2-6}$ alkynyl-S—, $C_{1-6}$ alkyl-SO—, $C_{2-6}$ alkenyl-SO—, $C_{2-6}$ alkynyl-SO—, $C_{1-6}$ alkyl-$SO_2$—, $C_{2-6}$ alkenyl-$SO_2$—, $C_{2-6}$ alkynyl-$SO_2$—, $C_{1-6}$ alkyl-$OSO_2$—, $C_{2-6}$ alkenyl-$OSO_2$—, $C_{2-6}$ alkynyl-$OSO_2$—; or (8) $R_6$ and $R_7$ together with the benzene ring to which they are attached form a benzo five-membered ring or benzo six-membered ring, wherein the benzo five-membered ring or benzo six-membered ring is optionally substituted by one or more groups selected from halogen, $C_{1-6}$ alkyl, $C_{1-6}$ alkoxy, halogenated $C_{1-6}$ alkyl, halogenated $C_{1-6}$ alkoxy, phenyl, cyano, $C_{1-6}$ alkyl-OC(O)— and $C_{1-6}$ alkyl-OC(O)—$CH_2$—.

Another objective of the present invention is to provide a preparation method of the nucleoside phosphoramidate compound of general formula I or a stereoisomer, salt, hydrate, solvate or crystal thereof.

Still another objective of the present invention is to provide a composition comprising a nucleoside phosphoramidate compound of general formula I of the present invention or a stereoisomer, salt, hydrate, solvate or crystal thereof and a pharmaceutically acceptable carrier, and a composition comprising a nucleoside phosphoramidate compound of general formula I of the present invention or a stereoisomer, salt, hydrate, solvate or crystal thereof and another antiviral drug.

Still another objective of the present invention is to provide a method for treatment and/or prevention of hepatitis C viral infection using a nucleoside phosphoramidate compound of general formula I of the present invention or a stereoisomer, salt, hydrate, solvate or crystal thereof, as well as use of a nucleoside phosphoramidate compound of general formula I of the present invention or a stereoisomer, salt, hydrate, solvate or crystal thereof in the manufacture of a medicament for treatment and/or prevention of hepatitis C viral infection.

For the above objectives, the present invention provides the following technical solutions:

In a first aspect, the present invention provides a novel nucleoside phosphoramidate compound of general formula I:

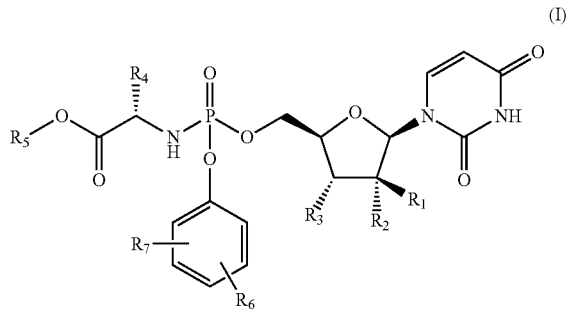

(I)

or a stereoisomer, salt, hydrate, solvate or crystal thereof, wherein (1) $R_1$ is selected from $C_{1-6}$ alkyl; preferably, $R_1$ is selected from $C_{1-3}$ alkyl; more preferably, $R_1$ is $CH_3$;

(2) $R_2$ is selected from halogen; preferably, $R_2$ is F;

(3) $R_3$ is selected from OH, H, $C_{1-4}$ alkoxy; preferably, $R_3$ is selected from OH, H, methoxy; more preferably, $R_3$ is OH;

(4) $R_4$ is selected from H, $C_{1-6}$ alkyl, halogenated $C_{1-6}$ alkyl; preferably, $R_4$ is selected from H, $C_{1-6}$ alkyl; more preferably, $R_4$ is selected from H and $C_{1-4}$ alkyl;

(5) $R_5$ is selected from $C_{1-6}$ alkyl, halogenated $C_{1-6}$ alkyl; preferably, $R_5$ is selected from $C_{1-6}$ alkyl; more preferably, $R_5$ is selected from $C_{1-4}$ alkyl;

(6) $R_6$ is selected from:

a) phenyl-Y—, wherein Y is absent or selected from $C_{1-6}$ alkyl, $C_{2-6}$ alkenyl, $C_{2-6}$ alkynyl, $C_{2-6}$ alkenyl-(CO)—, $C_{2-6}$ alkynyl-(CO)—, O, S, amino and —N($C_{1-6}$ alkyl), and wherein the phenyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO, or the phenyl and a five- or six-membered ring taken together form a benzo five-membered ring or benzo six-membered ring;

b) heterocyclyl-Y—, wherein Y is absent or selected from $C_{1-6}$ alkyl, $C_{2-6}$ alkenyl, $C_{2-6}$ alkynyl, $C_{2-6}$ alkenyl-(CO)—, $C_{2-6}$ alkynyl-(CO)—, O, S, amino and —N($C_{1-6}$ alkyl), or the heterocyclyl together with Y to which it is attached form a bicyclic heterocycle, and wherein the heterocyclyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO;

c) $C_{1-6}$ alkyl-O—C(O)—$C_{2-6}$ alkenyl- and $C_{1-6}$ alkyl-O—C(O)—$C_{2-6}$ alkenyl-C(O)—, wherein the $C_{1-6}$ alkyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO;

preferably, $R_6$ is selected from:

a) phenyl-Y—, wherein Y is absent or selected from $C_{1-4}$ alkyl, $C_{2-4}$ alkenyl, $C_{2-4}$ alkynyl, $C_{2-4}$ alkenyl-(CO)—, $C_{2-4}$ alkynyl-(CO)—, O, S, amino and —N($C_{1-4}$ alkyl), and wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO, or the phenyl and a five- or six-membered ring taken together form a benzo five-membered ring or benzo six-membered ring;

b) heterocyclyl-Y—, wherein Y is absent or selected from $C_{1-4}$ alkyl, $C_{2-4}$ alkenyl, $C_{2-4}$ alkynyl, $C_{2-4}$ alkenyl-(CO)—, $C_{2-4}$ alkynyl-(CO)—, O, S, amino and —N($C_{1-4}$ alkyl), or the heterocyclyl together with Y to which it is attached form a bicyclic heterocycle, and wherein the heterocyclyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO;

c) $C_{1-4}$ alkyl-O—C(O)—$C_{2-4}$ alkenyl- and $C_{1-4}$ alkyl-O—C(O)—$C_{2-4}$ alkenyl-C(O)—, wherein the $C_{1-4}$ alkyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO;

more preferably, $R_6$ is selected from:

a) phenyl, phenyl-$C_{1-3}$ alkyl-, phenyl-$C_{2-3}$ alkenyl-, phenyl-$C_{2-3}$ alkynyl-, phenyl-O—, phenyl-S—, phenyl-NH—, phenyl-N($C_{1-3}$ alkyl)-, phenyl-ethenyl-(CO)— and naphthyl-ethenyl-(CO)—, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;

b) 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, thieno[3,2-b]thienyl-Y—, wherein Y is absent or selected from methyl, ethyl, ethenyl, ethynyl, ethenyl-(CO)—, ethynyl-(CO)—, O, S, amino and —NCH$_2$—, and wherein each of the heterocyclyl groups is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO;

c) methyl-OC(O)—=—, ethyl-OC(O)—=—, propyl-OC(O)—=—, isopropyl-OC(O)—=—, butyl-OC(O)—=—, isobutyl-OC(O)—=— and t-butyl-OC(O)—=—.

Still more preferably, $R_6$ is selected from:

a) phenyl, benzoxazolyl, benzo[b]pyrazinyl, benzo[b]pyrrolyl, phenyl-(CH$_2$)—, phenyl-=-, phenyl-=-C(O)— and phenyl-≡-, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO;

b) 1H-imidazolyl, 1,2,4-triazolyl, 1,2,3-triazolyl, thiazolyl, 1,2,3-thiadiazolyl, 1,2,4-thiadiazolyl, 1,3,4-thiadiazolyl, oxazolyl, 1,2,4-oxadiazolyl, 1,2,3-oxadiazolyl, 1,3,4-oxadiazolyl, pyrimidinyl, pyrazinyl, pyridazinyl, quinoxalinyl, 4H-chromen-4-one, pyridyl, thieno[3,2-b]thienyl, 1H-imidazolyl-(CH$_2$)—, 1,2,4-triazolyl-(CH$_2$)—, 1,2,3-triazolyl-(CH$_2$)—, thiazolyl-(CH$_2$)—, 1,2,3-thiadiazolyl-(CH$_2$)—, 1,2,4-thiadiazolyl-(CH$_2$)—, 1,3,4-thiadiazolyl-(CH$_2$)—, oxazolyl-(CH$_2$)—, 1,2,4-oxadiazolyl-(CH$_2$)—, 1,2,3-oxadiazolyl-(CH$_2$)—, 1,3,4-oxadiazolyl-(CH$_2$)—, pyrimidinyl-(CH$_2$)—, pyrazinyl-(CH$_2$)—, pyridazinyl-(CH$_2$)—, quinoxalinyl-(CH$_2$)—, 4H-chromen-4-one-(CH$_2$)—, pyridyl-(CH$_2$)—, thieno[3,2-b]thienyl-(CH$_2$)—, 1H-imidazolyl-=-, 1,2,4-triazolyl-=-, 1,2,3-triazolyl-=-, thiazolyl-=-, 1,2,3-thiadiazolyl-=-, 1,2,4-thiadiazolyl-=-, 1,3,4-thiadiazolyl-=-, oxazolyl-=-, 1,2,4-oxadiazolyl-=-, 1,2,3-oxadiazolyl-=-, 1,3,4-oxadiazolyl-=-, pyrimidinyl-=-, pyrazinyl-=-, pyridazinyl-=-, quinoxalinyl-=-, 4H-chromen-4-one-=-, pyridyl-=-, thieno[3,2-b]thienyl-=-, 1H-imidazolyl-≡-, 1,2,4-triazolyl-≡-, 1,2,3-triazolyl-≡-, thiazolyl-≡-, 1,2,3-thiadiazolyl-≡-, 1,2,4-thiadiazolyl-≡-, 1,3,4-thiadiazolyl-≡-, oxazolyl-≡-, 1,2,4-oxadiazolyl-≡-, 1,2,3-oxadiazolyl-≡-, 1,3,4-oxadiazolyl-≡-, pyrimidinyl-≡-, pyrazinyl-≡-, pyridazinyl-≡-, quinoxalinyl-≡-, 4H-chromen-4-one-≡-, pyridyl-≡- and thieno[3,2-b]thienyl-≡-, wherein each of heterocyclyl groups is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$acylamino, halogenated $C_{1-4}$ alkyl, halogenated $C_{1-4}$ alkoxy, amino, $N(C_{1-4}$ alkyl$)_2$ and $C_{1-4}$ alkyl NHCO;

c) methyl-OC(O)—=—; and (7) $R_7$ is selected from H, halogen, $C_{1-6}$ alkyl, halogenated $C_{1-6}$ alkyl, $C_{1-6}$ alkoxy, halogenated $C_{1-6}$ alkoxy, NO$_2$, CN, $C_{1-6}$ alkyl-NH—CO—, hydroxy, mono-$C_{1-6}$ alkylamino, di-$C_{1-6}$ alkylamino, $C_{1-6}$ alkyl-S—, $C_{2-6}$ alkenyl-S—, $C_{2-6}$ alkynyl-S—, $C_{1-6}$ alkyl-SO—, $C_{2-6}$ alkenyl-SO—, $C_{2-6}$ alkynyl-SO—, $C_{1-6}$ alkyl-SO$_2$—, $C_{2-6}$ alkenyl-SO$_2$—, $C_{2-6}$ alkynyl-SO$_2$—, $C_{1-6}$ alkyl-OSO$_2$—, $C_{2-6}$ alkenyl-OSO$_2$—, $C_{2-6}$ alkynyl-OSO$_2$—; preferably, $R_7$ is selected from H, halogen, $C_{1-6}$ alkyl, halogenated $C_{1-6}$ alkyl, $C_{1-6}$ alkoxy, halogenated $C_{1-6}$ alkoxy, NO$_2$, CN, $C_{1-6}$ alkyl-NH—CO—; more preferably, $R_7$ is selected from H, halogen, $C_{1-4}$ alkyl, halogenated $C_{1-4}$ alkyl, $C_{1-4}$ alkoxy, halogenated $C_{1-4}$ alkoxy, NO$_2$, CN, $C_{1-4}$ alkyl-NH—CO—; or (8) $R_6$ and $R_7$ together with the benzene ring to which they are attached form a benzo five-membered ring or benzo six-membered ring, wherein the benzo five-membered ring or benzo six-membered ring is optionally substituted by one or more groups selected from halogen, $C_{1-6}$ alkyl, $C_{1-6}$ alkoxy, halogenated $C_{1-6}$ alkyl, halogenated $C_{1-6}$ alkoxy, phenyl, cyano, $C_{1-6}$ alkyl-OC(O)—, $C_{1-6}$ alkyl-OC(O)—CH$_2$—; preferably, $R_6$ and $R_7$ together with the benzene ring to which they are attached form a 1,2,3,4-tetrahydronaphthalene, 2,3-dihydro-1H-indene, indole, benzofuran, quinoxaline, 4H-chromen-4-one, benzo[d]isoxazole, benzo[d]oxazole, benzo[c][1,2,5]thiadiazole, benzo[b]thiophene, benzodihydropyran-4-one, wherein each of these fused rings is optionally substituted by one or more groups selected from halogen, $C_{1-6}$ alkyl, $C_{1-6}$ alkoxy, halogenated $C_{1-6}$ alkyl, halogenated $C_{1-6}$ alkoxy, phenyl, cyano, $C_{1-6}$ alkyl-OC(O)— and $C_{1-6}$ alkyl-OC(O)—CH$_2$—.

In a preferred embodiment, the present invention provides a compound of general formula I or a stereoisomer, salt, hydrate, solvate or crystal thereof, wherein $R_1$ is methyl, ethyl, propyl or isopropyl; $R_2$ is F; $R_3$ is OH, H or methoxy; $R_4$ is H, methyl, ethyl, n-propyl or isopropyl; $R_5$ is methyl, ethyl, n-propyl, isopropyl, n-butyl, isobutyl or t-butyl; $R_6$ is phenyl-Y— or heterocyclyl-Y—, wherein Y is absent or selected from $C_{1-3}$ alkyl, $C_{2-3}$ alkenyl, $C_{2-3}$ alkynyl, $C_{2-3}$ alkenyl-(CO)—, $C_{2-3}$ alkynyl-(CO)—, O, S, amino and —N($C_{1-3}$ alkyl), and wherein the phenyl or the heterocyclyl is optionally substituted by one or more groups selected from $C_{1-3}$ alkyl, halogen, nitro, $C_{1-3}$ alkoxy, cyano, $C_{2-3}$ alkenyl, $C_{2-3}$ alkynyl, $C_{1-3}$ acylamino, halogenated $C_{1-3}$ alkyl, halogenated $C_{1-3}$ alkoxy, amino, $N(C_{1-3}$ alkyl$)_2$ and $C_{1-3}$ alkyl NHCO, or the phenyl and a five- or six-membered ring taken together form a benzo five-membered ring or benzo six-membered ring.

Surprisingly, the inventors of the present invention have found that, when $R_6$ group and the oxygen group both of which are attached to the benzene ring in general formula I are at the para- or meta-position to each other, especially where $R_6$ is selected from phenyl-Y— and heterocyclyl-Y—, the compound according to the present invention has a very excellent anti-HCV activity. Without wishing to be bound by any existing theory, the inventors of the present invention believe that, the compound of general formula I wherein $R_6$ group particularly selected from phenyl-Y—, and the phenyl-Y— or heterocyclyl-Y— is positioned either para or meta to the —O— group attached to the benzene ring in the structure of phenyl-Y-phenyl-O— or heterocyclyl-Y-phenyl-O—, exhibits excellent anti-HCV activity.

In a further preferred embodiment, the present invention provides a compound of general formula I or a stereoisomer, salt, hydrate, solvate or crystal thereof, wherein $R_1$ is methyl or ethyl; $R_2$ is F; $R_3$ is OH or H; $R_4$ is H, methyl or ethyl; $R_5$ is methyl, ethyl, n-propyl or isopropyl; $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, cyano, $C_{2-3}$ alkenyl, $C_{2-3}$ alkynyl, $C_{1-3}$ acylamino, halogenated $C_{1-3}$ alkyl, halogenated $C_{1-3}$ alkoxy, amino, $N(C_{1-3}$ alkyl$)_2$ and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group "phenyl-Y—" and the oxygen group both of which are attached to the benzene ring are at the para- or meta-position to each other.

In a further preferred embodiment, the present invention provides a compound of general formula I or a stereoisomer, salt, hydrate, solvate or crystal thereof, wherein $R_1$ is methyl; $R_2$ is F; $R_3$ is OH; $R_4$ is H, methyl or ethyl; $R_5$ is methyl, ethyl, n-propyl or isopropyl; $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, halogenated $C_{1-3}$ alkyl, halogenated $C_{1-3}$ alkoxy, cyano, $C_{2-3}$ alkenyl, $C_{2-3}$ alkynyl, $C_{1-3}$ acylamino, amino and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group "phenyl-Y—" and the oxygen group both of which are attached to the benzene ring are at the para- or meta-position to each other.

In a further preferred embodiment, the present invention provides a compound of general formula I or a stereoisomer, salt, hydrate, solvate or crystal thereof, wherein $R_1$ is methyl; $R_2$ is F; $R_3$ is OH; $R_4$ is H or methyl; $R_5$ is isopropyl; $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, halogenated $C_{1-3}$ alkyl, halogenated $C_{1-3}$ alkoxy, cyano and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group "phenyl-Y—" and the oxygen group both of which are attached to the benzene ring are at the para- or meta-position to each other.

In a further preferred embodiment, the present invention provides a compound of general formula I or a stereoisomer, salt, hydrate, solvate or crystal thereof, wherein $R_6$ is phenyl or benzyl, preferably, the phenyl or benzyl and the oxygen group both of which are attached to the benzene ring are at the para- or meta-position to each other.

In other embodiments, the present invention provides a compound of general formula I or a stereoisomer, salt, hydrate, solvate or crystal thereof, wherein $R_6$ is heterocyclyl-Y—, wherein the heterocyclyl can also be furyl, pyrrolyl, tetrazolyl, furazanyl, dioxadiazolyl, pyranyl, thiopyranyl, piperidinyl, triazinyl, oxazinyl, etc.

In some embodiments, more preferably, the present invention provides a compound of general formula Ia:

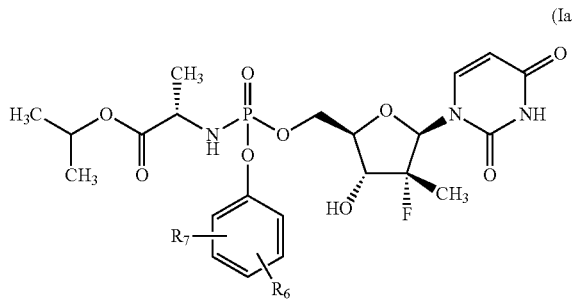

(Ia)

or a stereoisomer, salt, hydrate, solvate or crystal thereof, wherein (1) $R_6$ is selected from:
  a) phenyl-Y—, wherein Y is absent or selected from $C_{1-6}$ alkyl, $C_{2-6}$ alkenyl, $C_{2-6}$ alkynyl, $C_{2-6}$ alkynyl-(CO)—, $C_{2-6}$ alkynyl-(CO)—, O, S, amino and —N($C_{1-6}$ alkyl), and wherein the phenyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, $N(C_{1-6}$ alkyl$)_2$ and $C_{1-6}$ alkyl NHCO, or the phenyl and a five- or six-membered ring taken together form a benzo five-membered ring or benzo six-membered ring;
  b) heterocyclyl-Y—, wherein Y is absent or selected from $C_{1-6}$ alkyl, $C_{2-6}$ alkenyl, $C_{2-6}$ alkynyl, $C_{2-6}$ alkenyl-(CO)—, $C_{2-6}$ alkynyl-(CO)—, O, S, amino and —N($C_{1-6}$ alkyl), or the heterocyclyl together with Y to which it is attached form a bicyclic heterocycle, and wherein the heterocyclyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, $N(C_{1-6}$ alkyl$)_2$ and $C_{1-6}$ alkyl NHCO; and
  c) $C_{1-6}$ alkyl-O—C(O)—$C_{2-6}$ alkenyl- and $C_{1-6}$ alkyl-O—C(O)—$C_{2-6}$ alkenyl-C(O)—, wherein the $C_{1-6}$ alkyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, $N(C_{1-6}$ alkyl$)_2$ and $C_{1-6}$ alkyl NHCO;

preferably, $R_6$ is selected from:
  a) phenyl-Y—, wherein Y is absent or selected from $C_{1-4}$ alkyl, $C_{2-4}$ alkenyl, $C_{2-4}$ alkynyl, $C_{2-4}$ alkenyl-(CO)—, $C_{2-4}$ alkynyl-(CO)—, O, S, amino and —N($C_{1-4}$ alkyl), and wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO, or the phenyl and a five- or six-membered ring taken together form a benzo five-membered ring or benzo six-membered ring;
  b) heterocyclyl-Y—, wherein Y is absent or selected from $C_{1-4}$ alkyl, $C_{2-4}$ alkenyl, $C_{2-4}$ alkynyl, $C_{2-4}$ alkenyl-(CO)—, $C_{2-4}$ alkynyl-(CO)—, O, S, amino and —N($C_{1-4}$ alkyl), or the heterocyclyl together with Y to which it is attached form a bicyclic heterocycle, and wherein the heterocyclyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO; and
  c) $C_{1-4}$ alkyl-O—C(O)—$C_{2-4}$ alkenyl- and $C_{1-4}$ alkyl-O—C(O)—$C_{2-4}$ alkenyl-C(O)—, wherein the $C_{1-4}$ alkyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO;

more preferably, $R_6$ is selected from:
  a) phenyl, phenyl-$C_{1-3}$ alkyl-, phenyl-$C_{2-3}$ alkenyl-, phenyl-$C_{2-3}$ alkynyl-, phenyl-O—, phenyl-S—, phenyl-NH—, phenyl-N($C_{1-3}$ alkyl)-, phenyl-ethenyl-(CO)— and naphthyl-ethenyl-(CO)—, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;

b) 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, thieno[3,2-b]thienyl-Y—, wherein Y is absent or selected from —CH$_2$—, —CH$_2$—CH$_2$—, ethenyl, ethynyl, ethenyl-(CO)—, ethynyl-(CO)—, O, S, amino and —NCH$_2$—, wherein each of the heterocyclyl groups is optionally substituted by one or more groups selected from C$_{1-4}$ alkyl, halogen, nitro, C$_{1-4}$ alkoxy, cyano, C$_{2-4}$ alkenyl, C$_{2-4}$ alkynyl, C$_{1-4}$ acylamino, halogenated C$_{1-4}$ alkyl, halogenated C$_{1-4}$ alkoxy, amino, N(C$_{1-4}$ alkyl)$_2$ and C$_{1-4}$ alkyl NHCO; and c) methyl-OC(O)—=—, ethyl-OC(O)—=—, propyl-OC(O)—=—, isopropyl-OC(O)—=—, butyl-OC(O)—=—, isobutyl-OC(O)—=— and t-butyl-OC(O)—=—;

Still more preferably, R$_6$ is selected from:

a) phenyl, phenyl-(CH$_2$)—, phenyl-=—, phenyl-=-C(O)— and phenyl-≡-, wherein the phenyl is optionally substituted by one or more groups selected from C$_{1-4}$ alkyl, halogen, nitro, C$_{1-4}$ alkoxy, cyano, C$_{2-4}$ alkenyl, C$_{2-4}$ alkynyl, C$_{1-4}$ acylamino, halogenated C$_{1-4}$ alkyl, amino, N(C$_{1-4}$ alkyl)$_2$ and C$_{1-4}$ alkyl NHCO, or the phenyl and a group selected from oxazolyl, pyrazinyl and pyrrolyl taken together form a benzoxazolyl, benzo[b]pyrazinyl or benzo[b]pyrrolyl;

b) 1H-imidazolyl, 1,2,4-triazolyl, 1,2,3-triazolyl, thiazolyl, 1,2,3-thiadiazolyl, 1,2,4-thiadiazolyl, 1,3,4-thiadiazolyl, oxazolyl, 1,2,4-oxadiazolyl, 1,2,3-oxadiazolyl, 1,3,4-oxadiazolyl, pyrimidinyl, pyrazinyl, pyridazinyl, quinoxalinyl, 4H-chromen-4-one, thieno[3,2-b]thienyl, 1H-imidazolyl-(CH$_2$)—, 1,2,4-triazolyl-(CH$_2$)—, 1,2,3-triazolyl-(CH$_2$)—, thiazolyl-(CH$_2$)—, 1,2,3-thiadiazolyl-(CH$_2$)—, 1,2,4-thiadiazolyl-(CH$_2$)—, 1,3,4-thiadiazolyl-(CH$_2$)—, oxazolyl-(CH$_2$)—, 1,2,4-oxadiazolyl-(CH$_2$)—, 1,2,3-oxadiazolyl-(CH$_2$)—, 1,3,4-oxadiazolyl-(CH$_2$)—, pyrimidinyl-(CH$_2$)—, pyrazinyl-(CH$_2$)—, pyridazinyl-(CH$_2$)—, quinoxalinyl-(CH$_2$)—, 4H-chromen-4-one-(CH$_2$)—, pyridyl-(CH$_2$)—, thieno[3,2-b]thienyl-(CH$_2$)—, 1H-imidazolyl-=-, 1,2,4-triazolyl-=-, 1,2,3-triazolyl-=-, thiazolyl-=-, 1,2,3-thiadiazolyl-=-, 1,2,4-thiadiazolyl-=-, 1,3,4-thiadiazolyl-=-, oxazolyl-=-, 1,2,4-oxadiazolyl-=-, 1,2,3-oxadiazolyl-=-, 1,3,4-oxadiazolyl-=-, pyrimidinyl-=-, pyrazinyl-=-, pyridazinyl-=-, quinoxalinyl-=-, 4H-chromen-4-one-=-, pyridyl-=-, thieno[3,2-b]thienyl-=-, 1H-imidazolyl-≡-, 1,2,4-triazolyl-≡-, 1,2,3-triazolyl-≡-, thiazolyl-≡-, 1,2,3-thiadiazolyl-≡-, 1,2,4-thiadiazolyl-≡-, 1,3,4-thiadiazolyl-≡-, oxazolyl-≡-, 1,2,4-oxadiazolyl-≡-, 1,2,3-oxadiazolyl-≡-, 1,3,4-oxadiazolyl-≡-, pyrimidinyl-≡-, pyrazinyl-≡-, pyridazinyl-≡-, quinoxalinyl-≡-, 4H-chromen-4-one-≡-, pyridyl-≡- and thieno[3,2-b]thienyl-≡-, wherein each of the heterocyclyl groups is optionally substituted by one or more groups selected from C$_{1-4}$ alkyl, halogen, nitro, C$_{1-4}$ alkoxy, cyano, C$_{2-4}$ alkenyl, C$_{2-4}$ alkynyl, C$_{1-4}$ acylamino, halogenated C$_{1-4}$ alkyl, halogenated C$_{1-4}$ alkoxy, amino, N(C$_{1-4}$ alkyl)$_2$ and C$_{1-4}$ alkyl NHCO; and c) methyl-OC(O)—=—; and (2) R$_7$ is selected from H, halogen, C$_{1-6}$ alkyl, halogenated C$_{1-6}$ alkyl, C$_{1-6}$ alkoxy, halogenated C$_{1-6}$ alkoxy, NO$_2$, CN and C$_{1-6}$ alkyl-NH—CO—; preferably, R$_7$ is selected from H, halogen, C$_{1-4}$ alkyl, halogenated C$_{1-4}$ alkyl, C$_{1-4}$ alkoxy, halogenated C$_{1-4}$ alkoxy, NO$_2$, CN and C$_{1-4}$ alkyl-NH—CO—; more preferably, R$_7$ is selected from H, fluoro, chloro, methyl, ethyl, n-propyl, isopropyl, fluoromethyl, difluoromethyl, trifluoromethyl, fluoroethyl, difluoroethyl, trifluoroethyl, methoxy, ethoxy, n-propoxy, isopropoxy, fluoromethoxy, difluoromethoxy, trifluoromethoxy, fluoroethoxy, difluoroethoxy, trifluoroethoxy, NO$_2$, CN and C$_{1-4}$ alkyl-NH—CO—; or (3) R$_6$ and R$_7$ together with the benzene ring to which they are attached form a benzo five-membered ring or benzo six-membered ring, wherein the benzo five-membered ring or benzo six-membered ring is optionally substituted by one or more groups selected from halogen, C$_{1-6}$ alkyl, C$_{1-6}$ alkoxy, halogenated C$_{1-6}$ alkyl, halogenated C$_{1-6}$ alkoxy, phenyl, cyano, C$_{1-6}$ alkyl-OC(O)—, C$_{1-6}$ alkyl-OC(O)—CH$_2$—; preferably, R$_6$ and R$_7$ together with the benzene ring to which they are attached form a 1,2,3,4-tetrahydronaphthalene, 2,3-dihydro-1H-indene, indole, benzofuran, quinoxaline, 4H-chromen-4-one, benzo[d]isoxazole, benzo[d]oxazole, benzo[c][1,2,5]thiadiazole, benzo[b]thiophene, benzodihydropyran-4-one, wherein each of these fused rings is optionally substituted by one or more groups selected from halogen, C$_{1-6}$ alkyl, C$_{1-6}$ alkoxy, halogenated C$_{1-6}$ alkyl, halogenated C$_{1-6}$ alkoxy, phenyl, cyano, C$_{1-6}$ alkyl-OC(O)—, C$_{1-6}$ alkyl-OC(O)—CH$_2$—.

In a preferred embodiment, the present invention provides a compound of general formula Ia or a stereoisomer, salt, hydrate, solvate or crystal thereof, wherein R$_6$ is phenyl-Y— or heterocyclyl-Y—, wherein Y is absent or selected from C$_{1-3}$ alkyl, C$_{2-3}$ alkenyl, C$_{2-3}$ alkynyl, C$_{2-3}$ alkenyl-(CO)—, C$_{2-3}$ alkynyl-(CO)—, O, S, amino and —N(C$_{1-3}$ alkyl), and wherein the phenyl or heterocyclyl is optionally substituted by one or more groups selected from C$_{1-3}$ alkyl, halogen, nitro, C$_{1-3}$ alkoxy, cyano, C$_{2-3}$ alkenyl, C$_{2-3}$ alkynyl, C$_{1-3}$ acylamino, halogenated C$_{1-3}$ alkyl, halogenated C$_{1-3}$ alkoxy, amino, NH(C$_{1-3}$ alkyl), N(C$_{1-3}$ alkyl)$_2$ and C$_{1-3}$ alkyl NHCO, or the phenyl and a five- or six-membered ring taken together form a benzo five-membered ring or benzo six-membered ring. Preferably, the present invention provides the compound of general formula Ia or a stereoisomer, salt, hydrate, solvate or crystal thereof, wherein R$_6$ group "phenyl-Y—" or "heterocyclyl-Y—" and the oxygen group both of which are attached to the benzene ring are at the para- or meta-position to each other.

The present invention provides the compound of general formula Ia or a stereoisomer, salt, hydrate, solvate or crystal thereof, wherein R$_6$ is 1H-imidazolyl, 1,2,4-triazolyl, 1,2,3-triazolyl, thiazolyl, 1,2,3-thiadiazolyl, 1,2,4-thiadiazolyl, 1,3,4-thiadiazolyl, oxazolyl, 1,2,4-oxadiazolyl, 1,2,3-oxadiazolyl, 1,3,4-oxadiazolyl, pyrimidinyl, pyrazinyl, pyridazinyl, quinoxalinyl, 4H-chromen-4-one, thieno[3,2-b]thienyl, 1H-imidazolyl-(CH$_2$)—, 1,2,4-triazolyl-(CH$_2$)—, 1,2,3-triazolyl-(CH$_2$)—, thiazolyl-(CH$_2$)—, 1,2,3-thiadiazolyl-(CH$_2$)—, 1,2,4-thiadiazolyl-(CH$_2$)—, 1,3,4-thiadiazolyl-(CH$_2$)—, oxazolyl-(CH$_2$)—, 1,2,4-oxadiazolyl-(CH$_2$)—, 1,2,3-oxadiazolyl-(CH$_2$)—, 1,3,4-oxadiazolyl-(CH$_2$)—, pyrimidinyl-(CH$_2$)—, pyrazinyl-(CH$_2$)—, pyridazinyl-(CH$_2$)—, quinoxalinyl-(CH$_2$)—, 4H-chromen-4-one-(CH$_2$)—, pyridyl-(CH$_2$)—, thieno[3,2-b]thienyl-(CH$_2$)—, 1H-imidazolyl-=-, 1,2,4-triazolyl-=-, 1,2,3-triazolyl-=-, thiazolyl-=-, 1,2,3-thiadiazolyl-=-, 1,2,4-thiadiazolyl-=-, 1,3,4-thiadiazolyl-=-, oxazolyl-=-, 1,2,4-oxadiazolyl-=-, 1,2,3-oxadiazolyl-=-, 1,3,4-oxadiazolyl-=-, pyrimidinyl-=-, pyrazinyl-=-, pyridazinyl-=-, quinoxalinyl-=-, 4H-chromen-4-one-=-, pyridyl-=-, thieno[3,2-b]thienyl-=-, 1H-imidazolyl-≡-, 1,2,4-triazolyl-≡-, 1,2,3-triazolyl-≡-, thiazolyl-≡-, 1,2,3-thiadiazolyl-≡-, 1,2,4-thiadiazolyl-≡-, 1,3,4-thiadiazolyl-≡-, oxazolyl-≡-, 1,2,4-oxadiazolyl-≡-, 1,2,3-oxadiazolyl-≡-, 1,3,4-oxadiazolyl-≡-, pyrimidinyl-≡-, pyrazinyl-≡-, pyridazinyl-≡-, quinoxalinyl-≡-, 4H-chromen-4-one-≡-, pyridyl-≡-, or thieno[3,2-b]thienyl-≡-, wherein each of these heterocyclyl groups is optionally substituted by one or more groups selected from $C_{1-3}$ alkyl, halogen, nitro, $C_{1-3}$ alkoxy, cyano, halogenated $C_{1-3}$ alkyl, halogenated $C_{1-3}$ alkoxy, $C_{2-3}$ alkenyl, $C_{2-3}$ alkynyl, $C_{1-3}$ acylamino, amino, $NH(C_{1-3}$ alkyl), $N(C_{1-3}$ alkyl)$_2$ and $C_{1-4}$ alkyl NHCO, wherein the heterocyclyl and the oxygen group both of which are attached to the benzene ring are at the para- or meta-position to each other.

In a further preferred embodiment, the present invention provides a compound of general formula Ia or a stereoisomer, salt, hydrate, solvate or crystal thereof, wherein $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, cyano, $C_{2-3}$ alkenyl, $C_{2-3}$ alkynyl, $C_{1-3}$ acylamino, halogenated $C_{1-3}$ alkyl, halogenated $C_{1-3}$ alkoxy, amino, $NH(C_{1-3}$ alkyl), $N(C_{1-3}$ alkyl)$_2$ and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group and the oxygen group both of which are attached to the benzene ring are at the para- or meta-position to each other.

In a further preferred embodiment, the present invention provides a compound of general formula Ia or a stereoisomer, salt, hydrate, solvate or crystal thereof, wherein $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, cyano, $C_{2-3}$ alkenyl, $C_{2-3}$ alkynyl, halogenated $C_{1-3}$ alkyl, halogenated $C_{1-3}$ alkoxy, $C_{1-3}$ acylamino, amino and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group and the oxygen group both of which are attached to the benzene ring are at the para- or meta-position to each other.

In a further preferred embodiment, the present invention provides a compound of general formula Ia or a stereoisomer, salt, hydrate, solvate or crystal thereof, wherein $R_6$ is phenyl-Y—, wherein Y is absent or selected from $C_{1-3}$ alkyl, $C_{2-3}$ alkenyl, $C_{2-3}$ alkynyl, $C_{2-3}$ alkenyl-(CO)— and $C_{2-3}$ alkynyl-(CO)—, and wherein the phenyl is optionally substituted by one or more groups selected from $C_{1-3}$ alkyl, halogen, nitro, $C_{1-3}$ alkoxy, cyano, halogenated $C_{1-3}$ alkyl, halogenated $C_{1-3}$ alkoxy and $C_{1-3}$ alkyl NHCO, or the phenyl and a group selected from oxazolyl, pyrazinyl and pyrrolyl taken together form a benzoxazolyl, benzo[b]pyrazinyl or benzo[b]pyrrolyl, wherein $R_6$ group and the oxygen group both of which are attached to the benzene ring are at the para- or meta-position to each other.

In a further preferred embodiment, the present invention provides a compound of general formula Ia or a stereoisomer, salt, hydrate, solvate or crystal thereof, wherein $R_6$ is phenyl- or benzyl- (i.e., phenyl-$CH_2$—), preferably, the phenyl or benzyl and the oxygen group both of which are attached to the benzene ring are at the para- or meta-position to each other.

In other embodiments, the present invention provides a compound of general formula Ia or a stereoisomer, salt, hydrate, solvate or crystal thereof, wherein $R_6$ is heterocyclyl-Y—, wherein the heterocyclyl can also be furyl, pyr-rolyl, tetrazolyl, furazanyl, dioxadiazolyl, pyranyl, thiopyranyl, piperidinyl, triazinyl, oxazinyl, etc.

The present invention provides the following specific compounds:

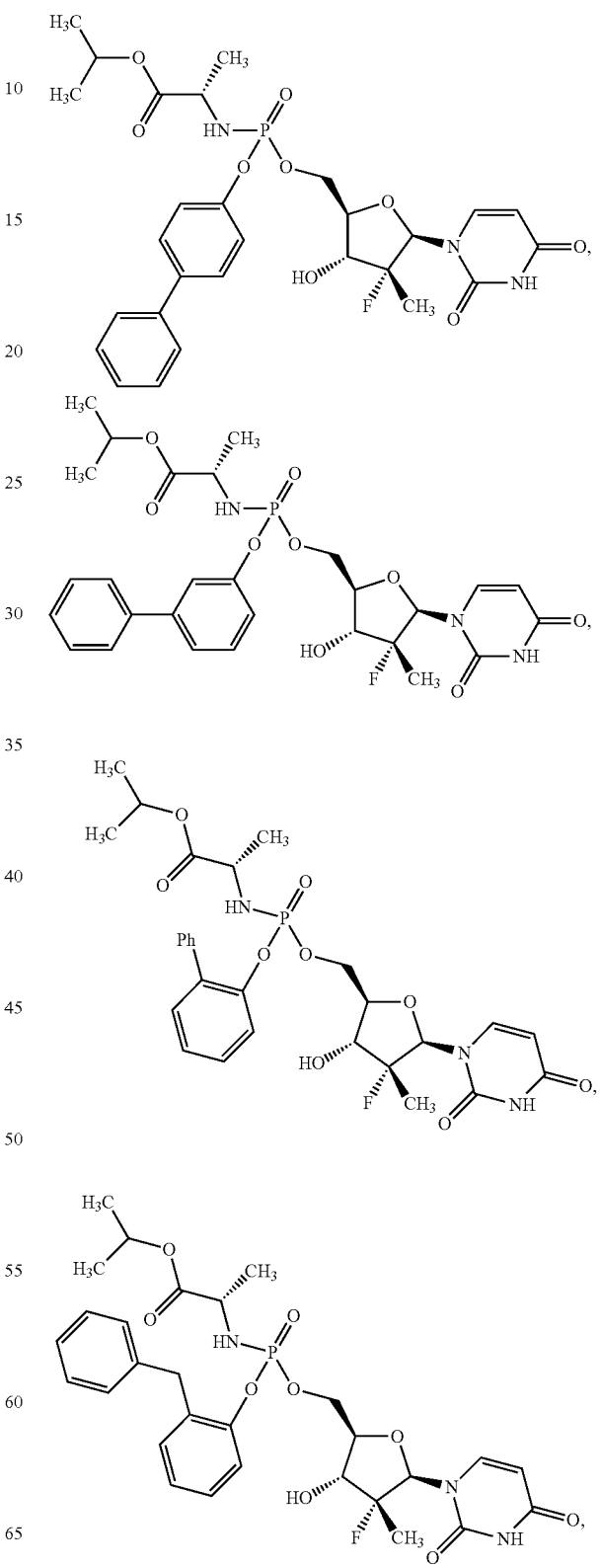

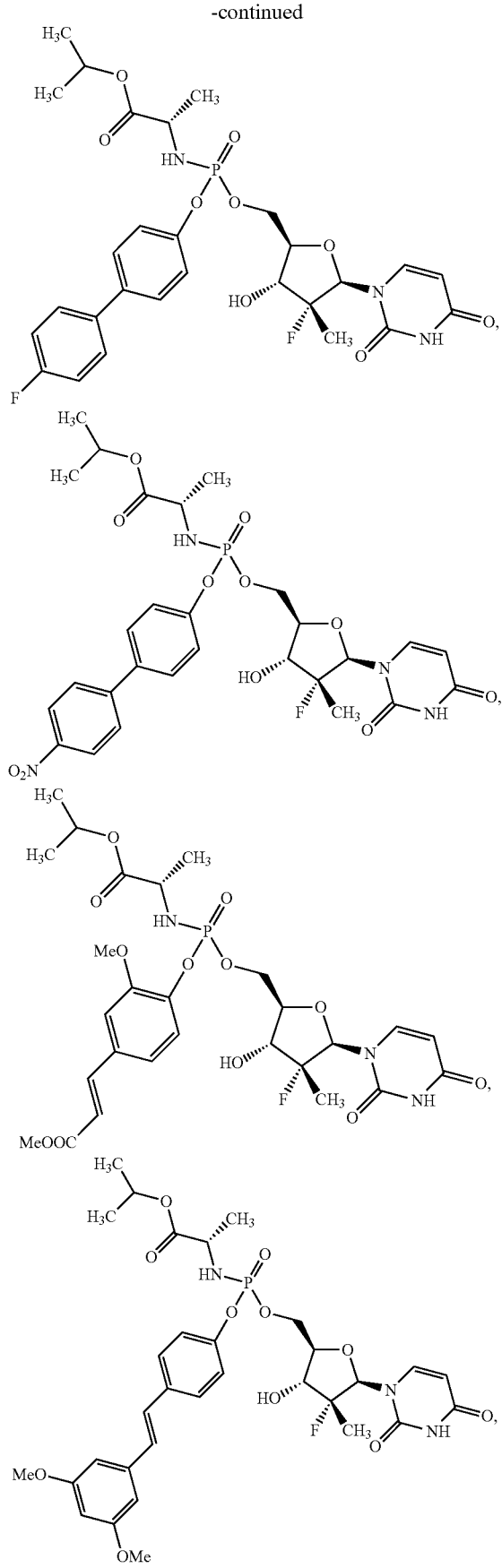
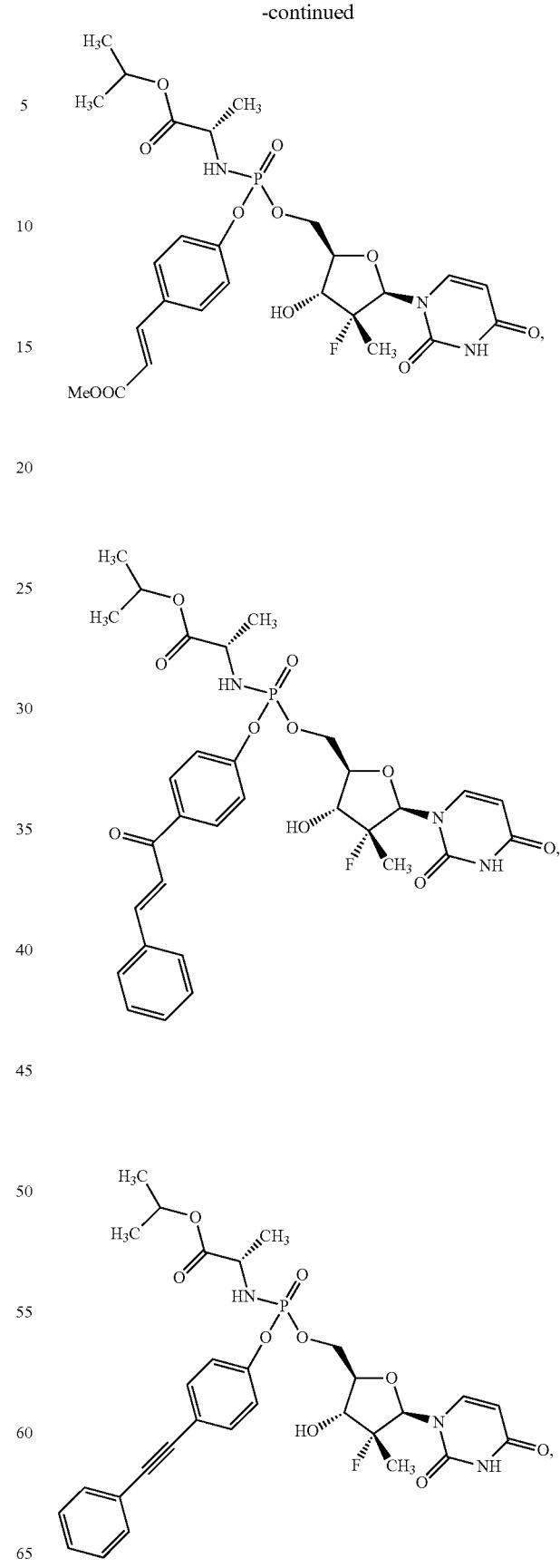

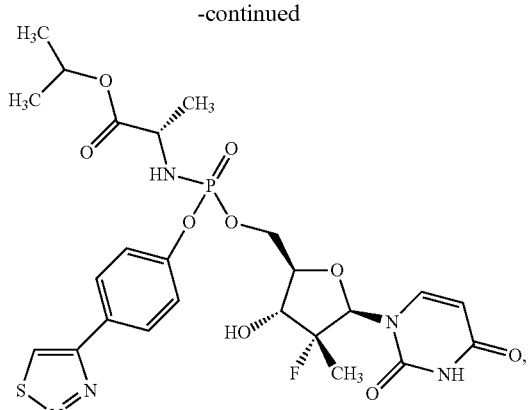
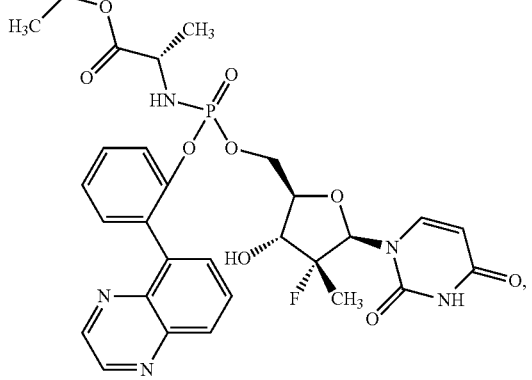
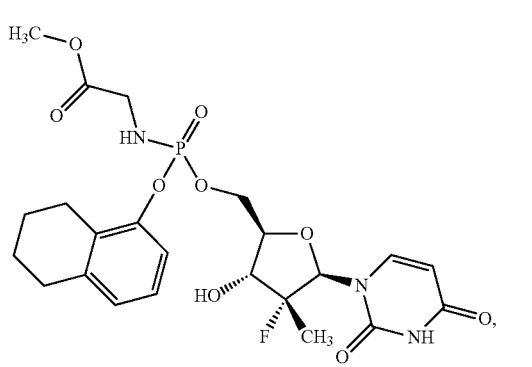
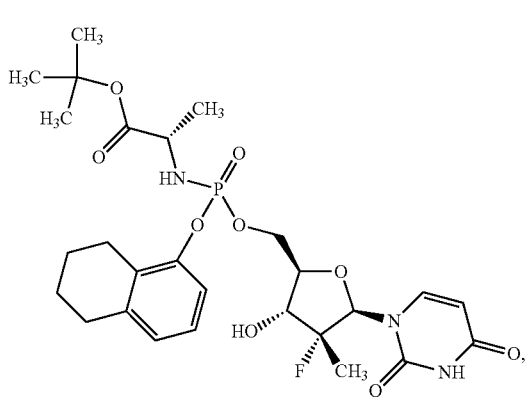
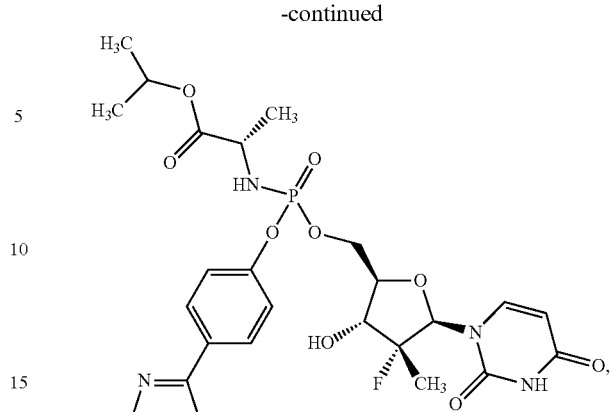
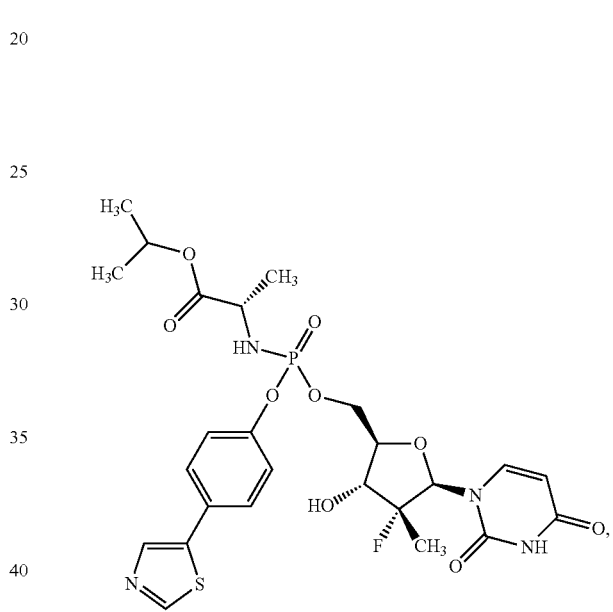
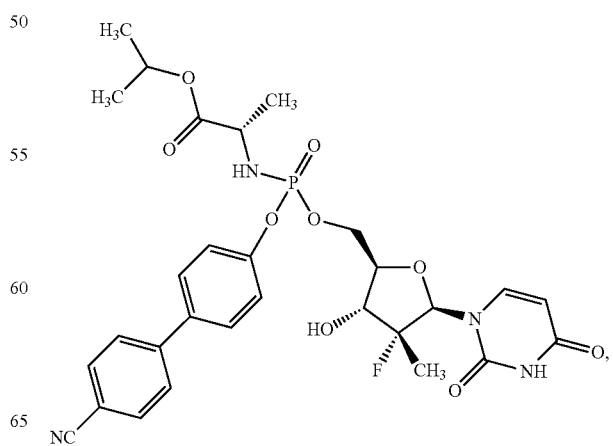

17
-continued
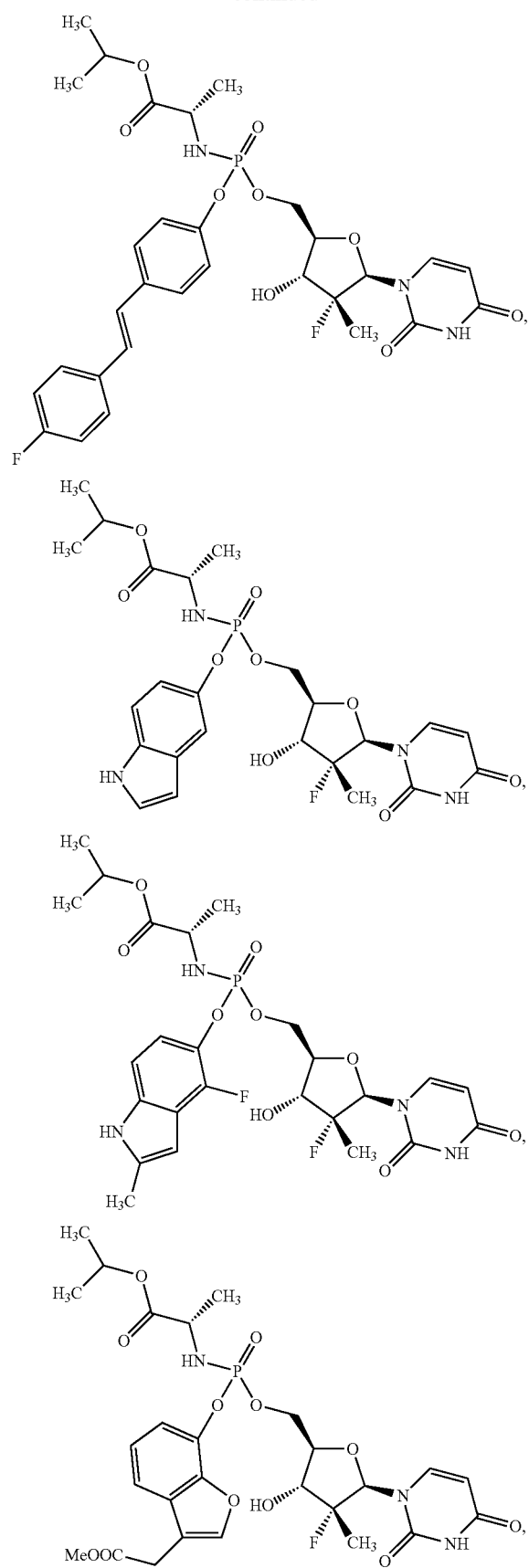
18
-continued
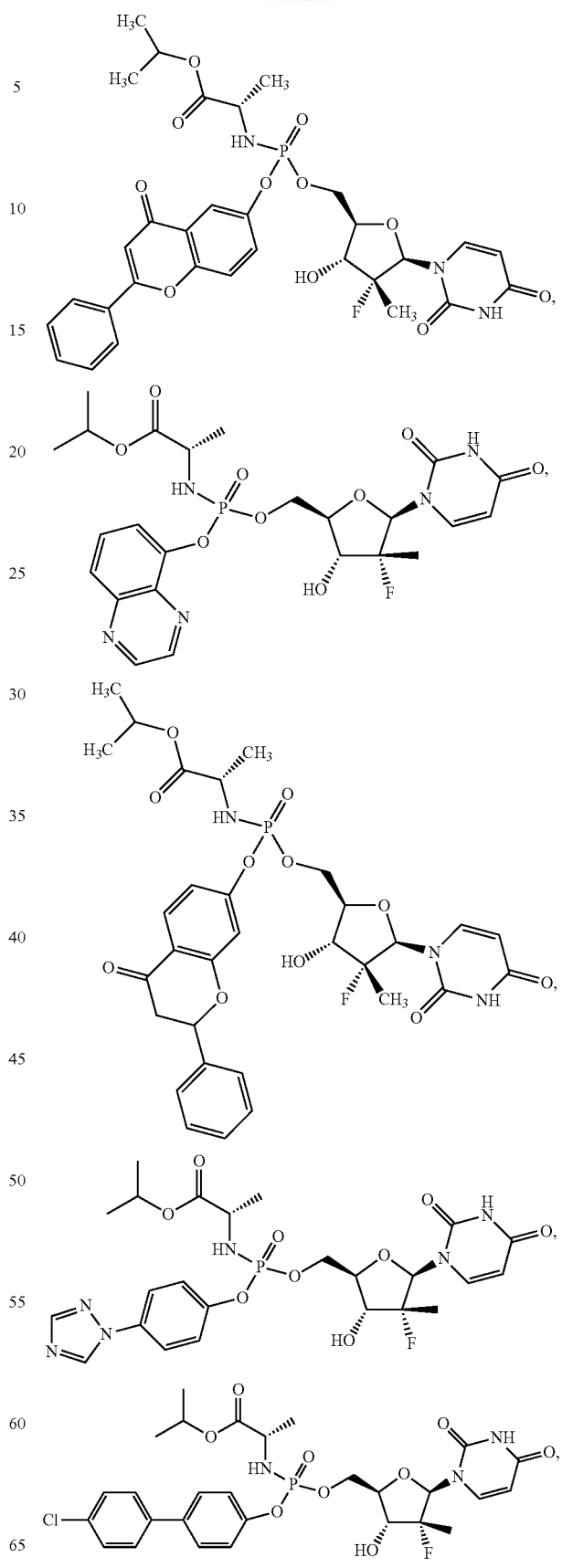

19
-continued
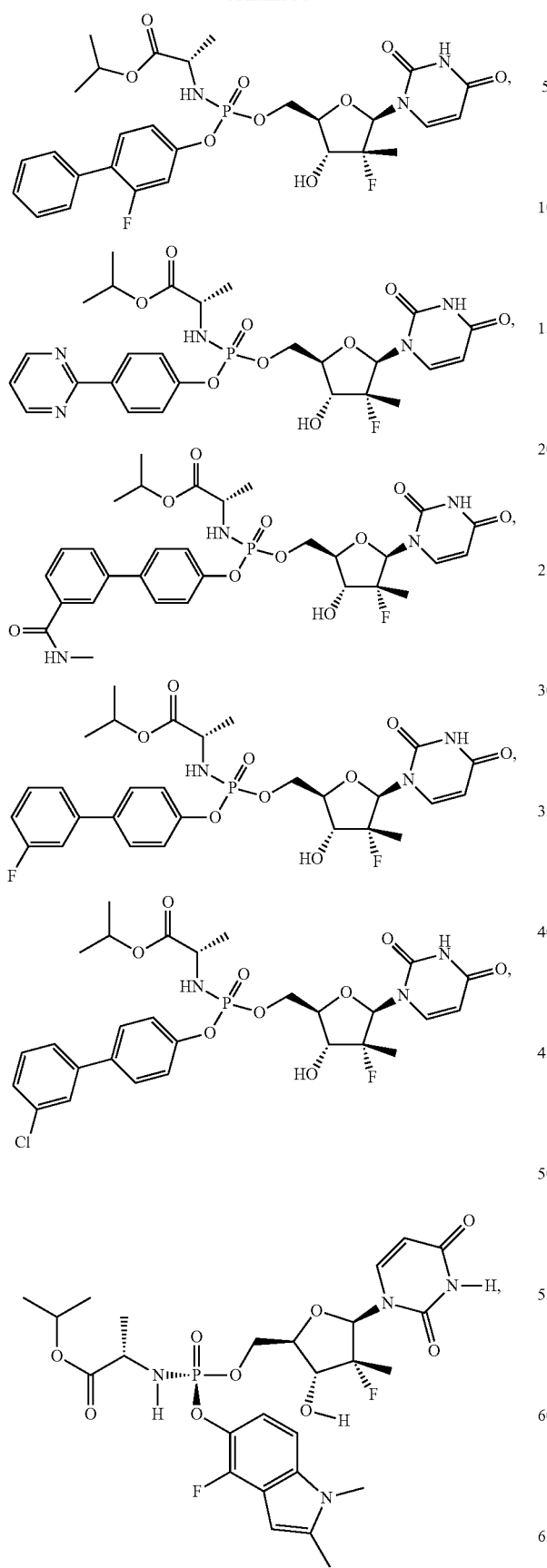
20
-continued
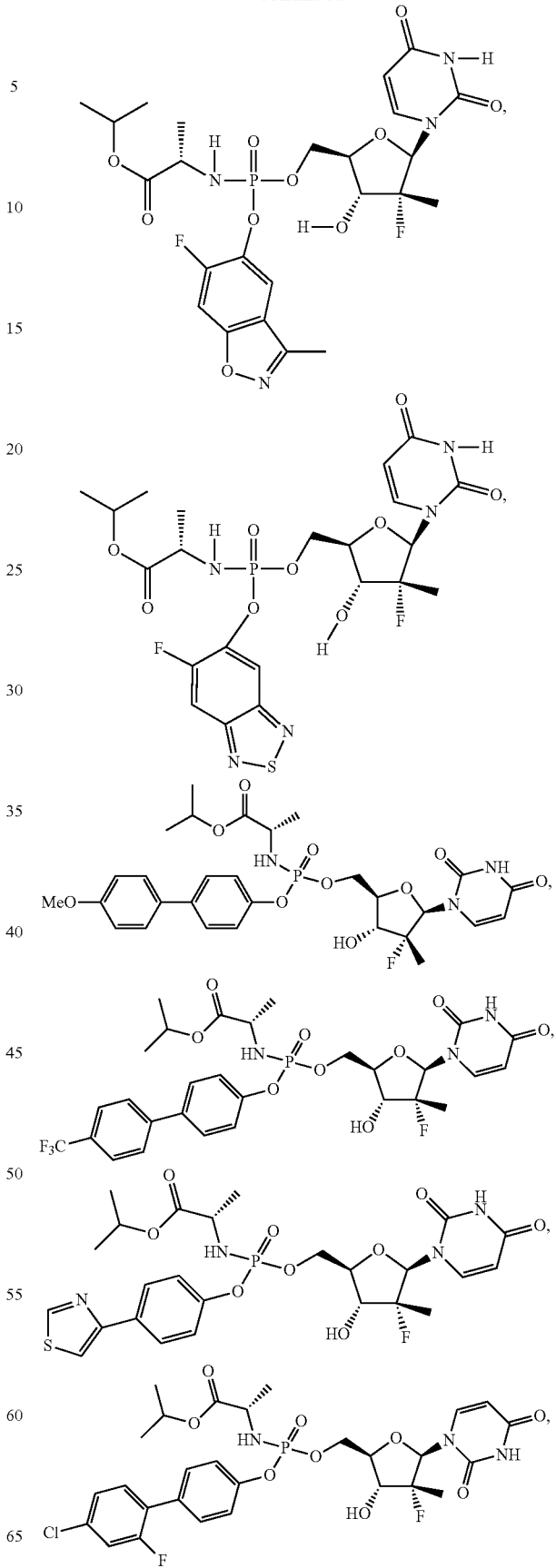

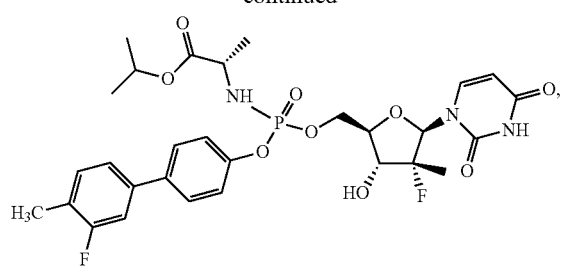

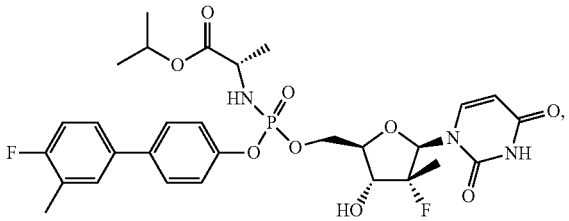

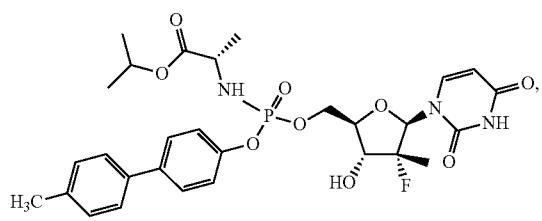

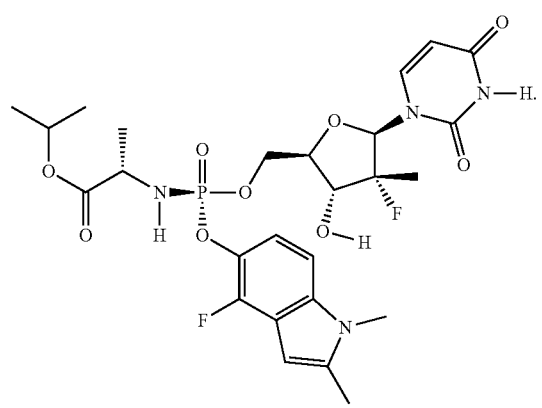

In another aspect, the present invention provides a preparation method of a compound of general formula I or Ia according to the present invention, comprising the following steps:

Synthetic scheme

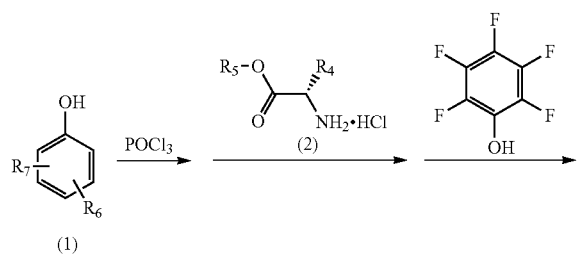

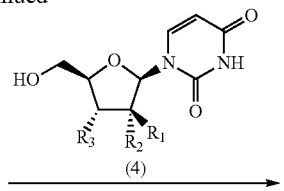

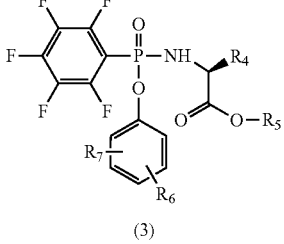

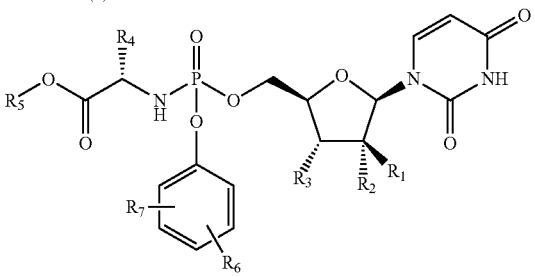

a) reacting compound (1) with phosphorus oxychloride under an alkine condition, followed by adding compound (2), and then adding pentafluorophenol, to obtain compound (3);

b) reacting compound (3) with compound (4) at low temperature, to give the subject compound (5).

wherein $R_1$, $R_2$, $R_3$, $R_4$, $R_5$, $R_6$ and $R_7$ are as defined in general formula I above.

In a third aspect, the present invention provides a pharmaceutical composition comprising a compound of general formula I or Ia according to the present invention, or a stereoisomer, salt, hydrate, solvate or crystal thereof.

In some embodiments, the present invention provides a pharmaceutical composition comprising a compound of general formula I or Ia, or a stereoisomer, salt, hydrate, solvate or crystal thereof, and additional anti-HCV therapeutic agents selected from one or more of the followings: HCV NS3 protease inhibitors, HCV NS5B RNA-dependent RNA polymerase inhibitors, nucleoside analogs, interferon α, pegylated interferon, ribavirin, levovirin, viramidine, TLR7 agonists, TLR9 agonists, cyclophilin inhibitors, α-glucosidase inhibitors, NS5A inhibitors and NS3 helicase inhibitors.

A pharmaceutical formulation may be formulated by mixing the compound of formula I or Ia of the present invention, or a stereoisomer, salt, hydrate, solvate or crystal thereof with a pharmaceutically acceptable carrier, diluent or excipient for suitable for oral or parenteral administration. Methods of administration include, but are not limited to intradermal, intramuscular, intraperitoneal, intravenous, subcutaneous, intranasal and oral routes. The formulations may be administered by any routes, for example by infusion or bolus injection, or via epithelial or mucocutaneous (such as oral or rectal mucosa, etc.) absorption. The administration may be systematic or topical. Examples of formulations for oral administration include solid or liquid dosage forms, specifically, comprising tablets, pills, granules, powder, capsules, syrups, emulsions, suspensions and the like. The formulations may be prepared by methods well known in the art, and may comprise conventional carriers, diluents or excipients in the field of pharmaceutical formulation.

In a fourth aspect, the present invention provides a method of treating a subject infected with virus from the Flaviviridae family using a compound of general formula I or Ia of the present invention, or a stereoisomer, salt, hydrate, solvate or crystal thereof or a pharmaceutical composition of the present invention, comprising administering a compound of general formula I or Ia, or a stereoisomer, salt, hydrate, solvate or crystal thereof or a pharmaceutical composition comprising a compound of general formula I or Ia, or a stereoisomer, salt, hydrate, solvate or crystal thereof to the subject in an amount of effectively reducing the viral load of said virus in said subject. In one embodiment, the present invention provides a method of treating and/or preventing RNA viral infection, e.g. Flaviviridae family viral infection, comprising administering a compound of the present invention, or a stereoisomer, salt, hydrate, solvate, crystal or a pharmaceutical composition thereof to a subject in need thereof. In another embodiment, the present invention provides a method of inhibiting RNA viral infection, e.g. Flaviviridae family viral infection, comprising contacting said virus with a therapeutically effective amount of a compound of the present invention, or a stereoisomer, salt, hydrate, solvate, crystal or a pharmaceutical composition thereof.

"Flaviviridae viruses" means any virus of the Flaviviridae family, including those viruses that infect human or non-human animals, such as *flavivirus, pestivirus* and hepatitis C virus. The compounds and compositions of the present invention may be used particularly for the treatment or preventive treatment of HCV infection.

In another aspect, the present invention provides a use of a compound of general formula I or Ia of the present invention, or a stereoisomer, salt, hydrate, solvate or crystal thereof for prevention or treatment of viral infection diseases, especially Flaviviridae family viral infection diseases, as well as a use of a compound of general formula I or Ia of the present invention, or a stereoisomer, salt, hydrate, solvate or crystal thereof in the manufacture of a medicament for prevention and/or treatment of viral infection diseases, especially for prevention and/or treatment of HCV infection diseases, such as HCV viral hepatitis. Examples of such diseases include acute hepatitis C, chronic hepatitis C, and mixed infection of hepatitis C and hepatitis B or hepatitis D.

Definition

Unless otherwise defined, all technical and scientific terms used herein have the the same meaning as that commonly understood by a person skilled in the art.

The term "stereoisomer" refers to isomers created by a different spatial arrangement of atoms in molecules, including the cis and trans isomers, and enantiomers and conformational isomers. All stereoisomers are within the scope of the present invention. A single stereoisomer of the compound of the present invention may be substantially free of other isomers, or mixed into, for example racemates, or mixed with all other stereoisomers.

The term "salt" refers to a pharmaceutically acceptable salt formed by the compounds of the present invention with an acid. Said acid may be selected from: phosphoric acid, sulfuric acid, hydrochloric acid, hydrobromic acid, citric acid, maleic acid, malonic acid, mandelic acid, succinic acid, fumaric acid, acetic acid, lactic acid, nitric acid, sulfonic acid, p-toluenesulfonic acid, malic acid, methanesulfonic acid or and the like.

The term "solvate" refers to a solid or liquid complex formed by coordination of the compound of the present invention with a solvent molecule. Hydrate is a special form of solvate, wherein the compound coordinates with water. In the context of the present invention, hydrate is a preferred solvate.

The term "crystal" refers to all solid forms formed by the compound of the present invention, comprising crystalline and amorphous forms.

The term "alkyl" refers to a straight-chain, branched chain or cyclic saturated hydrocarbon group, preferably with 6 or less carbon atoms. Examples of alkyl groups include methyl, ethyl, n-propyl, isopropyl, cyclopropyl, n-butyl, isobutyl, t-butyl, cyclobutyl, n-pentyl, isopentyl, neopentyl, cyclohexyl, n-hexyl, isohexyl, 2,2-dimethylbutyl and 2,3-dimethylbutyl. The term "$C_{1-6}$ alkyl" means a straight-chain, branched chain or cyclic saturated hydrocarbon group with 1-6 carbon atoms. The term "$C_{1-4}$ alkyl" means a straight-chain, branched chain or cyclic saturated hydrocarbon group with 1-4 carbon atoms.

The term "alkenyl" means a straight-chain or branched chain unsaturated hydrocarbon group containing one or more carbon-carbon double bonds (C=C), preferably with 2 to 6 carbon atoms, more preferably with 2 to 4 carbon atoms, and most preferably with 2 carbon atoms. The term "$C_{2-6}$ alkenyl" refers to an unsaturated hydrocarbon group of 2 to 6 carbon atoms containing 1 or 2 carbon-carbon double bonds. The term "$C_{2-4}$ alkenyl" refers to an unsaturated hydrocarbon group of 2 to 4 carbon atoms containing 1 or 2 carbon-carbon double bonds.

The term "alkynyl" means a straight-chain or branched chain unsaturated hydrocarbon group containing one or more carbon-carbon triple bond (C≡C), preferably with 2 to 6 carbon atoms, more preferably with 2 to 4 carbon atoms, most preferably with 2 carbon atoms. The term "$C_{2-6}$ alkynyl" refers to an unsaturated hydrocarbon group of 2 to 6 carbon atoms containing 1 or 2 carbon-carbon triple bonds. The term "$C_{2-4}$ alkynyl" refers to an unsaturated hydrocarbon group of 2 to 4 carbon atoms containing 1 or 2 carbon-carbon triple bonds.

The term "alkoxy" refers to —O— alkyl.

The term "halogen" refers to fluorine, chlorine, bromine and iodine.

The term "halogenated alkyl" means an alkyl substituted by at least one halogen atom.

The term "heterocyclyl" refers to a cyclic group containing at least one heteroatom, wherein the heteroatom may be N, O or S, including single heterocyclyl and fused heterocyclyl. The single heterocyclyl group includes, but is not limited to furan, thiophene, pyrrole, thiazole, imidazole, 1,2,3-triazole, 1,2,4-triazole, 1,2,3-thiadiazole, oxazole, 1,2,4-oxadiazole, 1,3,4-oxadiazole, pyridine, pyrimidine, pyridazine, pyrazine, tetrahydrofuran, pyrrolidine, piperidine, piperazine, morpholine, isoxazoline, etc. The fused heterocyclyl group includes, but is not limited to quinoline, isoquinoline, indole, benzofuran, benzothiophene, purine, acridine, carbazole, fluorene, chromene ketone, fluorenone, quinoxaline, 3,4-dihydronaphthalenone, dibenzofuran, dibenzofuran hydride, benzoxazolyl and the like.

The term "benzo five-membered ring" and "benzo six-membered ring" mean a fused ring group.

DETAILED DESCRIPTION OF THE INVENTION

The following examples are provided to illustrate the present invention without limiting the invention to the particulars of these examples. The reagents and starting materials used in the present invention are commercially obtained.

Example 1: (2S)-2-((([1,1'-biphenyl]-4-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

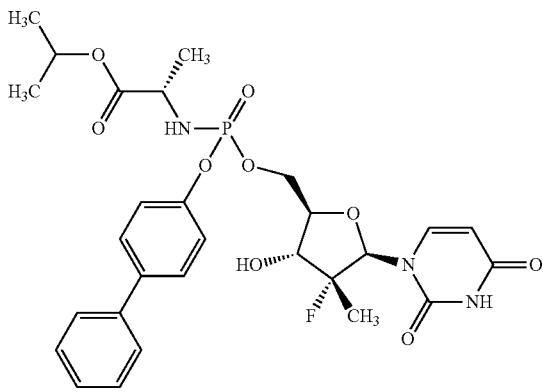 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccccc2)cc1]

Step 1: Preparation of (2S)-2-(((((S)-pentafluorophenoxy)([1,1'-biphenyl]-4-yloxy)phosphoryl)amino)propanoic Acid Isopropyl Ester To a reaction flask were added 0.9 g phosphorus oxychloride (5.87 mmol) and 30 mL dichloromethane. The mixture was cooled to −60° C., and a solution of g p-phenylphenol (5.87 mmol) and 0.6 g triethylamine (5.87 mol) in dichloromethane were added dropwise slowly. After the addition was complete, the mixture was reacted overnight at room temperature, cooled to 0° C., and 0.9 g L-alanine isopropyl ester hydrochloride (5.3 mmol) was added. The mixture was cooled to −60° C., and a solution of 1.34 g triethylamine (13 mmol) in dichloromethane (20 mL) was added dropwise. After the addition was complete, the temperature was raised to −5° C., then a solution of 1 g pentafluorophenol (5.3 mmol) and 0.8 g triethylamine (8 mmol) in dichloromethane (15 mL) was added dropwise to the above mixture solution. The resultant mixture was stirred for 1 hour at −5° C. After completion of the reaction, water was added for extraction, then the mixture was dried, concentrated and separated by silica gel column chromatography to give the title compound.

Step 2: Preparation of (2S)-2-((([1,1'-biphenyl]-4-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester To a reaction flask were added (2'R)-2'-deoxy-2'-fluoro-2'-methyluridine (26 mg, 0.1 mmol) and 1 mL tetrahydrofuran. A solution of 1M tert-butyl magnesium chloride (0.25 mmol) in THF (0.25 mL) was added dropwise under nitrogen protection in an ice bath. After the addition was complete, the mixture was reacted for 4 hours at room temperature, and a solution of the above-obtained phosphate intermediate of p-phenylpheno (70 mg, 0.13 mmol) in tetrahydrofuran (1.5 mL) was added dropwise in an ice bath. After the addition, the mixture was reacted overnight at room temperature. After the reaction was complete, the reaction was quenched by adding 6 mL of 2N HCl in an ice bath. The resultant mixture was extracted with ethyl acetate, washed with saturated sodium bicarbonate solution, dried, concentrated, and separated and purified by silica gel column chromatography to give the title compound.

$^1$HNMR (300 MHz, DMSO) δ: 11.51 (s, 1H, pyrimidineN—H), 7.68-7.62 (m, 4H, Ar—H, pyrimidine-H), 7.60-7.56 (d, 1H, Ar—H), 7.48-7.43 (t, 2H, Ar—H), 7.38-7.30 (m, 3H, Ar—H), 6.12-6.00 (m, 2H, tetrahydrofuran-H), 5.84 (d, 1H, pyrimidine-H), 5.56 (d, 1H, P—NH), 4.90-4.82 (m, 1H, —(CH3)$_2$C—H), 4.62-4.34 (m, 1H, tetrahydrofuran-OH), 4.30-4.22 (m, 1H, (CH3)C(NH)—H), 4.06-4.00 (m, 1H, tetrahydrofuran-H), 3.88-3.77 (m, 2H, P—O—CH$_2$—H), 1.30-1.20 (m, 9H, 3×CH$_3$), 1.58 (d, 3H, CH$_3$).

ESI-MS m/z: [M+H]$^+$=606.2.

Example 2: (2S)-2-((([1,1'-biphenyl]-3-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

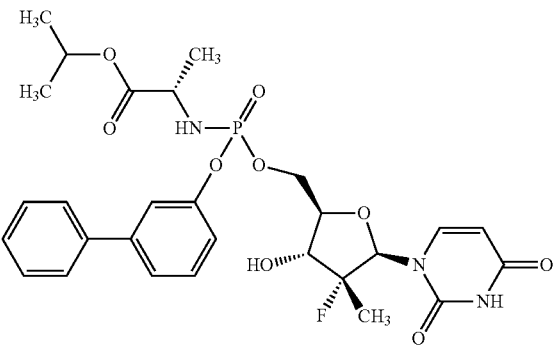 [SMILES: CC(C)OC(=O)[C@H](C)NP(=O)(OC[C@H]1O[C@@H](n2ccc(=O)[nH]c2=O)[C@](C)(F)[C@@H]1O)Oc1cccc(-c2ccccc2)c1]

The title compound was prepared according to the method described in Example 1 using m-phenylphenol, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.50 (s, 1H, pyrimidineN—H), 7.68-7.55 (m, 3H, Ar—H, pyrimidine-H), 7.50-7.36 (m, 6H, Ar—H), 7.21 (d, 1H, Ar—H), 6.13-6.00 (m, 2H, tetrahydrofuran-H), 5.88-5.84 (d, 1H, pyrimidine-H), 5.57-5.52 (d, 1H, P—NH), 4.86-4.82 (m, 1H, —(CH$_3$)$_2$C—H), 4.40-4.38 (m, 1H, tetrahydrofuran-OH), 4.28-4.26 (m, 1H, (CH$_3$)C(NH)—H), 4.04-4.02 (m, 1H, tetrahydrofuran-H), 3.88-3.80 (m, 2H, P—O—CH$_2$—H), 1.28-1.20 (m, 6H, 2×CH$_3$), 1.14-1.11 (d, 6H, 2×CH$_3$).

ESI-MS m/z: [M+H]$^+$=606.2.

Example 3: (2S)-2-((([1,1'-biphenyl]-2-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

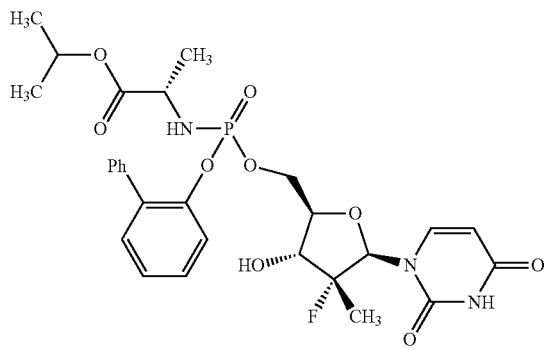 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1-c1ccccc1]

The title compound was prepared according to the method described in Example 1 using o-phenylphenol, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.49 (s, 1H, pyrimidine-N—H), 7.56-7.05 (m, 10OH, Ar—H, pyrimidine-H), 6.38-5.89 (m, 2H, tetrahydrofuran-H), 5.80 (d, 1H, pyrimidine-H), 5.42 (d, 1H, P—NH), 4.86-4.75 (m, 1H, —(CH₃)₂C—H), 4.24-4.18 (m, 1H, tetrahydrofuran-OH), 4.14-4.08 (m, 1H, (CH₃)C(NH)—H), 3.99-3.89 (m, 1H, tetrahydrofuran-H), 3.85-3.72 (m, 2H, P—O—CH₂—H), 1.27-1.23 (m, 3H, CH₃), 1.19-1.07 (d, 9H, 3×CH₃).

ESI-MS m/z: [M+H]⁺=606.2.

Example 4: (2S)-2-(((2-benzylphen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

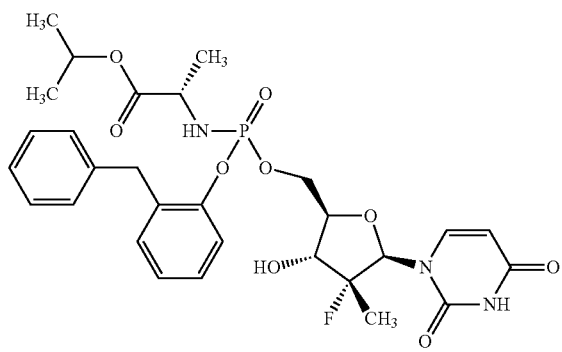 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1Cc1ccccc1]

The title compound was prepared according to the method described in Example 1 using o-benzylphenol, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.48 (s, 1H, pyrimidine-N—H), 7.53-7.05 (m, 1OH, Ar—H, pyrimidine-H), 6.36-5.88 (m, 2H, tetrahydrofuran-H), 5.81 (d, 1H, pyrimidine-H), 5.43 (d, 1H, P—NH), 4.85-4.71 (m, 1H, —(CH₃)₂C—H), 4.21-4.15 (m, 1H, tetrahydrofuran-OH), 4.12-4.01 (m, 1H, (CH₃)C(NH)—H), 3.92-3.89 (m, 1H, tetrahydrofuran-H), 3.81-3.73 (m, 2H, P—O—CH₂—H), 1.32-1.31 (m, 2H, CH₂) 1.23-1.21 (m, 3H, CH₃), 1.11-1.01 (d, 9H, 3×CH₃).

ESI-MS m/z: [M+H]⁺=620.2.

Example 5: (2S)-2-((([4'-fluoro-1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino) propanoic Acid Isopropyl Ester

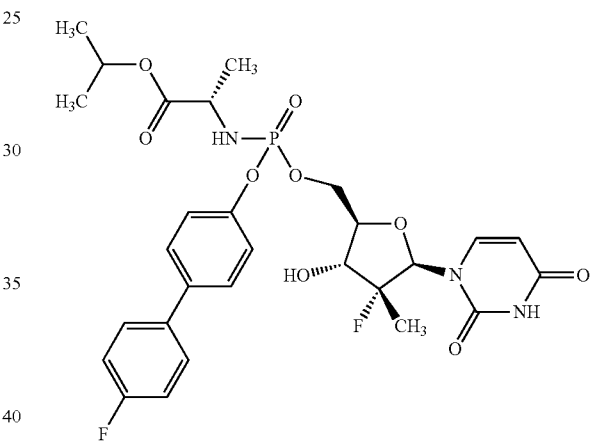

The title compound was prepared according to the method described in Example 1 using 4-fluoro-4'-hydroxybiphenyl, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, CDCl3) δ: 8.09 (s, 1H, pyrimidineN—H), 7.55-7.49 (m, 6H, Ar—H), 7.32 (d 1H, Ar—H), 7.17-7.11 (d, 1H, pyrimidine-H), 6.23-6.18 (m, 1H, tetrahydrofuran-H), 5.76 (d, 1H, pyrimidine-H), 5.09-5.00 (m, 1H, P—NH), 4.62-4.49 (m, 2H, —(CH₃)₂C—H), 4.16-4.12 (m, 1H, tetrahydrofuran-OH), 4.04-3.97 (m, 2H, (CH₃)C(NH)—H), 3.78-3.71 (m, 1H, tetrahydrofuran-H), 1.49 (m, 2H, P—O—CH₂—H), 1.42-1.39 (m, 6H, 2×CH₃), 1.30-1.24 (d, 6H, 2×CH₃).

ESI-MS m/z: [M+H]⁺=624.3.

Example 6: (2S)-2-((([4'-nitro-1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

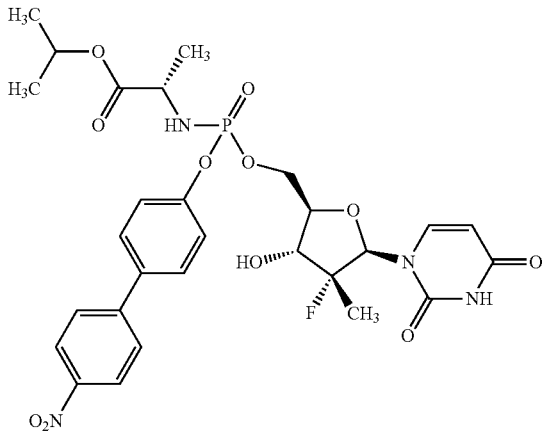 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc([N+](=O)[O-])cc2)cc1]

The title compound was prepared according to the method described in Example 1 using 4-hydroxy-4'-nitro biphenyl, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.48 (s, 1H, pyrimidineN—H), 8.29 (d, 2H, Ar—H), 7.94 (d, 2H, Ar—H), 7.82 (d, 2H, Ar—H), 7.56 (d, 1H, pyrimidine-H), 7.38-7.34 (m, 2H, Ar—H), 6.13-6.04 (m, 2H, tetrahydrofuran-H), 5.83 (d, 1H, pyrimidine-H), 5.56 (d, 1H, P—NH), 4.88-4.85 (m, 1H, —(CH₃)₂C—H), 4.40 (m, 1H, tetrahydrofuran-OH), 4.28 (m, 1H, (CH3)C(NH)—H), 4.04-4.02 (m, 1H, tetrahydrofuran-H) 3.86-3.84 (m, 2H, P—O—CH₂—H), 1.28-1.25 (m, 6H, 2×CH₃), 1.18-1.15 (m, 6H, 2×CH₃).

ESI-MS m/z: [M+H]⁺=651.4.

Example 7: (2S)-2-(((2-methoxy-4-methoxycarbonyl-(E)-ethenylphen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

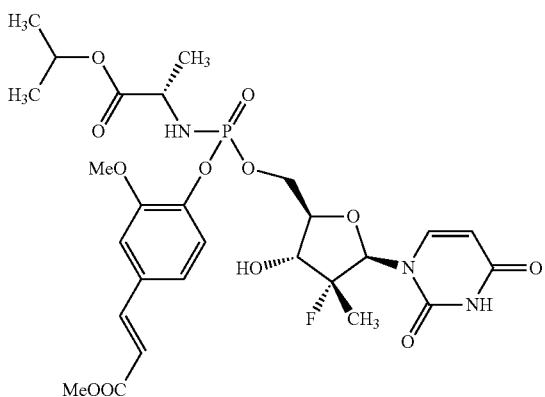 [SMILES: COC(=O)/C=C/c1ccc(OP(=O)(N[C@@H](C)C(=O)OC(C)C)OC[C@H]2O[C@@H](n3ccc(=O)[nH]c3=O)[C@](C)(F)[C@@H]2O)c(OC)c1]

The title compound was prepared according to the method described in Example 1 using (E)-3-(4-hydroxy-3-methoxyphenyl)acrylic acid methyl ester, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.48 (s, 1H, pyrimidine-N—H), 7.62-7.57 (m, 2H, Ar—H, pyrimidine-H), 7.46 (s, 1H, CH=CH), 7.31-7.22 (m, 2H, Ar—H), 6.63 (d, 1H, CH=CH), 6.03-5.93 (m, 2H, tetrahydrofuran-H), 5.88-5.79 (m, 1H, pyrimidine-H), 5.57-5.50 (m, 1H, P—NH), 4.87-4.78 (m, 1H, —(CH3)2C—H), 4.40-4.34 (m, 1H, tetrahydrofuran-OH), 4.25-4.20 (m, 1H, (CH₃)C(NH)—H), 4.05-3.96 (m, 1H, tetrahydrofuran-H), 3.75-3.82 (m, 2H, P—O—CH₂—H), 3.80 (s, 3H, OCH₃), 3.70 (s, 3H, —COOCH₃) 1.26-1.1 (m, 9H, 3×CH₃), 1.13-1.10 (m, 3H, CH₃).

ESI-MS m/z: [M+H]⁺=644.2.

Example 8: (2S)-2-(((((E)-4-(3,5-dimethoxyphenylethenyl)phen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

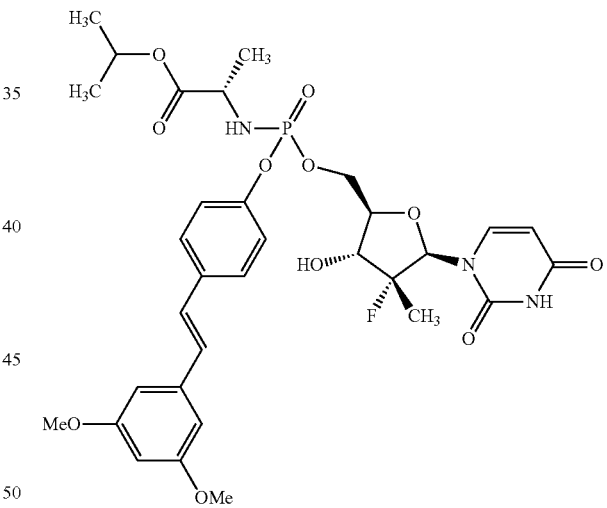

The title compound was prepared according to the method described in Example 1 using (E)-4-(3,5-dimethoxyphenylethenyl)phenol, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.51 (s, 1H, N—H), 8.19 (d, 1H, Ar—H), 7.59 (t, 2H, Ar—H), 7.20 (m, 4H, Ar—H), 6.76 (s, 2H, Ar—H), 6.41 (s, 1H, Ar—H), 6.10 (s, 1H, Ar—H), 6.06 (m, 1H, —CH—), 5.85 (d, 1H, N—H), 5.57 (d, 1H, —CH—), 4.85 (q, 1H, —CH—), 4.37 (m, 2H, —CH—), 4.27 (m, 1H, —OH), 4.01 (m, 1H, —CH₂—), 3.78 (s, 6H, —CH₃), 1.29 (s, 3H, —CH₃), 1.25 (s, 3H, —CH₃), 1.15 (d, 6H, —CH₃).

ESI-MS m/z: [M+H]⁺=692.2.

Example 9: (2S)-2-(((4-methoxycarbonyl-(E)-ethenylphen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

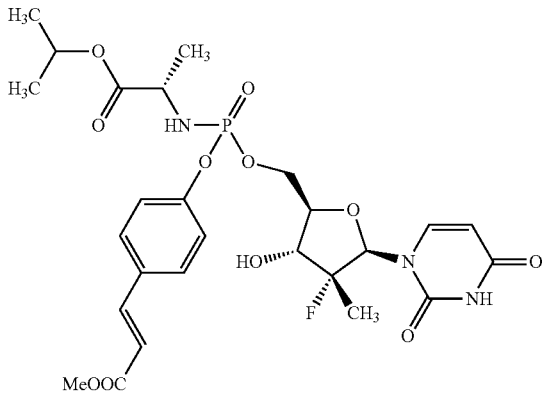 [SMILES: COC(=O)/C=C/c1ccc(OP(=O)(N[C@@H](C)C(=O)OC(C)C)OC[C@H]2O[C@@H](n3ccc(=O)[nH]c3=O)[C@](C)(F)[C@@H]2O)cc1]

The title compound was prepared according to the method described in Example 1 using ((E)-3-(4-hydroxyphenyl) acrylic acid methyl ester, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.50 (s, 1H, pyrimidine-N—H), 7.63-7.59 (m, 2H, Ar—H, pyrimidine-H), 7.48 (s, 1H, CH=CH), 7.32-7.21 (m, 2H, Ar—H), 6.65 (d, 1H, CH=CH), 6.01-5.94 (m, 2H, tetrahydrofuran-H), 5.84-5.78 (m, 1H, pyrimidine-H), 5.51-5.50 (m, 1H, P—NH), 4.88-4.79 (m, 1H, —(CH$_3$)$_2$C—H), 4.42-4.33 (m, 1H, tetrahydrofuran-OH), 4.25-4.18 (m, 1H, (CH$_3$)C(NH)—H), 4.05-3.95 (m, 1H, tetrahydrofuran-H), 3.75-3.82 (m, 2H, P—O—CH$_2$—H), 3.72 (s, 3H, —COOCH$_3$) 1.28-1.12 (m, 9H, 3×CH$_3$), 1.12-1.10 (m, 3H, CH$_3$).

ESI-MS m/z: [M+H]$^+$=644.2.

Example 10: (2S)-2-(((3-cinnamoylphen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

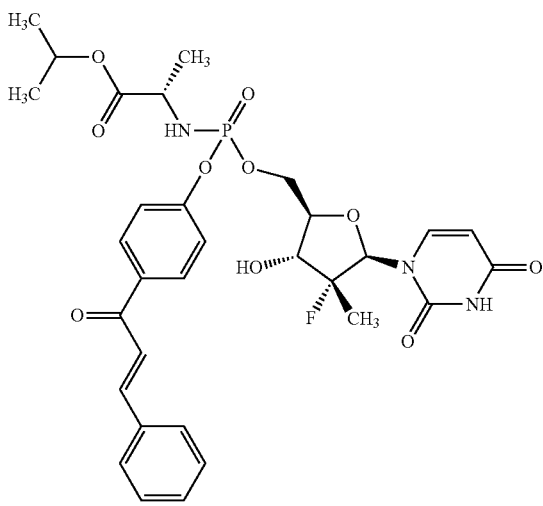 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(C(=O)/C=C/c2ccccc2)cc1]

The title compound was prepared according to the method described in Example 1 using 3-cinnamoylphenol, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.52 (s, 1H, pyrimidineN—H), 7.88-7.82 (m, 1H, pyrimidine-H), 7.78-7.72 (m, 3H, Ar—H), 7.60-7.56 (d, 1H, Ar—H), 7.46 (s, 1H, CH=CH), 7.31-7.22 (m, 4H, Ar—H), 6.63 (d, 1H, CH=CH), 6.12-6.00 (m, 2H, tetrahydrofuran-H), 5.82 (d, 1H, pyrimidine-H), 5.53 (d, 1H, P—NH), 4.91-4.82 (m, 1H, —(CH$_3$)$_2$C—H), 4.63-4.34 (m, 1H, tetrahydrofuran-OH), 4.30-4.22 (m, 1H, (CH$_3$)C(NH)—H), 4.06-4.00 (m, 1H, tetrahydrofuran-H), 3.88-3.77 (m, 2H, P—O—CH$_2$—H), 1.30-1.20 (m, 9H, 3×CH$_3$), 1.58 (d, 3H, CH$_3$).

ESI-MS m/z: [M+Na]$^+$=682.1.

Example 11: (2S)-2-(((4-(phenylethynyl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

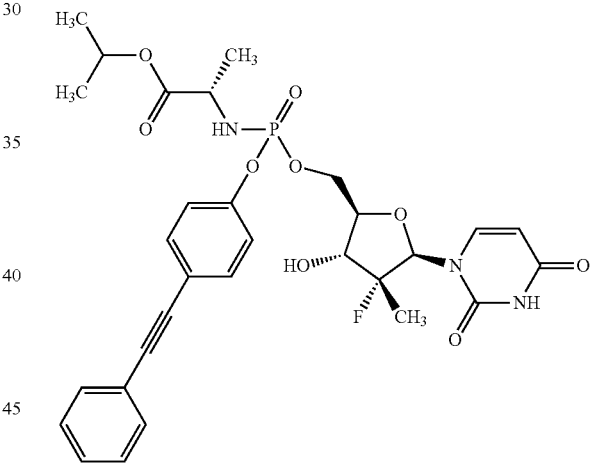

The title compound was prepared according to the method described in Example 1 using 1-(4-hydroxyphenyl)-2-phenyl acetylene, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.49 (s, 1H, pyrimidineN—H), 7.71 (d, 2H, Ar—H), 7.56 (m, 4H, Ar—H, pyrimidine-H), 7.42 (s, 2H, Ar—H), 7.27 (m, 1H), 7.04 (m, 1H), 6.16-6.03 (m, 2H, tetrahydrofuran-H), 5.84 (d, 1H, pyrimidine-H), 5.66-5.52 (m, 1H, P—NH), 4.87-4.83 (m, 1H, —(CH$_3$)$_2$C—H), 4.38 (m, 1H, tetrahydrofuran-OH), 4.25 (m, 1H, (CH3)C(NH)—H), 4.02 (m, 1H, tetrahydrofuran-H), 3.79 (m, 2H, P—O—CH2-H), 1.27-1.23 (m, 6H, 2×CH$_3$), 1.16-1.14 (m, 6H, 2×CH$_3$).

ESI-MS m/z: [M+H]$^+$=630.3.

Example 12: (2S)-2-(((4-(1,2,3-thiadiazol-4-yl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

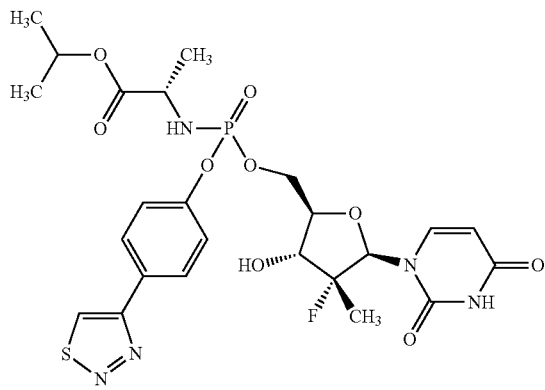 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2csnn2)cc1]

The title compound was prepared according to the method described in Example 1 using 4-(1,2,3-thiadiazol-4-yl)phenol, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.50 (s, 1H, pyrimidineN—H), 9.59 (s, 1H, thiadiazole), 8.14-8.17 (m, 2H, Ar—H), 7.57 (m, 1H, pyrimidine-H), 7.36-7.42 (m, 2H, Ar—H), 6.10-6.17 (m, 2H, tetrahydrofuran-H), 5.90 (d, 1H, pyrimidine-H), 5.59 (d, 1H, P—NH), 4.90-4.82 (m, 1H, —(CH$_3$)$_2$C—H), 4.68-4.36 (m, 1H, tetrahydrofuran-OH), 4.31-4.23 (m, 1H, (CH$_3$)C(NH)—H), 4.06-4.02 (m, 1H, tetrahydrofuran-H), 3.89-3.77 (m, 2H, P—O—CH$_2$—H), 1.30-1.20 (m, 9H, 3×CH$_3$), 1.58 (d, 3H, CH$_3$).

ESI-MS m/z: [M+H]$^+$=614.5.

Example 13: (2S)-2-(((2-(quinoxalin-5-yl)phen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

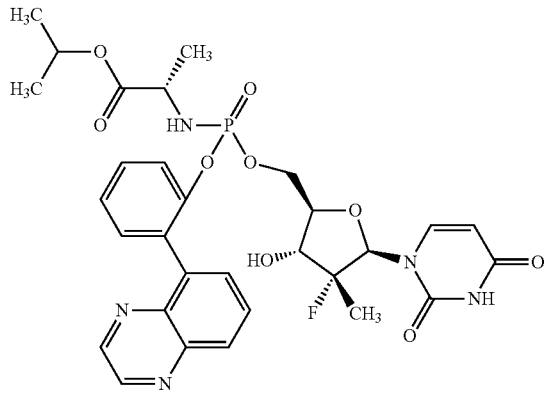 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1-c1cccc2nccnc12]

The title compound was prepared according to the method described in Example 1 using 2-(quinoxalin-5-yl)phenol, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.48 (s, 1H, pyrimidineN—H), 7.69-7.61 (m, 1H, pyrimidine-H), 7.69-7.61 (m, 3H, Ar—H), 7.61-7.58 (d, 1H, Ar—H), 7.49-7.45 (t, 2H, quinoxaline-H), 7.37-7.32 (m, 3H, Ar—H), 6.11-6.03 (m, 2H, tetrahydrofuran-H), 5.82 (d, 1H, pyrimidine-H), 5.53 (d, 1H, P—NH), 4.90-4.83 (m, 1H, —(CH$_3$)$_2$C—H), 4.62-4.32 (m, 1H, tetrahydrofuran-OH), 4.30-4.21 (m, 1H, (CH$_3$)C(NH)—H), 4.04-4.01 (m, 1H, tetrahydrofuran-H), 3.83-3.74 (m, 2H, P—O—CH$_2$—H), 1.34-1.21 (m, 9H, 3×CH$_3$), 1.53 (d, 3H, CH$_3$).

ESI-MS m/z: [M+H]$^+$=658.2.

Example 14: (2S)-2-(((5,6,7,8-tetrahydronaphthalen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)acetic Acid Methyl Ester

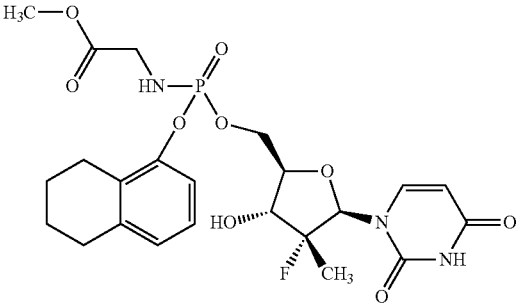 [SMILES: COC(=O)CNP(=O)(OC[C@H]1O[C@@H](n2ccc(=O)[nH]c2=O)[C@](C)(F)[C@@H]1O)Oc1cccc2c1CCCC2]

The title compound was prepared according to the method described in Example 1 using 5,6,7,8-tetrahydro-2-naphthol, phosphorus oxychloride, L-amino acetic acid methyl ester hydrochloride, pentafluorophenol and (2'R)-2'-deoxy-2'-fluoro-2'-methyluridine as starting materials.

$^1$HNMR (300 MHz, DMSO) δ: 11.49 (s, 1H, pyrimidineN—H), 7.58-7.52 (m, 1H, pyrimidine-H), 7.46-7.42 (m, 2H, Ar—H) 7.40-7.36 (d, 1H, Ar—H), 6.11-6.00 (m, 2H, tetrahydrofuran-H), 5.82 (d, 1H, pyrimidine-H), 5.55 (d, 1H, P—NH), 4.91-4.83 (m, 1H, —(CH3)2C—H), 4.64-4.31 (m, 1H, tetrahydrofuran-OH), 4.31-4.23 (m, 2H, (CH$_3$)CH$_2$(NH)), 4.06-4.00 (m, 1H, tetrahydrofuran-H), 3.88-3.77 (m, 2H, P—O—CH$_2$—H), 1.30-1.20 (m, 3H, CH$_3$), 1.5 (d, 3H, CH$_3$).

ESI-MS m/z: [M+H]$^+$=542.2.

Example 15: (2S)-2-(((5,6,7,8-tetrahydronaphthalen-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid t-butyl Ester

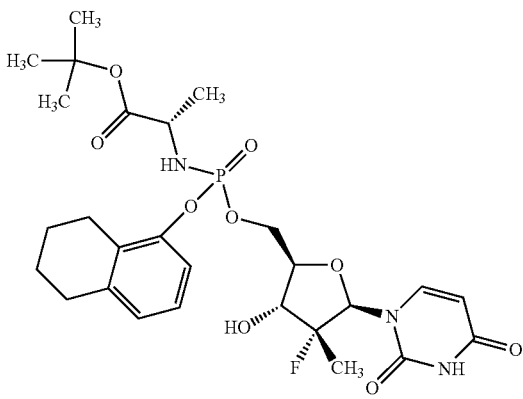 [SMILES: C[C@H](NP(=O)(OC[C@H]1O[C@@H](n2ccc(=O)[nH]c2=O)[C@](C)(F)[C@@H]1O)Oc1cccc2c1CCCC2)C(=O)OC(C)(C)C]

The title compound was prepared according to the method described in Example 1 using 5,6,7,8-tetrahydro-2-naphthol, phosphorus oxychloride, L-alanine t-butyl ester hydrochloride, pentafluorophenol and (2'R)-2'-deoxy-2'-fluoro-2'-methyluridine as starting materials.

$^1$HNMR (300 MHz, DMSO) δ: 11.49 (s, 1H, pyrimidineN—H), 7.58-7.52 (m, 1H, pyrimidine-H), 7.46-7.42 (m, 2H, Ar—H) 7.40-7.36 (d, 1H, Ar—H), 6.11-6.00 (m, 2H, tetrahydrofuran-H), 5.82 (d, 1H, pyrimidine-H), 5.55 (d, 1H, P—NH), 4.64-4.31 (m, 1H, tetrahydrofuran-OH), 4.31-4.23 (m, 1H, (CH$_3$)C(NH)—H), 4.06-4.00 (m, 1H, tetrahydrofuran-H), 3.88-3.77 (m, 2H, P—O—CH$_2$—H), 1.33-1.31 (m, 8H, 4×CH$_2$) 1.30-1.20 (m, 12H, 4×CH$_3$), 1.5 (d, 3H, CH$_3$).

ESI-MS m/z: [M−H]$^+$=596.3.

Example 16: (2S)-2-(((4-(thiazol-2-yl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

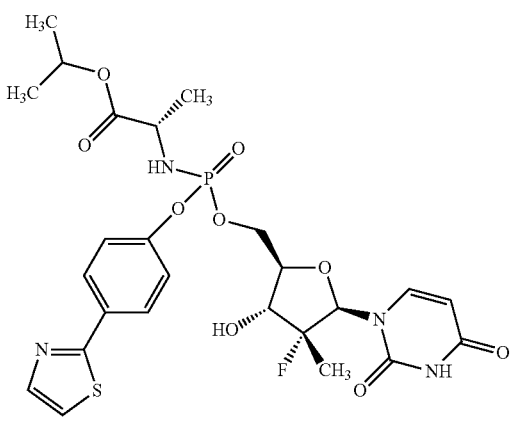 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2nccs2)cc1]

Step 1: Preparation of 2-(4-methoxyphenyl)thiazole

To a 100 mL single-neck flask were added 2.2 g p-methoxyphenyl boronic acid (0.014 mol), 2 g 4-bromothiazole (0.012 mol), 7.8 g cesium carbonate (0.024 mol) and 0.4 g bis(triphenylphosphine)palladium dichloride (0.6 mmol), then added 30 mL 1,4-dioxane and 8 mL water. The mixture was heated to 90° C. under nitrogen protection, and was reacted overnight. The reaction was stopped after the starting materials were almost reacted completely. The mixture was cooled to room temperature, concentrated, and extracted with water and ethyl acetate. The organic phases were combined, dried, concentrated, and separated by silica gel column chromatography to give the title compound.

$^1$HNMR (300 MHz, CDCl3) δ: 7.90-7.95 (m, 2H, Ar—H), 7.83 (d, 1H, Ar—H), 7.26 (d, 1H, Ar—H), 6.95-7.00 (m, 2H, Ar—H), 3.88 (s, 3H, OCH$_3$).

ESI-MS m/z: [M+H]$^+$=192.2.

Step 2: Preparation of 4-(thiazol-2-yl)phenol

To a 100 mL single-neck flask were added the product obtained from Step 1 (0.9 g, 4.7 mmol) and 40% HBr. The product from Step 1 was completely dissolved, and the resulting solution was yellow transparent. 6 mL acetic acid was added, and the solution was heated to 115° C. and reacted for 20 hours. The reaction was stopped after the starting materials almost disappeared. The mixture was concentrated to dryness and separated by silica gel column chromatography to give 0.42 g of a pale yellow solid.

$^1$HNMR (300 MHz, CDCl3) δ: 7.83-7.88 (m, 3H, Ar—H), 7.30 (d, 1H, Ar—H), 6.92 (d, 2H, Ar—H).

ESI-MS m/z: [M+H]$^+$=178.2.

Step 3 Preparation of (2S)-2-(((4-(thiazol-2-yl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-(thiazol-2-yl)phenol, phosphorus oxychloride, L-alanine isopropyl ester hydrochloride, pentafluorophenol and (2'R)-2'-deoxy-2'-fluoro-2'-methyluridine as starting materials.

$^1$HNMR (500 MHz, DMSO) δ: 11.47 (s, 1H, pyrimidineN—H), 7.97-7.90 (m, 3H, Ar-2H, thiazole-1H), 7.76 (d, 1H, thiazole-H), 7.56 (d, 1H, pyrimidine-H), 7.35 (d, 2H, Ar—H), 6.12-6.04 (m, 2H, tetrahydrofuran-H), 5.82 (d, 1H, pyrimidine-H), 5.58-5.56 (m, 1H, P—NH), 4.88-4.83 (m, 1H, —(CH$_3$)$_2$C—H), 4.39 (m, 1H, tetrahydrofuran-OH), 4.28-4.27 (m, 1H, (CH$_3$)C(NH)—H), 4.05-4.01 (m, 1H, tetrahydrofuran-H), 3.84-3.83 (m, 2H, P—O—CH$_2$—H), 1.28-1.24 (m, 6H, 2×CH$_3$), 1.16-1.14 (m, 6H, 2×CH$_3$).

ESI-MS m/z: [M+H]$^+$=613.3.

Example 17: (2S)-2-(((4-(thiazol-5-yl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

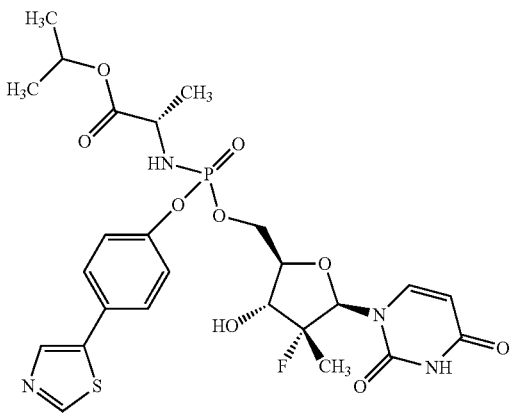 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cncs2)cc1]

Step 1: Preparation of 5-(4-methoxyphenyl)thiazole

To a 100 mL single-neck flask were added 2.2 g p-methoxyphenylboronic acid (0.014 mol), 2 g 5-bromothiazole (0.012 mol), 7.8 g cesium carbonate (0.024 mol) and 0.4 g bis(triphenylphosphine)palladium dichloride (0.6 mmol), then added 30 mL 1,4-dioxane and 8 mL water. The mixture was heated to 90° C. under nitrogen protection, and was reacted overnight. The reaction was stopped after the starting materials were almost reacted completely. The mixture was cooled to room temperature, concentrated, and extracted with water and ethyl acetate. The organic phases were combined, dried, concentrated, and separated by silica gel column chromatography to give a pale yellow solid product.

$^1$HNMR (300 MHz, CDCl$_3$) δ: 8.74 (s, 1H, Ar—H), 8.00 (s, 1H, Ar—H), 7.51-7.54 (m, 2H, Ar—H), 6.95-6.99 (m, 2H, Ar—H), 3.87 (s, 3H, OCH$_3$).

ESI-MS m/z: [M+H]$^+$=192.2.

Step 2: Preparation of 4-(thiazol-5-yl)phenol

To a 100 mL single-neck flask were added the product obtained from Step 1 (0.9 g, 4.7 mmol) and 40% HBr. The product from Step 1 was completely dissolved, and the resulting solution was yellow transparent. 6 mL acetic acid was added, and the mixture was heated to 115° C. and reacted for 20 hours. The reaction was stopped after the starting material almost disappeared. The mixture was concentrated to dryness, extracted with water and ethyl acetate, dried, concentrated, and separated by silica gel column chromatography to give 0.66 g of a pale yellow solid.

$^1$HNMR (300 MHz, CDCl$_3$) δ: 8.72 (s, 1H, Ar—H), 7.99 (s, 1H, Ar—H), 7.43-7.49 (m, 2H, Ar—H), 6.87-6.90 (m, 2H, Ar—H).

ESI-MS m/z: [M+H]$^+$=178.2.

Step 3: Preparation of (2S)-2-(((4-(thiazol-5-yl)phen-1-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-(thiazol-5-yl)phenol, phosphorus oxychloride, L-alanine isopropyl ester hydrochloride, pentafluorophenol and (2'R)-2'-deoxy-2'-fluoro-2'-methyluridine as starting materials.

$^1$HNMR (500 MHz, DMSO) δ: 11.48 (s, 1H, pyrimidineN—H), 9.06 (s, 1H, thiazole-H), 7.97 (d, 1H, thiazole-1H), 7.70 (d, 2H, Ar—H), 7.56 (d, 1H, pyrimidine-H), 7.31 (d, 2H, Ar—H), 6.09-6.01 (m, 2H, tetrahydrofuran-H), 5.81 (d, 1H, pyrimidine-H), 5.57-5.56 (m, 1H, P—NH), 4.88-4.83 (m, 1H, —(CH$_3$)$_2$C—H), 4.38 (m, 1H, tetrahydrofuran-OH), 4.28-4.27 (m, 1H, (CH$_3$)C(NH)—H), 4.05-4.02 (m, 1H, tetrahydrofuran-H), 3.85-3.83 (m, 2H, P—O—CH$_2$—H), 1.28-1.23 (m, 6H, 2×CH$_3$), 1.18-1.14 (m, 6H, 2×CH$_3$).

ESI-MS m/z: [M+H]$^+$=613.4.

Example 18: (2S)-2-((([4'-cyano-1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

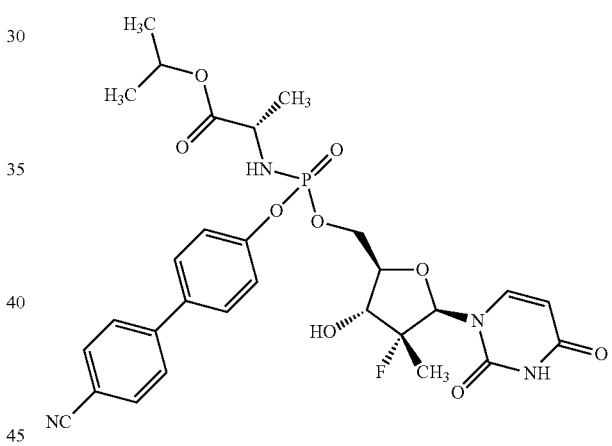

The title compound was prepared according to the method described in Example 1 using 4'-cyano-4-hydroxybiphenyl, phosphorus oxychloride, L-alanine isopropyl ester hydrochloride, pentafluorophenol and (2'R)-2'-deoxy-2'-fluoro-2'-methyluridine as starting materials.

1HNMR (300 MHz, DMSO) δ: 11.50 (s, 1H, pyrimidineN—H), 7.98-7.82 (m, 8H, Ar—H), 7.57 (m, 1H, pyrimidine-H), 6.18-6.15 (m, 2H, tetrahydrofuran-H), 5.91 (d, 1H, pyrimidine-H), 5.59 (d, 1H, P—NH), 4.92-4.87 (m, 1H, —(CH$_3$)$_2$C—H), 4.68-4.36 (m, 2H, tetrahydrofuran-OH, (CH$_3$)C(NH)—H), 4.03-4.01 (m, 1H, tetrahydrofuran-H), 3.85-3.82 (m, 2H, P—O—CH$_2$—H), 1.40-1.29 (m, 9H, 3×CH$_3$), 1.15-1.13 (d, 3H, CH$_3$).

ESI-MS m/z: [M+H]$^+$=631.2.

Example 19: (2S)-2-(((4-((E)-4-fluorophenylethenylphenyl)-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

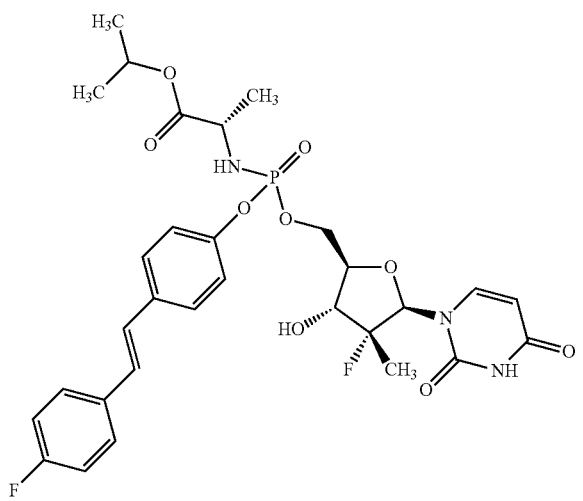 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(/C=C/c2ccc(F)cc2)cc1]

Step 1: Preparation of (E)-4-(4-fluorophenylethenyl)phenol

To a 50 mL three-necked flask were added p-iodophenol (1.32 g, 6 mmol), p-fluorostyrene (610 mg, 5 mmol), tetrakis(triphenylphosphine)palladium (622 mg, 0.5 mmol) and cesium carbonate (4.89 g, 15 mmol), then added 20 mL of 1,4-dioxane. Argon gas was passed through the solution, and the mixture was reacted at 80° C. overnight (about 10 h) until the solution turned black. After 24 h, the reaction was complete by TLC monitoring. Dilute hydrochloric acid was slowly added dropwise at 0° C., and the mixture was extracted with ethyl acetate and separated by silica gel column chromatography to give a white solid.

ESI-MS m/z: [M+H]$^+$=215.2.

Step 2: Preparation of (2S)-2-(((E)-4-(4-fluorophenylethenylphenyl)-1-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using (E)-4-(4-fluorophenylethenyl)phenol, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.46 (s, 1H, pyrimidineN—H), 7.64-7.58 (m, 5H, Ar—H, pyrimidine-H), 7.23-7.15 (m, 6H, Ar—H, —CH=CH—), 6.10-6.15 (m, 2H, tetrahydrofuran-H), 5.91 (d, 1H, pyrimidine-H), 5.79 (d, 1H, P—NH), 4.91-4.88 (m, 1H, —(CH$_3$)$_2$C—H), 4.66-4.32 (m, 2H, tetrahydrofuran-OH, (CH$_3$)C(NH)—H), 4.03-4.01 (m, 1H, tetrahydrofuran-H), 3.85-3.82 (m, 2H, P—O—CH$_2$—H), 1.40-1.29 (m, 9H, 3×CH$_3$), 1.15-1.13 (d, 3H, CH$_3$).

ESI-MS m/z: [M+H]$^+$=650.4.

Example 20: (2S)-2-(((1H-indol-5-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

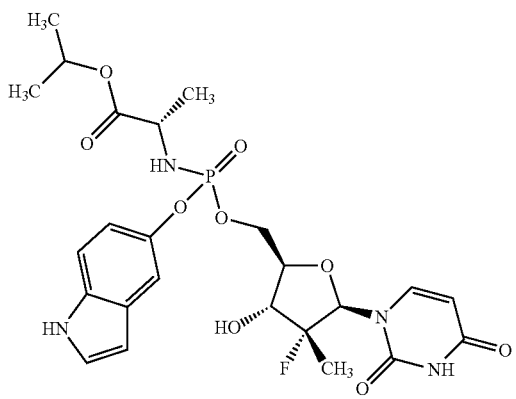 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc2[nH]ccc2c1]

The title compound was prepared according to the method described in Example 1 using 5-hydroxy-1H-indole, phosphorus oxychloride, L-alanine isopropyl ester hydrochloride, pentafluorophenol and (2'R)-2'-deoxy-2'-fluoro-2'-methyluridine as starting materials.

$^1$HNMR (300 MHz, DMSO) δ: 11.54 (s, 1H, pyrimidine-N—H), 11.14 (s, 1H, Indole-N—H), 7.55 (d, 1H, pyrimidine-H), 7.37-7.32 (m, 3H, Indole-H), 6.96 (d, 1H, Indole-H), 6.38 (s, 1H, Indole-H), 6.05-5.84 (m, 3H, tetrahydrofuran-H, pyrimidine-H), 5.55-5.48 (m, 1H, P—NH), 4.88-4.80 (m, 1H, —(CH$_3$)$_2$C—H), 4.38-4.33 (m, 1H, tetrahydrofuran-OH), 4.25-4.20 (m, 1H, (CH$_3$)C(NH)—H), 4.03-4.00 (m, 1H, tetrahydrofuran-H), 3.82-3.74 (m, 2H, P—O—CH$_2$—H), 1.28-1.21 (m, 3H, CH$_3$), 1.17-1.15 (m, 3H, CH$_3$), 1.15-1.12 (m, 6H, 2×CH$_3$).

ESI-MS m/z: [M+H]$^+$=569.2.

Example 21: (2S)-2-(((4-fluoro-2-methyl-1H-indol-5-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

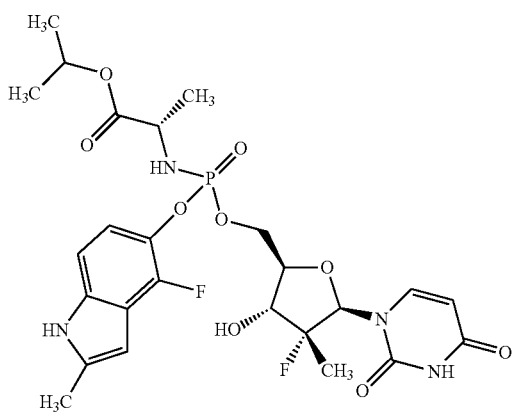 [SMILES: Cc1cc2c(F)c(OP(=O)(N[C@@H](C)C(=O)OC(C)C)OC[C@H]3O[C@@H](n4ccc(=O)[nH]c4=O)[C@](C)(F)[C@@H]3O)ccc2[nH]1]

The title compound was prepared according to the method described in Example 1 using 4-fluoro-5-hydroxy-2-methyl-1H-indole, phosphorus oxychloride, L-alanine isopropyl ester hydrochloride, pentafluorophenol and (2'R)-2'-deoxy-2'-fluoro-2'-methyluridine as starting materials.

¹HNMR (500 MHz, DMSO) δ: 11.48 (s, 1H, pyrimidine-N—H), 11.19 (s, 1H, Indole-N—H), 7.55 (d, 1H, pyrimidine-H), 7.02 (s, 2H, Ar—H), 6.17 (d, 1H, Ar—H), 5.97-5.85 (m, 3H, tetrahydrofuran-H, pyrimidine-H), 5.56-5.49 (m, 1H, P—NH), 4.86 (m, 1H, —(CH₃)₂C—H), 4.41-4.35 (m, 1H, tetrahydrofuran-OH), 4.25-4.20 (m, 1H, (CH₃)C(NH)—H), 4.04-4.00 (m, 1H, tetrahydrofuran-H), 3.82-3.78 (m, 2H, P—O—CH₂—H), 2.37 (s, 3H, CH₃), 1.25-1.22 (m, 6H, 2×CH₃), 1.16-1.14 (m, 6H, 2×CH₃).

ESI-MS m/z: [M+H]⁺=601.3.

Example 22: (2S)-2-(((3-methoxycarbonylmethyl-benzofuran-7-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

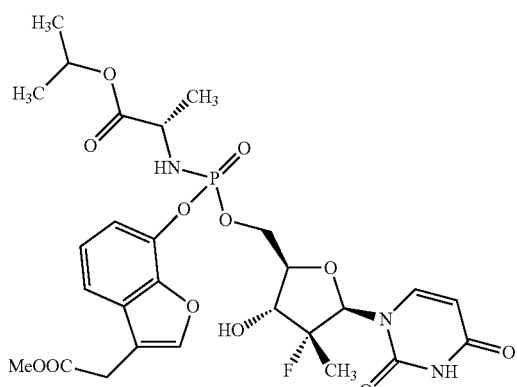

The title compound was prepared according to the method described in Example 1 using 7-hydroxy-3-methoxycarbonylmethylbenzofuran, phosphorus oxychloride, L-alanine isopropyl ester hydrochloride, pentafluorophenol and (2'R)-2'-deoxy-2'-fluoro-2'-methyluridine as starting materials.

¹HNMR (500 MHz, DMSO) δ: 11.48 (s, 1H, pyrimidine-N—H), 7.95 (s, 1H, Furan-H), 7.56 (d, 1H, pyrimidine-H), 7.40 (d, 1H, Ar—H), 7.28 (s, 1H, Ar—H), 7.20 (t, 1H, Ar—H), 6.13 (m, 1H, tetrahydrofuran-H), 6.01 (m, 1H, pyrimidine-H), 5.82 (m, 1H, tetrahydrofuran-H), 5.50 (m, 1H, P—NH), 4.86 (m, 1H, —(CH₃)₂C—H), 4.42 (m, 1H, tetrahydrofuran-OH), 4.31 (m, 1H, (CH₃)C(NH)—H), 4.02 (m, 1H, tetrahydrofuran-H), 3.84-3.82 (m, 4H, P—O—CH₂—H, —CH₂—), 3.65 (s, 3H, CH₃), 1.27-1.22 (m, 6H, 2×CH₃), 1.16-1.14 (m, 6H, 2×CH₃).

ESI-MS m/z: [M+H]⁺=642.2.

Example 23: (2S)-2-(((4-oxo-2-phenyl-4H-benzopyran-6-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

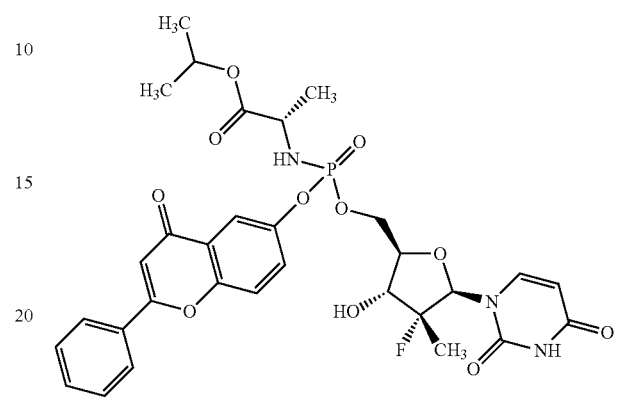

The title compound was prepared according to the method described in Example 1 using 6-hydroxyflavone, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 13.22 (s, 1H, N—H), 8.59 (s, 1H, Ar—H), 8.50 (d, 2H, Ar—H), 8.30 (s, 1H, Ar—H), 8.20 (d, 1H, Ar—H), 8.03 (d, 1H, Ar—H), 7.70 (dd, 2H, Ar—H), 7.61 (d, 1H, Ar—H), 7.48 (m, 1H, Ar—H), 7.38 (d, 1H, Ar—H), 7.36 (d, 1H, N—H), 7.34 (d, 1H, —CH—), 7.26 (m, 1H, —CH—), 5.62 (s, 2H, —CH₂—), 5.54 (s, 1H, —OH), 5.32 (m, 1H, —CH—), 4.59 (m, 1H, —CH—), 4.05 (m, 1H, —CH—), 2.01 (s, 3H, —CH₃), 1.35 (s, 3H, —CH₃), 1.16 (d, 6H, —CH₃).

ESI-MS m/z: [M+H]⁺=674.2.

Example 24: (2S)-2-(((quinoxalin-5-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

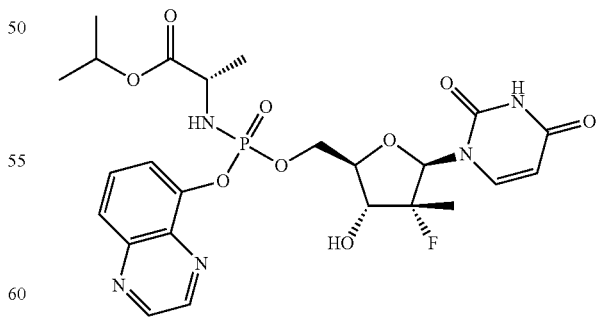

The title compound was prepared according to the method described in Example 1 using 5-hydroxyquinoxaline, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.52 (s, 1H, pyrimidine-N—H), 7.54 (d, 1H, pyrimidine-H), 7.36-7.31 (m, 3H, Ar—H), 6.95 (d, 1H, Ar—H), 6.36 (d, 1H, Ar—H), 6.03-5.82 (m, 3H, tetrahydrofuran-H, pyrimidine-H), 5.55-5.48 (m, 1H, P—NH), 4.88-4.80 (m, 1H, —(CH₃)₂C—H), 4.38-4.33 (m, 1H, tetrahydrofuran-OH), 4.25-4.20 (m, 1H, (CH₃)C(NH)—H), 4.03-4.01 (m, 1H, tetrahydrofuran-H), 3.82-3.74 (m, 2H, P—O—CH₂—H), 1.27-1.25 (m, 3H, CH₃), 1.18-1.16 (m, 3H, CH₃), 1.15-1.12 (m, 6H, 2×CH₃).

ESI-MS m/z: [M+Na]⁺=604.1.

Example 25: (2S)-2-(((4-oxo-2-phenylbenzodihydropyran-7-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

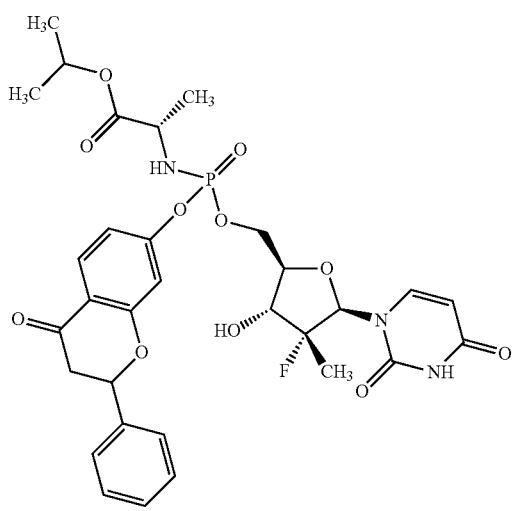 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc2c(c1)OC(c1ccccc1)CC2=O]

The title compound was prepared according to the method described in Example 1 using 7-hydroxyflavanone, phosphorus oxychloride, L-alanine isopropyl ester hydrochloride, pentafluorophenol and (2'R)-2'-deoxy-2'-fluoro-2'-methyluridine as starting materials.

¹HNMR (300 MHz, DMSO) δ: 11.59 (s, 1H, pyrimidineN—H), 8.06-8.02 (m, 1H, Ar—H), 7.89-7.86 (m, 3H, Ar—H) 7.69-7.61 (m, 1H, pyrimidine-H), 7.42-7.41 (m, 2H, Ar—H), 7.36-7.34 (d, 2H, Ar—H), 6.12-6.03 (m, 2H, tetrahydrofuran-H), 5.84 (d, 1H, pyrimidine-H), 5.43 (d, 1H, P—NH), 4.90-4.83 (m, 1H, —(CH₃)₂C—H), 4.63-4.32 (m, 1H, tetrahydrofuran-OH), 4.30-4.21 (m, 1H, (CH₃)C(NH)—H), 4.14-4.11 (m, 1H, tetrahydrofuran-H), 4.10-4.08 (m, 2H, P—O—CH₂—H), 3.98-3.96 (m, 4H, CH₂) 1.98-1.95 (m, 1H, CH) 1.34-1.21 (m, 6H, 2×CH₃), 1.53 (d, 6H, 2×CH₃) ESI-MS m/z: [M+H]⁺=676.2.

Example 26: (2S)-2-((((4-(1H-1,2,4-triazol-1-yl)phenyl oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

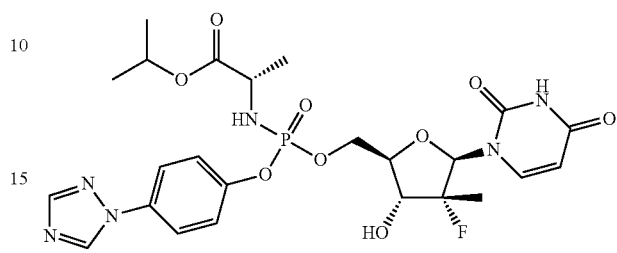

The title compound was prepared according to the method described in Example 1 using 4-(1H-1,2,4-triazol-1-yl)phenol, phosphorus oxychloride, L-alanine isopropyl ester hydrochloride, pentafluorophenol and (2'R)-2'-deoxy-2'-fluoro-2'-methyluridine as starting materials.

¹H NMR (300 MHz, DMSO-d₆) δ ppm: 11.48 (s, 1H), 9.18-9.21 (m, 2H), 8.15-8.18 (m, 1H), 8.05-8.07 (m, 1H), 7.98-8.02 (m, 1H), 7.56-7.58 (m, 1H), 7.15-7.21 (m, 1H), 6.11-6.15 (m, 2H), 5.92 (m, 1H), 5.88 (m, 1H), 4.88-4.92 (m, 1H), 4.32-4.65 (m, 2H), 4.01-4.04 (m, 1H), 3.82-3.86 (m, 2H), 1.13-1.40 (m, 12H).

LC-MS m/z: [M+H]⁺=597.

Example 27: (2S)-2-(((((4'-chloro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

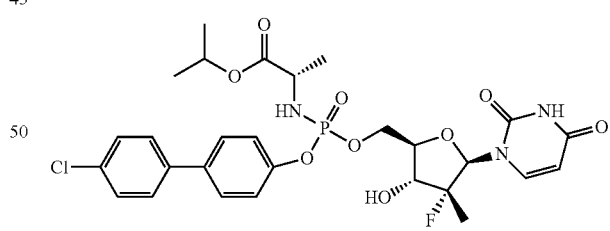

The title compound was prepared according to the method described in Example 1 using 4'-chloro-4-hydroxy[1,1'-biphenyl], phosphorus oxychloride, L-alanine isopropyl ester hydrochloride, pentafluorophenol and (2'R)-2'-deoxy-2'-fluoro-2'-methyluridine as starting materials.

¹H NMR (300 MHz, DMSO-d₆) δ ppm: 11.54 (s, 1H), 7.66-7.69 (d, 3H), 7.55-7.59 (d, 1H), 7.49-7.52 (d, 2H), 7.29-7.33 (m, 3H), 6.12-6.16 (m, 2H), 5.96-5.99 (m, 1H), 5.34 (m, 1H), 4.81-4.89 (m, 1H), 4.38-4.42 (m, 2H), 3.84 (m, 1H), 3.82-3.84 (m, 2H), 1.05-1.14 (m, 12H).

LC-MS m/z [M+H]⁺=640.

Example 28: (2S)-2-(((2-fluoro-[1,1'-biphenyl]-4-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

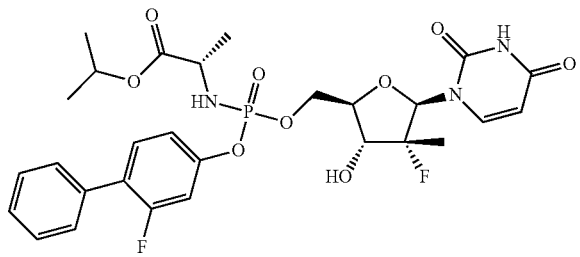 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccccc2)c(F)c1]

Step 1: Preparation of 2-fluoro-4-hydroxy-[1,1'-biphenyl]

In a 250 mL egg plant-shaped flask were added 1.06 g phenylboronic acid, 2.38 g 3-fluoro-4-iodophenol, 0.4 g Pd(dppf)Cl$_2$ and 9 g cesium carbonate, then added 50 mL 1,4-dioxane and 5 mL water. The mixture was stirred at 90° C. for 1.5 h under nitrogen protection, then the reaction was stopped. The reaction solution was extracted with 100 mL ethyl acetate and 50 mL saturated sodium chloride solution, and washed with water (3×50 mL). The organic phases were collected, dried over anhydrous sodium sulfate, filtered, concentrated, and purified by column chromatography to give the title compound.

LC-MS m/z: [M+H]$^+$=189.

Step 2: Preparation of (2S)-2-(((2-fluoro-[1,1'-biphenyl]-4-yloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 2-fluoro-4-hydroxy-[1,1'-biphenyl]prepared from Step 1, phosphorus oxychloride, L-alanine isopropyl ester hydrochloride, pentafluorophenol and (2'R)-2'-deoxy-2'-fluoro-2'-methyluridine as starting materials.

$^1$H NMR (400 MHz, DMSO-d$_6$) δ ppm: 11.49 (s, 1H), 7.51-7.82 (m, 6H), 7.15-7.29 (m, 3H), 6.12-6.15 (m, 1H), 6.03 (m, 1H), 5.97-5.99 (m, 1H), 5.58 (m, 1H), 4.80-4.89 (m, 1H), 4.38-4.41 (m, 2H), 4.01 (m, 1H), 3.82-3.84 (m, 2H), 1.05-1.14 (m, 12H).

LC-MS m/z: [M+H]$^+$=624.

Example 29: (2S)-2-(((4-(pyrimidin-2-yl)phenyloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

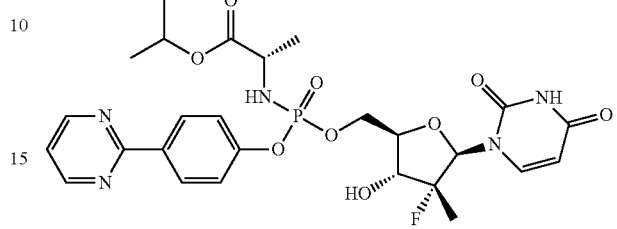

Step 1: Preparation of 2-(4-methoxyphenyl)pyrimidine

The title compound was prepared according to the method described in Step 1 of Example 28 using 4-methoxyphenylboronic acid, 2-bromopyrimidine, Pd(dppf)Cl$_2$ and cesium carbonate as starting materials.

LC-MS m/z: [M+H]$^+$=187.

Step 2: Preparation of 4-(pyrimidin-2-yl)phenol

To a 50 mL round-bottomed flask was added 830 mg 2-(4-methoxyphenyl)pyrimidine prepared from Step 1 in dichloromethane (10 mL). 8 mL of 1N BBr$_3$ was slowly added dropwise at −20° C. under nitrogen protection. After the addition was complete, the mixture was stirred at 0° C. After the reaction was complete, the mixture was quenched by adding 10 mL water, and extracted with dichloromethane (2×20 mL). The organic phases were collected, washed with water and saturated brine, dried over anhydrous sodium sulfate, filtered, concentrated, and purified by column chromatography to give the title compound.

LC-MS m/z: [M+H]$^+$=173.

Step 3: Preparation of (2S)-2-(((4-(pyrimidin-2-yl)phenyloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-(pyrimidin-2-yl)phenol prepared from Step 2, phosphorus oxychloride, L-alanine isopropyl ester hydrochloride, pentafluorophenol and (2'R)-2'-deoxy-2'-fluoro-2'-methyluridine as starting materials.

$^1$HNMR (500 MHz, DMSO-d$_6$) δppm: 11.48 (s, 1H), 8.88-8.89 (m, 2H), 8.38-8.40 (m, 2H), 7.57-7.59 (m, 1H), 7.43-7.44 (m, 1H), 7.35-7.28 (m, 2H), 6.13-6.15 (m, 1H), 6.04 (m, 1H), 5.86-5.88 (m, 1H), 5.59 (m, 1H), 4.81-4.89 (m, 1H), 4.38-4.41 (m, 2H), 4.02 (m, 1H), 3.81-3.84 (m, 2H), 1.10-1.18 (m, 12H).

LC-MS m/z: [M+Na]$^+$=630.

Example 30: (2S)-2-((((3'-(N-methylcarbamoyl)-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

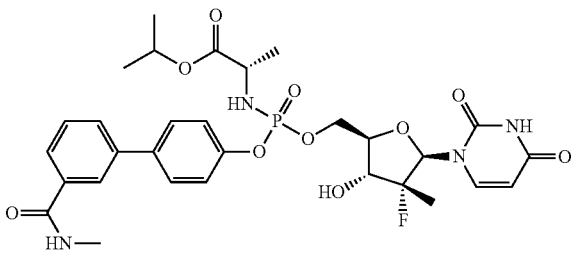 [SMILES: CNC(=O)c1cccc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)c1]

Step 1: 4'-hydroxy-N-methyl-[1,1'-biphenyl]-3-formamide

The title compound was prepared according to the method described in Step 1 of Example 28 using 4-iodophenol, 3-(N-methylcarbamoyl)phenylboronic acid, Pd(dppf)Cl$_2$ and cesium carbonate as starting materials.
LC-MS m/z: [M+H]$^+$=228.

Step 2: Preparation of (2S)-2-((((3'-(N-methylcarbamoyl)-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4'-hydroxy-N-methyl-[1,1'-biphenyl]-3-formamide prepared from Step 1, phosphorus oxychloride, L-alanine isopropyl ester hydrochloride, pentafluorophenol and (2'R)-2'-deoxy-2'-fluoro-2'-methyluridine as starting materials.
$^1$H NMR (400 MHz, DMSO-d$_6$) δ ppm: 11.46-11.50 (s, 1H), 7.95-7.96 (m, 1H), 7.70-7.73 (m, 1H), 7.57-7.59 (m, 1H), 7.35-7.37 (m, 2H), 7.30-7.32 (m, 1H), 7.28-7.31 (m, 1H), 7.22-7.26 (m, 1H), 7.18-7.20 (m, 1H), 7.15-7.17 (m, 1H), 6.08-6.10 (m, 1H), 6.01 (m, 1H), 5.97-6.02 (m, 1H), 5.58 (m, 1H), 4.81-4.88 (m, 1H), 4.38-4.42 (m, 2H), 4.05 (m, 1H), 3.89-3.92 (m, 5H), 1.16-1.28 (m, 12H).
LC-MS m/z: [M−H]$^+$=661.

Example 31: (2S)-2-((((3'-fluoro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino) propanoic Acid Isopropyl Ester

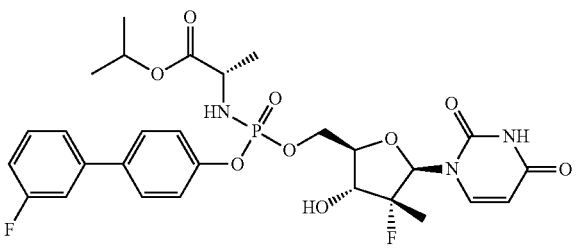 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cccc(F)c2)cc1]

Step 1: Preparation of 4-(3-fluorophenyl)phenol

The title compound was prepared according to the method described in Step 1 of Example 28 using 4-hydroxyphenylboronic acid, 3-fluoroiodobenzene, Pd(dppf)Cl$_2$ and cesium carbonate as starting materials.
LC-MS m/z: [M+H]$^+$=189.

Step 2: Preparation of (2S)-2-((((3'-fluoro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl) amino)propanoic Acid Isopropyl Ester The title compound was prepared according to the method described in Example 1 using 4-(3-fluorophenyl)phenol prepared from Step 1, phosphorus oxychloride, L-alanine isopropyl ester hydrochloride, pentafluorophenol and (2'R)-2'-deoxy-2'-fluoro-2'-methyluridine as starting materials.
$^1$H NMR (400 MHz, DMSO-d$_6$) δ ppm: 11.49 (s, 1H), 7.95-7.97 (m, 1H), 7.70-7.72 (m, 1H), 7.56-7.58 (m, 1H), 7.36-7.38 (m, 2H), 7.31-7.32 (m, 1H), 7.28-7.30 (m, 1H), 7.19-7.20 (m, 1H), 7.16-7.17 (m, 1H), 6.07-6.10 (m, 1H), 6.03 (m, 1H), 5.97-6.01 (m, 1H), 5.56 (m, 1H), 4.80-4.88 (m, 1H), 4.38-4.41 (m, 2H), 4.06 (m, 1H), 3.82-3.86 (m, 2H), 1.16-1.27 (m, 12H).
LC-MS m/z: [M+H]$^+$=624.

Example 32: (2S)-2-((((3'-chloro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino) propanoic Acid Isopropyl Ester

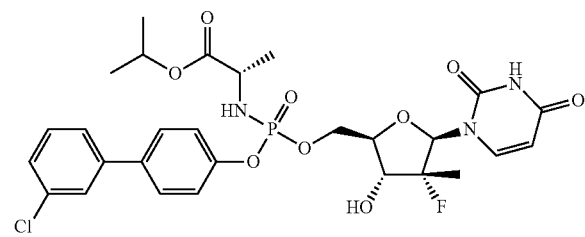 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cccc(Cl)c2)cc1]

Step 1: Preparation of 4-(3-chlorophenyl)phenol

The title compound was prepared according to the method described in Step 1 of Example 28 using 4-hydroxyphenylboronic acid, 3-chloroiodobenzene, Pd(dppf)Cl$_2$ and cesium carbonate as starting materials.
LC-MS m/z: [M+H]$^+$=205.

Step 2: Preparation of (2S)-2-((((3'-chloro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl) amino)propanoic Acid Isopropyl Ester The title compound was prepared according to the method described in Example 1 using 4-(3-chlorophenyl)phenol prepared from Step 1, phosphorus oxychloride, L-alanine isopropyl ester hydrochloride, pentafluorophenol and (2'R)-2'-deoxy-2'-fluoro-2'-methyluridine as starting materials.

$^1$H NMR (400 MHz, DMSO-d$_6$) δ ppm: 11.49 (s, 1H), 7.51-7.82 (m, 6H), 7.26-7.35 (m, 3H), 6.12-6.14 (m, 1H), 6.11 (m, 1H), 5.96-5.98 (m, 1H), 5.88 (m, 1H), 4.80-4.88 (m, 1H), 4.38-4.42 (m, 2H), 4.01 (m, 1H), 3.82-3.87 (m, 2H), 1.11-1.29 (m, 12H).

LC-MS m/z: [M+H]$^+$=640.

Example 33: (2S)-2-(((S)-((4-fluoro-1,2-dimethyl-1H-indol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl) amino)propanoic Acid Isopropyl Ester

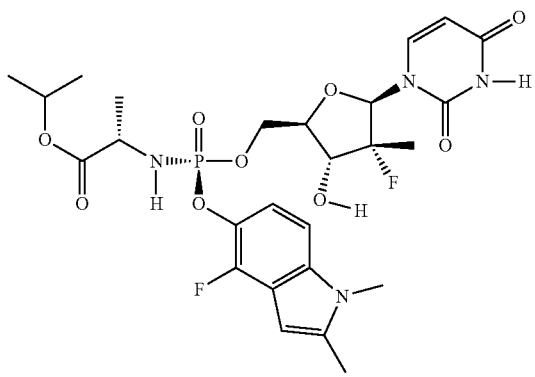 [SMILES: Cc1cc2c(F)c(O[P@](=O)(N[C@@H](C)C(=O)OC(C)C)OC[C@H]3O[C@@H](n4ccc(=O)[nH]c4=O)[C@](C)(F)[C@@H]3O)ccc2n1C]

Step 1: Preparation of 2-(2,3-difluoro-6-nitrophenyl)-3-oxobutanoic acid ethyl ester To a 100 mL round-bottomed flask was added 35 mL tetrahydrofuran, slowly added 1150 mg sodium hydride with stirring in an ice bath, and slowly added 1.43 mL ethyl acetoacetate. After the addition was complete, a solution of 2.3 mL 2,3,4-trifluoronitrobenzene in tetrahydrofuran (4 mL) was added slowly. After the addition was complete, the mixture was reacted for 24 hours at room temperature, then the reaction was stopped by water quenching. 35 mL 2N HCl was added to adjust the pH to neutral, and the mixture was extracted with ethyl acetate. The organic layers were collected, dried over anhydrous sodium sulfate, filtered, and concentrated to give the title compound, which was used directly in the next step.

Step 2: Preparation of 1-(2,3-difluoro-6-nitrophenyl)propan-2-one 2-(2,3-difluoro-6-nitrophenyl)-3-oxobutanoic acid ethyl ester prepared from Step 1 was transferred to a reaction flask, and a mixture of 10 mL concentrated hydrochloric acid and 10 mL glacial acetic acid was added. The solution was reacted for 12 h at 100° C. before the reaction was stopped. The solution was diluted with water and ethyl acetate, and the ethyl acetate layers were obtained. Saturated aqueous NaHCO$_3$ solution was added to adjust the pH to neutral, the ethyl acetate layer was separated, and the aqueous phase was extracted with ethyl acetate. The organic layers were combined, dried over anhydrous Na$_2$SO$_4$, filtered, concentrated, and purified by column chromatography to give the title compound.

$^1$HNMR (400 MHz, DMSO-d$_6$) δppm: 8.04-8.08 (m, 1H), 7.66-7.7 (m, 1H), 4.26-4.26 (d, 2H), 2.30 (s, 3H).

Step 3: Preparation of 1-(2-fluoro-3-methoxy-6-nitrophenyl)propan-2-one

In a 100 mL round-bottomed flask 2 g 1-(2,3-difluoro-6-nitrophenyl)propan-2-one prepared from Step 2 was added to a solution of sodium methoxide in methanol (40 mL), wherein the solution of sodium methoxide in methanol was prepared by slowly adding 2.27 g Na to methanol with stirring in an ice bath and stirring for 1 h at 50° C. after the addition. The mixture was reacted for 1 h at room temperature before the reaction was complete, and quenched by adding 1 mL water and extracted with dichloromethane. The organic layers were washed with saturated brine, dried over anhydrous sodium sulfate, filtered, and concentrated to give the title compound.

$^1$H NMR (400 MHz, DMSO-d$_6$) δ ppm: 8.04-8.07 (m, 1H), 7.31-7.35 (m, 1H), 4.20-4.21 (d, 2H), 3.98 (s, 3H), 2.28 (s, 3H).

Step 4: Preparation of 2-methyl-4-fluoro-5-methoxy-1H-indole

In a 100 mL round-bottomed flask 1.9 g 1-(2-fluoro-3-methoxy-6-nitrophenyl)propan-2-one prepared from Step 3 was added to 15 mL methanol and dissolved, and 190 mg palladium on carbon was added. The mixture was reacted for 36 h at room temperature, then the reaction was stopped. The mixture was filtered, and concentrated to give the title compound.

$^1$H NMR (400 MHz, DMSO-d$_6$) δ ppm: 11.01 (br, 1H), 6.99-7.01 (d, 1H), 6.853 (m, 1H), 6.10-6.11 (t, 1H), 3.79 (s, 3H), 2.35 (s, 3H).

Step 5: Preparation of 1,2-dimethyl-4-fluoro-5-methoxy-1H-indole

In a 100 mL round-bottomed flask 950 mg 2-methyl-4-fluoro-5-methoxy-1H-indole prepared from Step 4 was dissolved in 6 mL tetrahydrofuran, and 87.2 mg sodium hydride was slowly added at 0° C. After the addition was complete, the solution was kept stirring for 30 min, and 0.14 mL iodomethane was slowly added at 0° C. The mixture was reacted for 1 h before the reaction was stopped, then quenched by slowly adding water at 0° C., extracted with ethyl acetate, washed with saturated brine, dried over anhydrous sodium sulfate, filtered, concentrated, and purified by column chromatography to give the title compound.

Step 6: Preparation of 1,2-dimethyl-4-fluoro-5-hydroxy-1H-indole

In a 100 mL round-bottomed flask 210 mg 1,2-dimethyl-4-fluoro-5-methoxy-1H-indole prepared from Step 5 was dissolved in 4 mL anhydrous dichloromethane, and 0.2 mL BBr$_3$ was slowly added at −70° C. The reaction was kept for 2 h at −70° C. before the reaction was stopped. The reaction solution was slowly poured into ice water, and the dichloromethane was removed under reduced pressure. The residue was filtered, and the filter cake was dissolved in methanol, and concentrated to give the title compound.

$^1$H NMR (400 MHz, DMSO-d$_6$) δ: 8.82 (s, 1H), 6.97-6.99 (d, 1H), 6.68-6.72 (t, 1H), 8.12 (s, 1H), 3.59 (s, 3H), 2.35 (s, 3H).

Step 7 (2S)-2-(((S)-((4-fluoro-1,2-dimethyl-1H-indol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl) amino)propanoic Acid Isopropyl Ester The title compound was prepared according to the method described in Example 1 using 1,2-dimethyl-4-fluoro-5-hydroxy-1H-indole prepared from Step 6, phosphorus oxychloride, L-alanine isopropyl ester hydrochloride, pentafluorophenol and (2'R)-2'-deoxy-2'-fluoro-2'-methyluridine as starting materials.

$^1$HNMR (400 MHz, DMSO-d$_6$) δ: 11.48 (s, 1H), 7.52-7.54 (d, 1H), 7.08-7.19 (m, 2H), 6.29 (s, 1H), 5.86-6.08 (m, 3H), 5.47-5.49 (d, 1H), 4.84-4.87 (t, 1H), 4.24-4.36 (m, 2H), 3.77-3.86 (m, 3H), 3.65 (s, 3H), 2.40 (s, 3H), 1.21-1.27 (m, 6H), 1.14-1.16 (m, 6H).

LC-MS m/z: [M+H]$^+$=615.

Example 34: (2S)-2-(((((6-fluoro-3-methylbenzo[d]isoxazol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

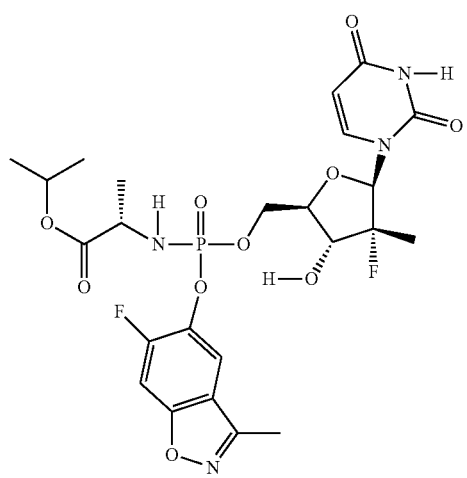 [SMILES: Cc1noc2cc(F)c(OP(=O)(N[C@@H](C)C(=O)OC(C)C)OC[C@H]3O[C@@H](n4ccc(=O)[nH]c4=O)[C@](C)(F)[C@@H]3O)cc12]

Step 1: Preparation of 3-fluoro-4-methoxybenzaldehyde

In a 100 mL round-bottomed flask 1.3 mL 3,4-difluorobenzaldehyde was dissolved in 30 mL methanol, and 2.2 g sodium methoxide was added slowly at room temperature. The mixture was reacted for 12 h before the reaction was stopped, and quenched by adding 3 mL water. Methanol was removed under reduced pressure, and the residue was extracted with dichloromethane. The organic phases were collected, washed with saturated brine, dried over anhydrous sodium sulfate, filtered, concentrated, and purified by column chromatography to give the title compound.

$^1$HNMR (400 MHz, DMSO-d$_6$) δppm: 9.87-9.88 (d, 1H), 7.81-7.82 (m, 1H), 7.79 (m, 1H), 7.40-7.42 (t, 1H), 3.96 (s, 3H).

Step 2: Preparation of (3-fluoro-4-methoxyphenyl)formate

In a 100 mL round-bottomed flask 2.5 g 3-fluoro-4-methoxybenzaldehyde prepared from Step 1 was dissolved in 20 mL anhydrous dichloromethane, and 4.7 g m-chloroperbenzoic acid was added. The mixture was reacted for 4 h at 50° C. before the reaction was stopped. The mixture was diluted with 30 mL dichloromethane, washed with water, brine, dried over anhydrous sodium sulfate, filtered, and concentrated to give the title compound, which was used directly in the next step.

Step 3: Preparation of 3-fluoro-4-methoxyphenol

To a 100 mL round-bottomed flask was added 2.4 g (3-fluoro-4-methoxyphenyl)formate prepared from Step 2, and added 10 mL 5% sodium hydroxide solution and 20 mL methanol. The mixture was reacted for 1 h at room temperature before the reaction was stopped. 2N hydrochloric acid was added to adjust the pH to about 5, and methanol was removed under reduced pressure. The residue was extracted with ethyl acetate, and washed with water and saturated brine. The organic phases were collected, dried over anhydrous sodium sulfate, filtered, concentrated, and purified by column chromatography to give the title compound.

$^1$HNMR (400 MHz, DMSO-d$_6$) δppm: 9.36 (s, 1H), 6.93-6.98 (m, 1H), 6.59-6.62 (m, 1H), 6.50-6.51 (m, 1H), 3.73 (s, 3H).

Step 4: Preparation of (3-fluoro-4-methoxyphenyl)acetate 1.8 g 3-fluoro-4-methoxyphenol prepared from Step 3 was added to a 100 mL round-bottomed flask, and dissolved by adding 25 mL dichloromethane. 1 mL acetyl chloride and 1.9 mL triethylamine were added in an ice bath, and the mixture was reacted for 10 min before the reaction was stopped. 40 mL diethyl ether was added, and the reaction solution was filtered. The filtrate was dried by rotary evaporation to give a yellow solid, to which 30 mL diethyl ether was added. The solution was filtered, and the filtrate was dried by rotary evaporation to give the title compound, which was used directly in the next step.

Step 5: Preparation of 1-(4-fluoro-2-hydroxy-5-methoxyphenyl)ethanone 2 g (3-fluoro-4-methoxyphenyl)acetate prepared from Step 4 was added to a 100 mL round-bottomed flask, and 6.5 mL trifluoromethanesulfonic acid was slowly added at 0° C. The mixture was stirred for another 5 min, and reacted for 75 min at 70° C. before the reaction was stopped. The mixture was cooled to 0° C., and 20 mL ice water was added. The reaction solution was filtered, and the filter cake was washed with water. The filter cake was collected, and dried in vacuum to give the title compound.

$^1$HNMR (400 MHz, DMSO-d$_6$) δppm: 11.95-11.95 (d, 1H), 7.51-7.54 (d, 1H), 6.89-6.92 (d, 1H), 3.85 (s, 3H), 2.65 (s, 3H).

LC-MS m/z: [M+H]$^+$=185.

Step 6: Preparation of (E)-1-(4-fluoro-2-hydroxy-5-methoxyphenyl)ethyl ketoxime 2.4 g 1-(4-fluoro-2-hydroxy-5-methoxyphenyl)ethanone prepared from Step 5 and 1.08 g hydroxylamine hydrochloride were added to a 50 mL round-bottomed flask and dissolved by adding 15 mL ethanol, and 0.6 g sodium hydroxide was slowly added at 50° C. After the addition was complete, the mixture was refluxed for about 1 h before the reaction was stopped. The reaction solution was vigorously stirred at 0-4° C., and 20 mL water was added. The reaction solution was filtered, and the filter cake was washed with cold water, and dried in vacuum to give the title compound.

¹HNMR (400 MHz, DMSO-d₆) δppm: 11.53 (s, 1H), 11.49 (s, 1H), 7.14-7.17 (d, 1H), 6.75-6.782 (d, 1H), 3.81 (s, 3H), 2.23 (s, 3H).

LC-MS m/z: [M+H]⁺=200.

Step 7: Preparation of 6-fluoro-5-methoxy-3-methylbenzo[d]isoxazole 800 mg (E)-1-(4-fluoro-2-hydroxy-5-methoxyphenyl) ethyl ketoxime prepared from Step 6 and 332 mg potassium carbonate were added to a 25 mL round-bottomed flask. 5.8 mL N-methylpyrrolidone (NMP) and 0.4 mL acetic anhydride were added. The mixture was reacted for 3 h at 120° C. under nitrogen protection before the reaction was stopped. The reaction solution was cooled to room temperature, and 10 mL water was added. The reaction solution was filtered, and the filter cake was dissolved with dichloromethane, and dried over anhydrous sodium sulfate, filtered, and concentrated to give the title compound.

¹HNMR (400 MHz, DMSO-d₆) δ ppm: 7.73-7.76 (d, 1H), 7.55-7.57 (d, 1H), 3.39 (s, 3H), 2.53 (s, 3H).

LC-MS m/z: [M+H]⁺=182.

Step 8: Preparation of 3-methyl-5-hydroxy-6-fluoro-benzo[d]isoxazole 400 mg 6-fluoro-5-methoxy-3-methylbenzo[d]isoxazole prepared from Step 7 was added to a 25 mL round-bottomed flask and dissolved by adding 6 mL anhydrous dichloromethane. 0.5 mL boron tribromide was added dropwise slowly at −70° C. under nitrogen protection. After the addition was complete, the mixture was reacted for another 30 min, then the reaction was stopped. The reaction solution was poured into crushed ice, and dichloromethane was removed under reduced pressure. The residue was filtered, and purified by column chromatography to give the title compound.

¹HNMR (400 MHz, DMSO-d₆) δppm: 10.11 (s, 1H), 7.64-7.67 (d, 1H), 7.21-7.23 (d, 1H), 2.50 (s, 3H).

LC-MS m/z: [M+H]⁺=168.

Step 9: Preparation of (2S)-2-(((((6-fluoro-3-methylbenzo[d]isoxazol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 3-methyl-5-hydroxy-6-fluoro-benzo[d]isoxazole prepared from Step 8, phosphorus oxychloride, L-alanine isopropyl ester hydrochloride, pentafluorophenol and (2'R)-2'-deoxy-2'-fluoro-2'-methyluridine as starting materials.

¹HNMR (400 MHz, DMSO-d₆) δppm: 11.53 (s, 1H), 7.86 (m, 2H), 7.57 (s, 1H), 6.28-6.32 (m, 1H), 5.91 (m, 2H), 5.56-5.602 (m, 1H), 4.82-4.86 (m, 1H), 4.31-4.42 (m, 2H), 4.01-4.04 (m, 1H), 3.80-3.85 (m, 2H), 2.52 (s, 3H), 1.22-1.29 (m, 6H), 1.12-1.15 (m, 6H).

LC-MS m/z: [M+H]⁺=603.

Example 35: (2S)-2-(((((6-fluorobenzo[c][1,2,5]thiadiazol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

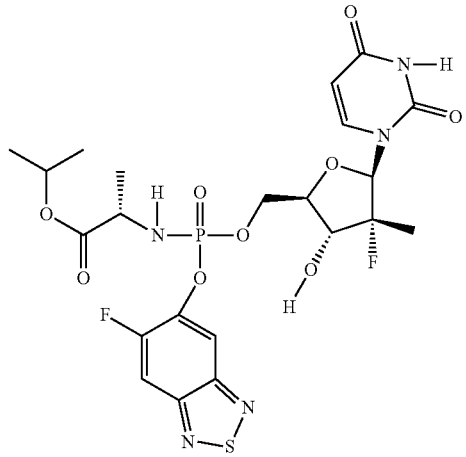 [SMILES: CC(C)OC(=O)[C@H](C)NP(=O)(OC[C@H]1O[C@@H](n2ccc(=O)[nH]c2=O)[C@](C)(F)[C@@H]1O)Oc1cc2nsnc2cc1F]

Step 1: Preparation of 4-fluoro-5-methoxy-2-nitroaniline 3.4 g 2-amino-4,5-difluoronitrobenzene was added to a 100 mL round-bottomed flask, and dissolved by adding 30 mL MeOH. 2.16 g sodium methoxide was slowly added at room temperature. The mixture was reacted for another 12 h at room temperature before the reaction was stopped. The reaction solution was filtered, and the filter cake was washed with 10 mL cold MeOH, and dried in vacuum to give the title compound, which was used directly in the next step.

LC-MS m/z: [M+H]⁺=187.

Step 2: Preparation of 4-fluoro-5-methoxy-1,2-phenylenediamine 2.7 g 4-fluoro-5-methoxy-2-nitroaniline prepared from Step 1 was added to a 100 mL round-bottomed flask, 30 mL MeOH was added, and 270 mg Pd/C was slowly added at room temperature. The mixture was reacted for 3 h at 50° C. under hydrogen atmosphere before the reaction was stopped. The reaction solution was filtered, and the filter cake was washed with cold MeOH (10 mL×2). The filtrate was concentrated to give the title compound, which was used directly in the next step.

LC-MS m/z: [M+H]⁺=157.

Step 3: Preparation of 5-fluoro-6-methoxybenzo[c][1,2,5]thiadiazole 1.5 g 4-fluoro-5-methoxy-1,2-phenylenediamine prepared from Step 2 was added to a 100 mL round-bottomed flask and dissolved by adding 20 mL pyridine. 2.36 g SOCl₂ was slowly added at 0° C. The mixture was reacted for 12 h at 50° C. under nitrogen protection before the reaction was stopped. The reaction solution was poured into 10 g ice, and extracted with ethyl acetate. The organic layers were collected, washed successively with water, 0.5N cold diluted hydrochloric acid and saturated brine, dried, concentrated, and purified by column chromatography to give the title compound.

$^1$H NMR (400 MHz, DMSO-$d_6$) δ ppm: 7.99-8.02 (d, 1H), 7.65-7.67 (d, 1H), 4.02 (s, 3H).

LC-MS m/z: [M+H]$^+$=185.

Step 4: Preparation of 5-hydroxy-6-fluorobenzo[c][1,2,5]thiadiazole 500 mg 5-fluoro-6-methoxybenzo[c][1,2,5]thiadiazole prepared from Step 3 was added to a reaction flask, and 4 mL 40% HBr aqueous solution was added. The mixture was reacted for 12 h at 90° C. under a sealed condition before the reaction was stopped. The reaction solution was cooled to room temperature and filtered. The filter cake was washed with water and dried in vacuum to give the title compound.

LC-MS m/z: [M+H]$^+$=171.

Step 5: Preparation of (2S)-2-(((((6-fluorobenzo[c][1,2,5]thiadiazol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 5-hydroxy-6-fluorobenzo[c][1,2,5]thiadiazole prepared from Step 4, phosphorus oxychloride, L-alanine isopropyl ester hydrochloride, pentafluorophenol and (2'R)-2'-deoxy-2'-fluoro-2'-methyluridine as starting materials.

$^1$HNMR (400 MHz, DMSO-$d_6$) δppm: 11.54-11.56 (m, 1H), 8.08-8.20 (m, 2H), 7.57 (m, 1H), 6.48-6.54 (m, 1H), 5.91-6.10 (m, 2H), 5.52-5.18 (m, 1H), 4.78-4.85 (m, 1H), 4.35-4.38 (m, 2H), 3.81-4.07 (m, 3H), 1.16-1.30 (m, 6H), 1.11-1.13 (m, 6H).

LC-MS m/z: [M+H]$^+$=606.

Example 36: (2S)-2-(((((4'-methoxy-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

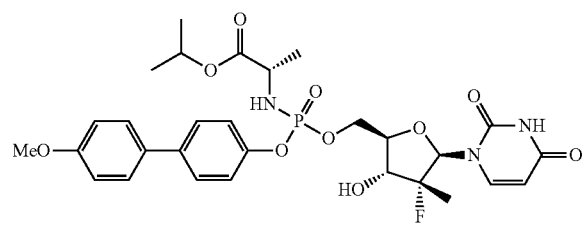 [SMILES: COc1ccc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)cc1]

The title compound was prepared according to the method described in Example 1 using 4-hydroxy-4'-methoxy-1,1'-biphenyl, phosphorus oxychloride, L-alanine isopropyl ester hydrochloride, pentafluorophenol and (2'R)-2'-deoxy-2'-fluoro-2'-methyluridine as starting materials.

$^1$HNMR (500 MHz, DMSO) δ: 11.49 (s, 1H), 7.61-7.55 (m, 5H), 7.28-7.23 (m, 2H), 7.01 (d, 2H), 6.05-6.01 (m, 2H), 5.84-5.82 (m, 1H), 5.57-5.55 (m, 1H), 4.88-4.84 (m, 1H), 4.41-4.37 (m, 1H), 4.27-4.25 (m, 1H), 4.05-4.01 (m, 1H) 3.84-3.82 (m, 2H), 2.333.79 (s, 3H) 1.28-1.22 (m, 6H), 1.18-1.15 (m, 6H).

ESI-MS m/z: [M+H]$^+$=636.1.

Example 37: Preparation of (2S)-2-(((((4'-trifluoromethyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

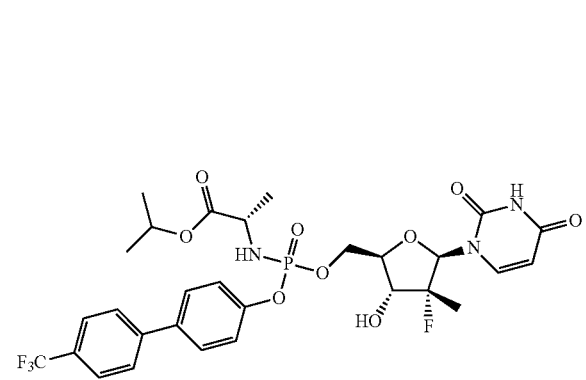

Step 1: Preparation of 4-hydroxy-4'-trifluoromethyl-[1,1'-biphenyl]

2 g 4-iodobenzotrifluoride and 1.2 g p-hydroxyphenylboronic acid were added to a 100 mL single-neck flask, and 2 g potassium carbonate, 0.26 g PdCl$_2$(PPh$_3$)$_2$, 30 mL 1,4-dioxane and 10 mL water were added. The mixture was reacted for 4 h at 70° C. under nitrogen protection before the reaction was stopped. The resultant mixture was concentrated, and 10 mL water was added. The mixture was extracted with ethyl acetate (2×10 mL), dried, filtered, concentrated, and purified by column chromatography to give the title compound.

Step 2: Preparation of (2S)-2-(((((4'-trifluoromethyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-hydroxy-4'-trifluoromethyl-[1,1'-biphenyl]prepared from Step 1, phosphorus oxychloride, L-alanine isopropyl ester hydrochloride, pentafluorophenol and (2'R)-2'-deoxy-2'-fluoro-2'-methyluridine as starting materials.

$^1$HNMR (500 MHz, DMSO) δ: 11.49 (s, 1H), 7.87 (d, 2H), 7.80 (d, 2H), 7.76 (d, 2H), 7.57 (d, 1H), 7.36 (d, 2H), 6.11-6.01 (m, 2H), 5.88-5.83 (m, 1H), 5.60-5.55 (m, 1H), 4.89-4.84 (m, 1H), 4.42-4.39 (m, 1H), 4.28-4.26 (m, 1H), 4.04-4.02 (m, 1H), 3.85-3.84 (m, 2H), 1.28-1.24 (m, 6H), 1.16-1.14 (m, 6H).

ESI-MS m/z: [M+H]$^+$=674.

Example 38: (2S)-2-(((4-(thiazol-4-yl)phenyloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

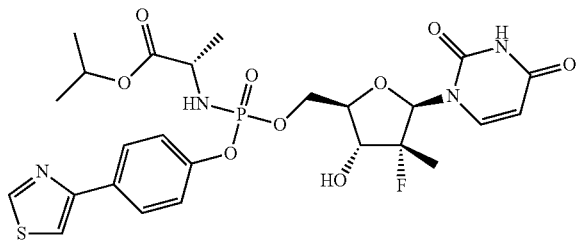 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cscn2)cc1]

Step 1: Preparation of 4-(thiazol-4-yl)phenol

The title compound was prepared according to the method described in Step 1 of Example 37 using p-hydroxyphenylboronic acid, 4-bromothiazole, potassium carbonate and bis(triphenylphosphine)palladium dichloride as starting materials.
$^1$HNMR (300 MHz, CDCL3-$d_6$) δppm: 8.65 (s, 1H), 7.83 (s, 12H), 7.39 (s, 1H), 6.90 (d, 2H), 5.00 (S, 1H).

Step 2: Preparation of (2S)-2-(((4-(thiazol-4-yl)phenyloxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-(thiazol-4-yl)phenol prepared from Step 1, phosphorus oxychloride, L-alanine isopropyl ester hydrochloride, pentafluorophenol and (2'R)-2'-deoxy-2'-fluoro-2'-methyluridine as starting materials.
$^1$HNMR (500 MHz, DMSO) δ: 11.48 (s, 1H), 9.18 (s, 1H), 8.12 (s, 1H), 8.00 (d, 2H), 7.58 (s, 1H), 7.31 (d, 2H), 6.08-6.04 (m, 2H), 5.82 (d, 1H), 5.57 (m, 1H), 4.87-4.85 (m, 1H), 4.38-4.37 (m, 1H), 4.27 (m, 1H), 4.02 (m, 1H), 3.84-3.82 (m, 2H), 1.28-1.24 (m, 6H), 1.16-1.14 (m, 6H).
ESI-MS m/z: [M+H]$^+$=613.

Example 39: (2S)-2-(((((4'-chloro-2'-fluoro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

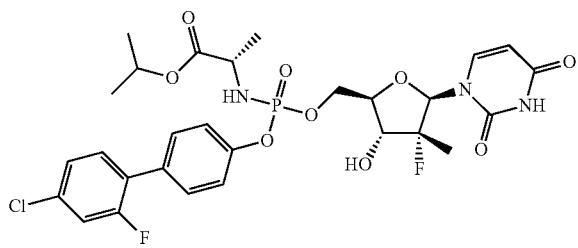 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc(Cl)cc2F)cc1]

Step 1: Preparation of 4-hydroxy-4'-chloro-2'-fluoro-[1,1'-biphenyl]

The title compound was prepared according to the method described in Step 1 of Example 37 using 2-fluoro-4-chloroiodobenzene, p-hydroxyphenylboronic acid, potassium carbonate and PdCl$_2$(PPh$_3$)$_2$ as starting materials.
$^1$HNMR (300 MHz, CDCL3-$d_6$) δppm: 7.43-6.83 (m, 7H), 4.94 (s, 1H).

Step 2: Preparation of (2S)-2-(((((4'-chloro-2'-fluoro-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-hydroxy-4'-chloro-2'-fluoro-[1,1'-biphenyl]prepared from Step 1, phosphorus oxychloride, L-alanine isopropyl ester hydrochloride, pentafluorophenol and (2'R)-2'-deoxy-2'-fluoro-2'-methyluridine as starting materials.
$^1$HNMR (500 MHz, DMSO) δ: 11.48 (s, 1H), 7.56-7.52 (m, 5H), 7.39-7.30 (m, 3H), 6.11-6.01 (m, 2H), 5.86-5.82 (m, 1H), 5.56-5.54 (m, 1H), 4.87-4.85 (m, 1H), 4.42-4.39 (m, 1H), 4.28-4.26 (m, 1H), 4.04-4.02 (m, 1H) 3.85-3.84 (m, 2H), 1.28-1.24 (m, 6H), 1.16-1.14 (m, 6H).
ESI-MS m/z: [M+Na]+=680.

Example 40: (2S)-2-(((((3'-fluoro-4'-methyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

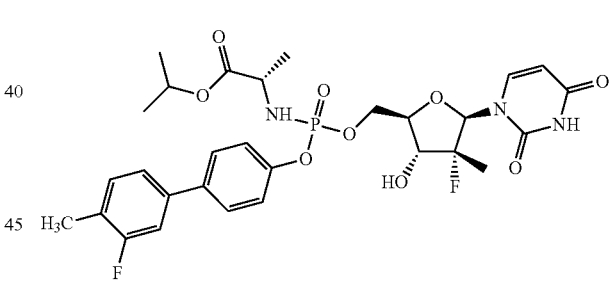

Step 1: Preparation of 4-hydroxy-3'-fluoro-4'-methyl-[1,1'-biphenyl]

The title compound was prepared according to the method described in Step 1 of Example 37 using 3-fluoro-4-methyl-iodobenzene, p-hydroxyphenylboronic acid, potassium carbonate and PdCl$_2$(PPh$_3$)$_2$ as starting materials.
$^1$HNMR (300 MHz, CDCL3-$d_6$) δppm: 7.45-6.87 (m, 7H), 4.77 (s, 1H), 2.31 (s, 3H).

Step 2: Preparation of (2S)-2-(((((3'-fluoro-4'-methyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-hydroxy-3'-fluoro-4'- methyl-[1,1'-biphenyl]prepared from Step 1, phosphorus oxychloride, L-alanine isopropyl ester hydrochloride, pentafluorophenol and (2'R)-2'-deoxy-2'-fluoro-2'-methyluridine as starting materials.

¹HNMR (500 MHz, DMSO) δ: 11.48 (s, 1H), 7.68 (d, 2H), 7.57 (d, 1H), 7.44-7.29 (m, 5H) 6.08-6.03 (m, 2H), 5.85-5.82 (m, 1H), 5.56-5.54 (m, 1H), 4.88-4.83 (m, 1H), 4.42-4.38 (m, 1H), 4.28-4.26 (m, 1H), 4.04-4.02 (m, 1H), 3.84-3.82 (m, 2H), 2.26 (d, 3H), 1.28-1.23 (m, 6H), 1.19-1.14 (m, 6H).

ESI-MS m/z: [M+Na]+=660.

Example 41: (2S)-2-(((((4'-fluoro-3'-methyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

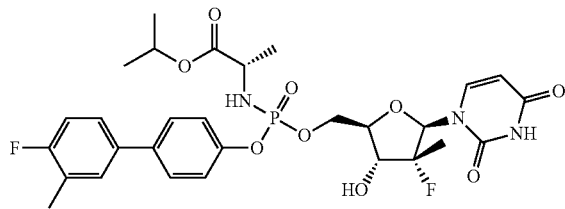 [SMILES: Cc1cc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)ccc1F]

Step 1: Preparation of 4-hydroxy-4'-fluoro-3'-methyl-[1,1'-biphenyl]

The title compound was prepared according to the method described in Step 1 of Example 37 using 4-fluoro-3-methyl-iodobenzene, p-hydroxyphenylboronic acid, potassium carbonate and PdCl₂(PPh₃)₂ as starting materials.

¹H NMR (300 MHz, CDCL3-d₆) δ ppm: 7.52-7.42 (m, 2H), 7.34-7.26 (m, 2H), 7.06-6.87 (m, 3H), 4.67 (s, 1H), 2.32 (s, 3H).

Step 2: Preparation of (2S)-2-(((((4'-fluoro-3'-methyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester The title compound was prepared according to the method described in Example 1 using 4-hydroxy-4'-fluoro-3'-methyl-[1,1'-biphenyl]prepared from Step 1, phosphorus oxychloride, L-alanine isopropyl ester hydrochloride, pentafluorophenol and (2'R)-2'-deoxy-2'-fluoro-2'-methyluridine as starting materials.

¹HNMR (500 MHz, DMSO) δ: 11.50 (s, 1H), 7.65-7.55 (m, 4H), 7.47-7.45 (m, 1H), 7.30-7.17 (m, 3H), 6.11-5.99 (m, 2H), 5.85-5.83 (m, 1H), 5.57-5.54 (m, 1H), 4.90-4.84 (m, 1H), 4.38-4.36 (m, 1H), 4.27-4.25 (m, 1H), 4.02-3.99 (m, 1H), 3.87-3.80 (m, 2H), 2.30 (s, 3H), 1.29-1.21 (m, 6H), 1.16-1.14 (m, 6H).

ESI-MS m/z: [M+Na]+=660.

Example 42: (2S)-2-(((((4'-methyl-[1,1'-biphenyl]-4-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino) propanoic Acid Isopropyl Ester

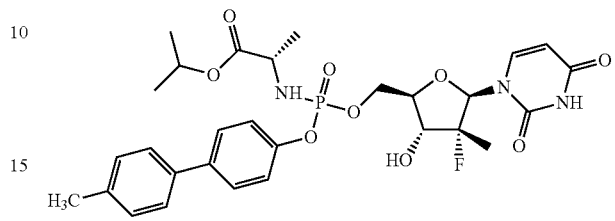

The title compound was prepared according to the method described in Example 1 using 4-hydroxy-4'-methyl-[1,1'-biphenyl], phosphorus oxychloride, L-alanine isopropyl ester hydrochloride, pentafluorophenol and (2'R)-2'-deoxy-2'-fluoro-2'-methyluridine as starting materials.

¹HNMR (500 MHz, DMSO) δ: 11.49 (s, 1H), 7.58 (d, 1H), 7.53-7.51 (m, 4H), 7.29-7.25 (m, 4H), 6.10-6.02 (m, 2H), 5.88-5.82 (m, 1H), 5.60-5.55 (m, 1H), 4.88-4.84 (m, 1H), 4.41-4.38 (m, 1H), 4.27 (m, 1H), 4.04-4.02 (m, 1H) 3.84-3.82 (m, 2H), 2.33 (s, 3H), 1.28-1.23 (m, 6H), 1.18-1.14 (m, 6H).

ESI-MS m/z: [M+H]⁺=620.

Example 43: (2S)-2-(((R)-((4-fluoro-1,2-dimethyl-1H-indol-5-yl)oxy)(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)phosphoryl)amino)propanoic Acid Isopropyl Ester

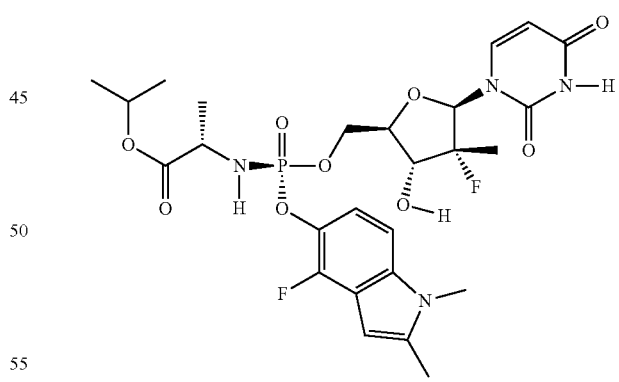

The title compound was prepared according to the similar method as described in Example 33.

¹HNMR (400 MHz, DMSO-d₆) δ: 11.49 (s, 1H), 7.55-7.57 (d, 1H). 7.07-7.19 (m, 2H), 6.27 (s, 1H), 5.91-6.11 (m, 3H), 5.14-5.56 (d, 1H), 4.82-4.88 (t, 1H), 4.41-4.45 (m, 1H), 4.24-4.28 (m, 1H), 4.04-4.06 (m, 1H), 3.74-3.82 (m, 2H), 3.647 (s, 3H), 2.39 (s, 3H), 1.20-1.25 (m, 6H), 1.14-1.16 (m, 6H).

LC-MS m/z: [M+H]⁺=615.

Pharmacological and Pharmacokinetic Activity

Experimental Example 1: Antiviral Activity Assay of the Compounds of the Present Invention in HCV Replicon System 1. Experimental Materials
1.1 Reagents:

TABLE 1

List of reagents

| Name of reagents | Supplier |
|---|---|
| DMEM medium | Invitrogen |
| Fetal bovine serum (FBS) | Gibco |
| L-Glutamine | Invitrogen |
| penicillin-streptomycin solution | Invitrogen |
| DPBS/Modified | Hyclone |
| Trypsin/EDTA | Invitrogen |
| Dimethyl sulfoxide (DMSO) | Sigma |
| Bright-Glo ™ | Promega |
| CellTiter-Fluor ™ Reagent | Promega |

1.2 Huh7 1b Cell Lines:

The cell line Huh7 1b, which was provided by WuXi AppTec Co., Ltd. in Shanghai, contained an HCV 1b replicon with a stable Luciferase (Luc) reporter. It was constructed by cloning HCV nonstructural protein gene, neo (G418 resistance) and luciferase reporter gene into the pBR vector through gene recombination technology. Then the vector carrying the HCV replicon was transfected into Huh7 cells, and the transfected Huh7 cells were screened by G418 resistance. The HCV replicon was stably replicated, and the related protein and luciferase were stably expressed in Huh7 cells. The cells model was used for in-vitro screen of anti-HCV compounds. The anti-HCV activity of the compounds was measured by detecting the level of luciferase expression. See Lohmann V, et al. 1999. Replication of subgenomic hepatitis C virus RNAs in a hepatoma cell line. Science. 285(5424):110-113.

1.3 Positive Control:

The control drug used in this experimental example was the compound of Example 25 in WO 2008/121634 (PCT/US2008/058183), i.e. (S)-2-{[(2R,3R,4R,5R)-5-(2,4-dioxo-3,4-dihydro-2H-pyrimidin-1-yl)-4-fluoro-3-hydr oxy-4-methyl-tetrahydro-furan-2-ylmethoxy]-phenoxy-phosphorylamino}-propanoic acid isopropyl ester. This compound was prepared according to the method described in J. Org. chem, 2011, 76, 8311-8319, and identified by H-NMR and mass spectrometry.

2. Experimental Procedures:
2.1 compound preparation: adding each of the compounds listed in Table 2 to 96-well plates using a POD™ 810 Automation Platform (LabCyte Corporation, USA), with 10 μM of each of the compounds as a starting concentration and in duplicate; serially diluting each of the compounds in 3-fold fashion and formulating 10 concentrations, with the final concentration of DMSO being 0.5%;
2.2 cells preparation: seeding the Huh71b cells into 96-well plates respectively with a volume of 125 μl and $8 \times 10^3$ cells/well, and incubating in a 37° C., 5% $CO_2$ incubator for 72 h;
2.3 detection of cell activity: adding 30 μl per cell of the CellTiter-Fluor™ Reagent, incubating in a 37° C., 5% $CO_2$ incubator for 1 h, measuring the fluorescence signal values with a fluorometer, and using the obtained data for calculation of cytotoxicities of the compounds;
2.4 Bright-Glo detection: adding 100 μl per well of the Bright-Glo™ Luciferase Substrate, using a chemiluminescence detection system EnVision™ (PerkinElmer, USA) to detect the fluorescence signal values within 5 minutes, and using the obtained data for calculation of potencies of the compounds.
2.5 data processing: converting the obtained data to a percentage of cell viability (Viability %) using the following formula:

$$\text{Viability \%} = \frac{CPD}{ZPE} \times 100$$

CPD: fluorescence signal value of the well added with the compound
ZPE (Zero percent effect): fluorescence signal value of the control well with zero percent effect.
Processing the raw data to calculate a percentage of inhibition (Inhibition %) using the following formula:

$$\text{Inhibition \%} = \frac{CPD - HPE}{ZPE - HPE} \times 100$$

CPD: fluorescence signal value of the well added with the compound;
HPE (Hundred percent effect): fluorescence signal value of the control well with hundred percent effect;
ZPE (Zero percent effect): fluorescence signal value of the control well with zero percent effect.

The inhibition percentage was processed by the GraphPad Prism software to obtain the corresponding curves and $EC_{50}$ values. The data was listed in Table 2.

TABLE 2

| Example Number | Structure | $EC_{50}$ (μM) |
|---|---|---|
| Positive control | 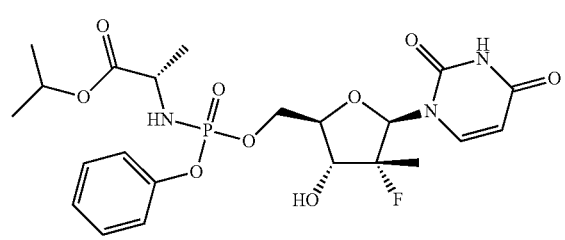 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1] | 0.1168 |

TABLE 2-continued

| Example Number | Structure | EC$_{50}$ (μM) |
|---|---|---|
| Example 1 | 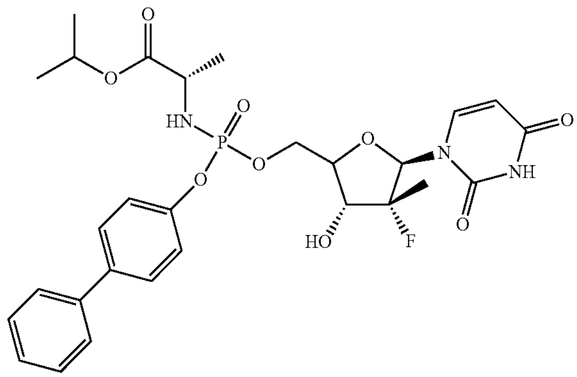 [SMILES: CC(C)OC(=O)[C@H](C)NP(=O)(OCC1O[C@@H](n2ccc(=O)[nH]c2=O)[C@](C)(F)[C@@H]1O)Oc1ccc(-c2ccccc2)cc1] | 0.056 |
| Example 2 | 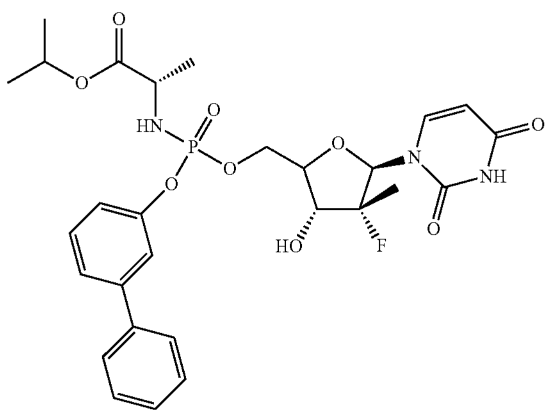 [SMILES: CC(C)OC(=O)[C@H](C)NP(=O)(OCC1O[C@@H](n2ccc(=O)[nH]c2=O)[C@](C)(F)[C@@H]1O)Oc1cccc(-c2ccccc2)c1] | 0.1051 |
| Example 3 | 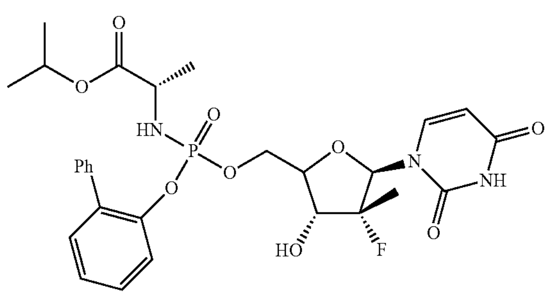 [SMILES: CC(C)OC(=O)[C@H](C)NP(=O)(OCC1O[C@@H](n2ccc(=O)[nH]c2=O)[C@](C)(F)[C@@H]1O)Oc1ccccc1-c1ccccc1] | 0.1232 |
| Example 4 | 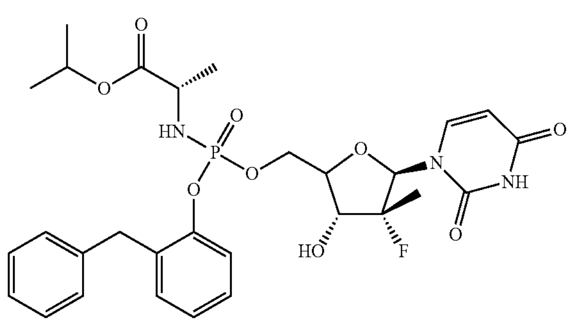 [SMILES: CC(C)OC(=O)[C@H](C)NP(=O)(OCC1O[C@@H](n2ccc(=O)[nH]c2=O)[C@](C)(F)[C@@H]1O)Oc1ccccc1Cc1ccccc1] | undetected |

TABLE 2-continued

| Example Number | Structure | EC$_{50}$ (μM) |
|---|---|---|
| Example 5 | 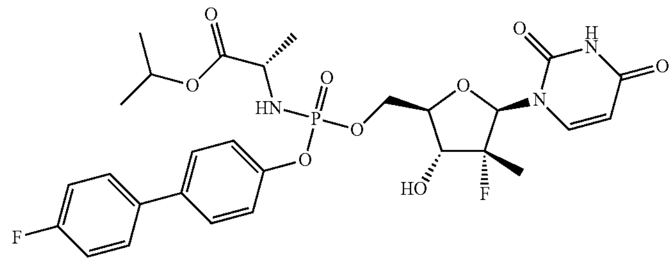 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc(F)cc2)cc1] | 0.061 |
| Example 6 | 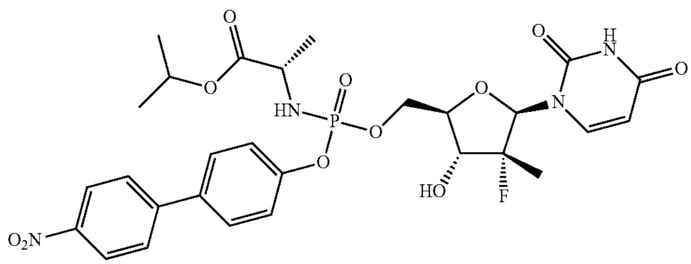 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc([N+](=O)[O-])cc2)cc1] | undetected |
| Example 7 | 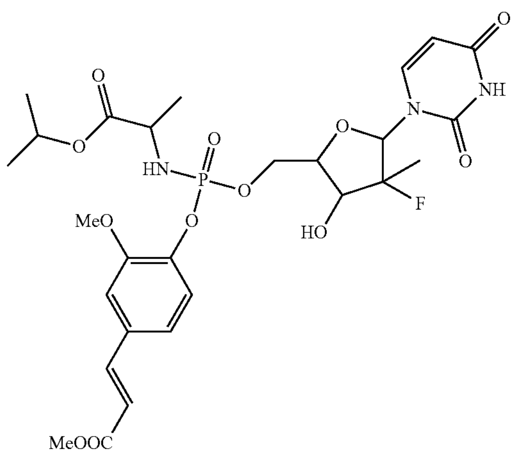 [SMILES: COC(=O)/C=C/c1ccc(OP(=O)(NC(C)C(=O)OC(C)C)OCC2OC(n3ccc(=O)[nH]c3=O)C(C)(F)C2O)c(OC)c1] | undetected |
| Example 8 | 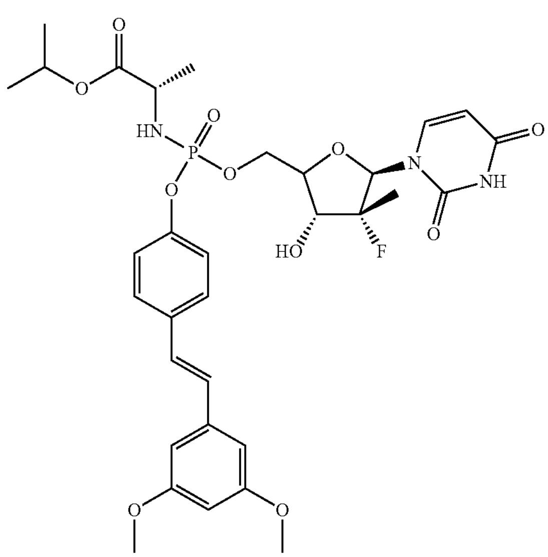 [SMILES: COc1cc(/C=C/c2ccc(OP(=O)(N[C@@H](C)C(=O)OC(C)C)OCC3O[C@@H](n4ccc(=O)[nH]c4=O)[C@](C)(F)[C@@H]3O)cc2)cc(OC)c1] | 0.411 |

TABLE 2-continued

| Example Number | Structure | EC$_{50}$ (μM) |
| --- | --- | --- |
| Example 9 | 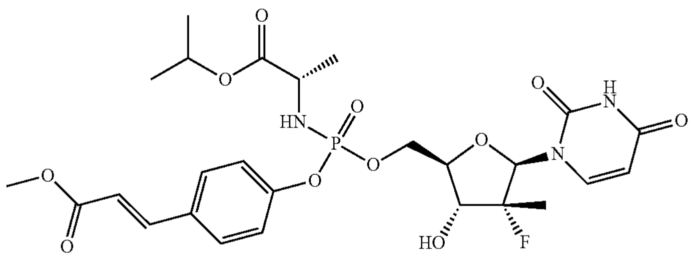 [SMILES: COC(=O)/C=C/c1ccc(OP(=O)(N[C@@H](C)C(=O)OC(C)C)OC[C@H]2O[C@@H](n3ccc(=O)[nH]c3=O)[C@](C)(F)[C@@H]2O)cc1] | undetected |
| Example 10 | 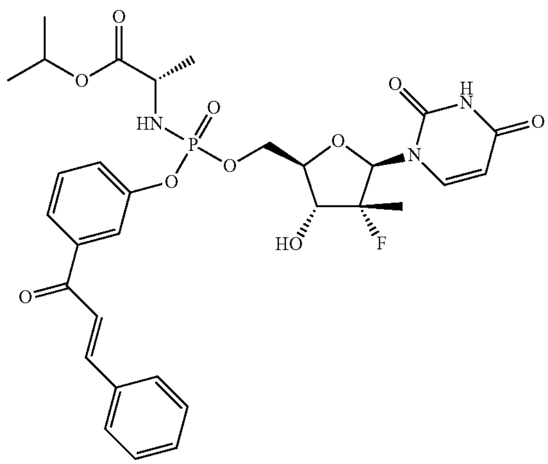 [SMILES: CC(C)OC(=O)[C@H](C)NP(=O)(OC[C@H]1O[C@@H](n2ccc(=O)[nH]c2=O)[C@](C)(F)[C@@H]1O)Oc1cccc(C(=O)/C=C/c2ccccc2)c1] | undetected |
| Example 11 | 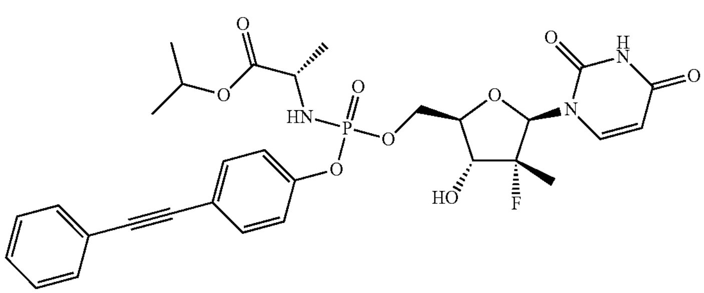 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(C#Cc2ccccc2)cc1] | 0.189 |
| Example 12 | 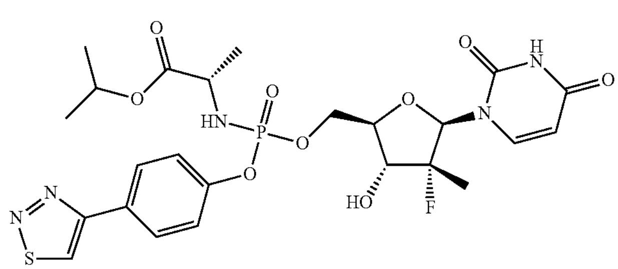 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2csnn2)cc1] | 0.637 |

TABLE 2-continued

| Example Number | Structure | EC$_{50}$ (µM) |
| --- | --- | --- |
| Example 13 | 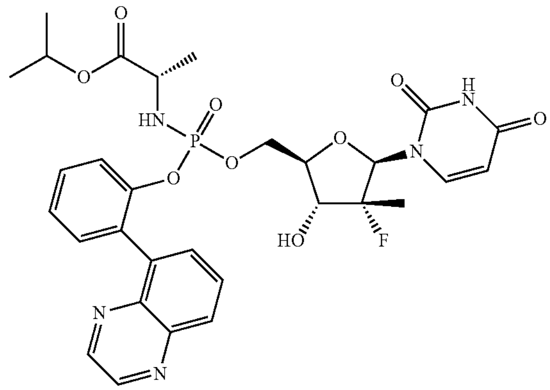 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1-c1cccc2nccnc12] | undetected |
| Example 14 | 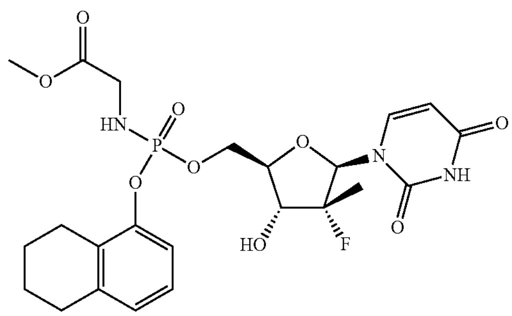 [SMILES: COC(=O)CNP(=O)(OC[C@H]1O[C@@H](n2ccc(=O)[nH]c2=O)[C@](C)(F)[C@@H]1O)Oc1cccc2c1CCCC2] | 0.2231 |
| Example 15 | 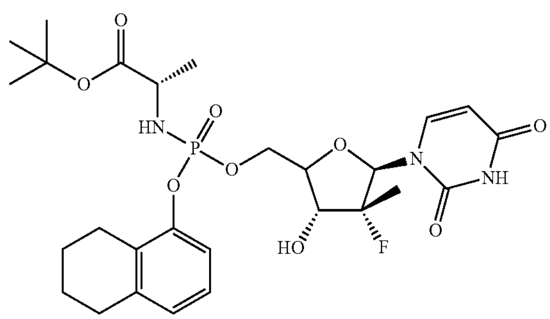 [SMILES: C[C@H](NP(=O)(OCC1O[C@@H](n2ccc(=O)[nH]c2=O)[C@](C)(F)[C@@H]1O)Oc1cccc2c1CCCC2)C(=O)OC(C)(C)C] | >3.33 |
| Example 16 | 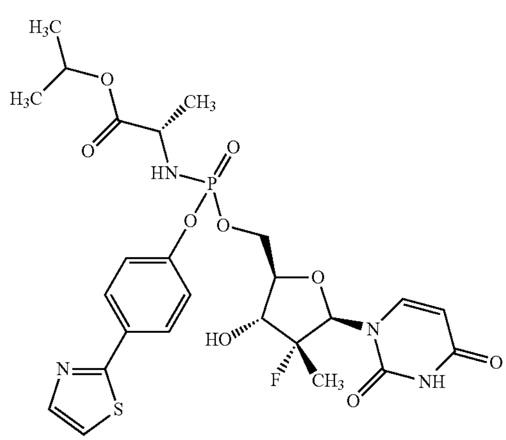 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cncs2)cc1] | 3.871 |

TABLE 2-continued
| Example Number | Structure | EC$_{50}$ (μM) |
|---|---|---|
| Example 17 | 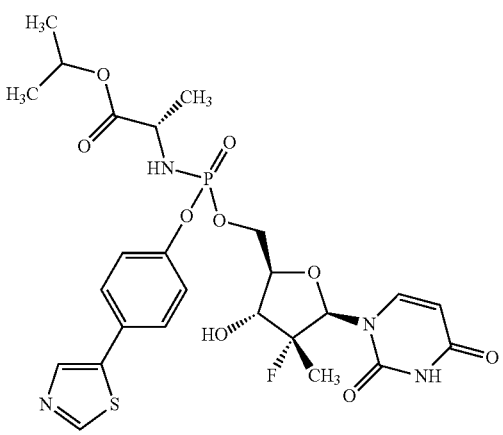 | 0.2577 |
| Example 18 | 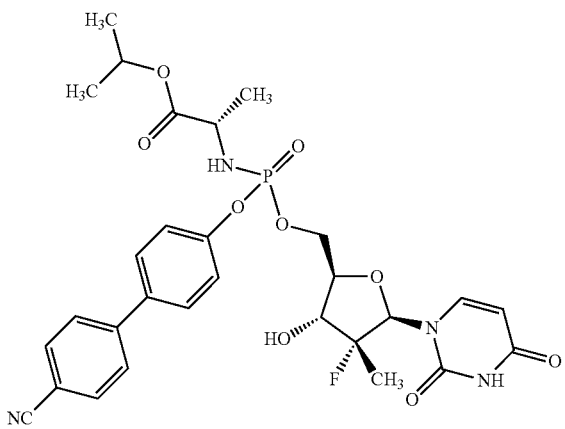 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc(C#N)cc2)cc1] | 0.3141 |
| Example 19 | 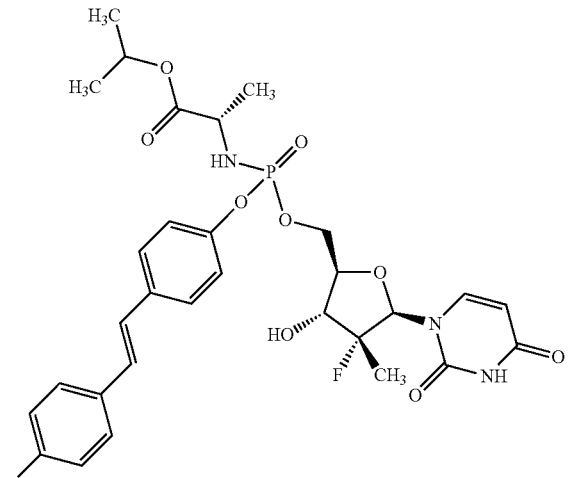 | 0.303 |

TABLE 2-continued
| Example Number | Structure | EC$_{50}$ (μM) |
|---|---|---|
| Example 20 | 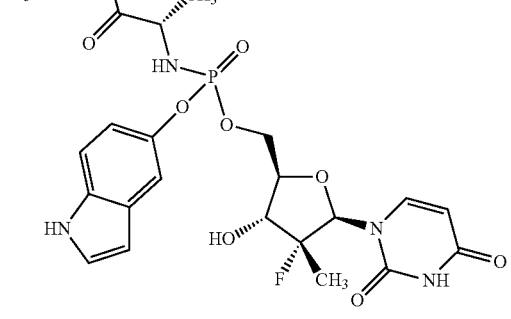 | 3.871 |
| Example 21 | 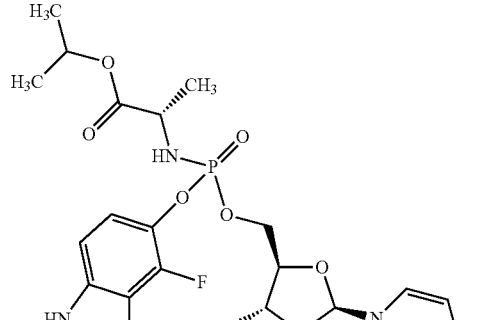 | 0.2577 |
| Example 22 | 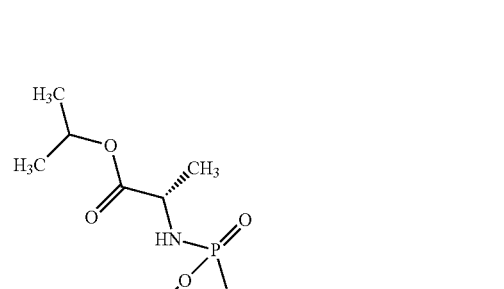 | 0.3141 |

TABLE 2-continued
| Example Number | Structure | EC$_{50}$ (μM) |
|---|---|---|
| Example 23 | 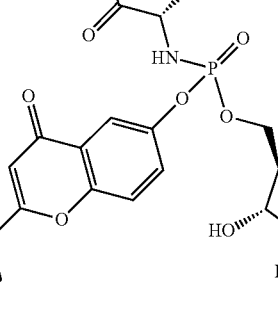 | 4.488 |
| Example 24 | 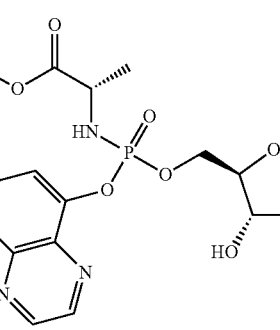 | undetected |
| Example 25 | 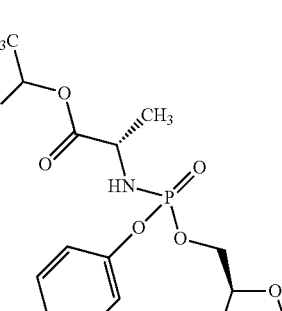 | undetected |
| Example 27 | 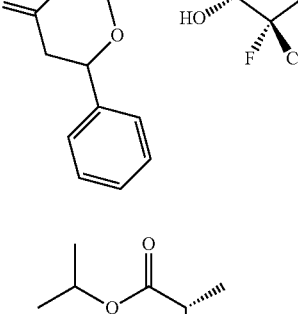 | 0.098 |

TABLE 2-continued

| Example Number | Structure | EC$_{50}$ (μM) |
|---|---|---|
| Example 28 | 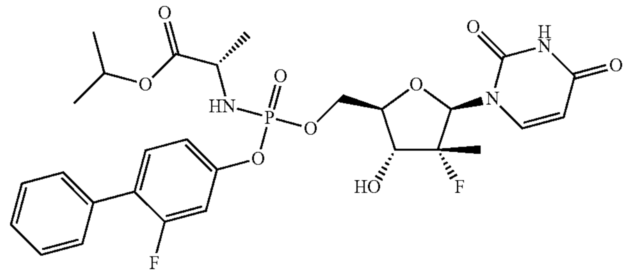 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccccc2)c(F)c1] | 0.123 |
| Example 31 | 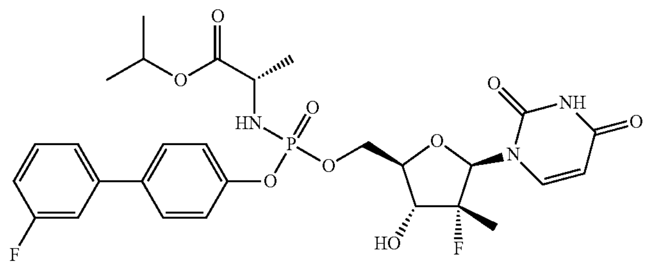 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cccc(F)c2)cc1] | 0.102 |
| Example 32 | 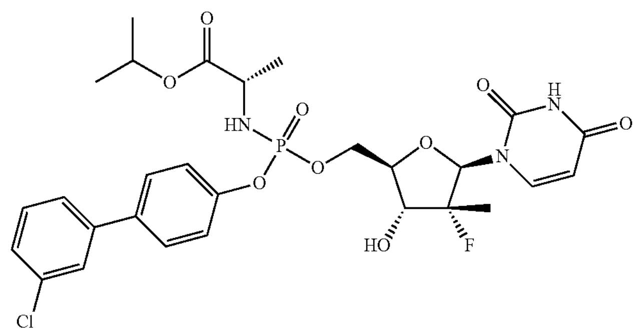 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cccc(Cl)c2)cc1] | 0.068 |
| Example 33 | 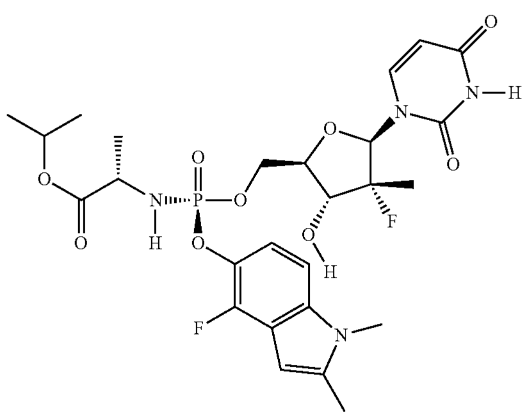 [SMILES: Cc1cc2c(F)c(O[P@](=O)(N[C@@H](C)C(=O)OC(C)C)OC[C@H]3O[C@@H](n4ccc(=O)[nH]c4=O)[C@](C)(F)[C@@H]3O)ccc2n1C] | 0.033 |
| Example 36 | 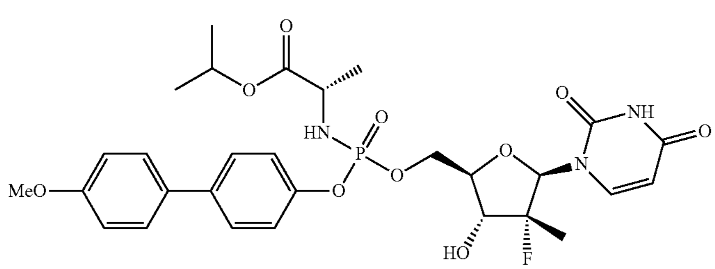 [SMILES: COc1ccc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)cc1] | 0.073 |

TABLE 2-continued
| Example Number | Structure | EC$_{50}$ (μM) |
|---|---|---|
| Example 38 | 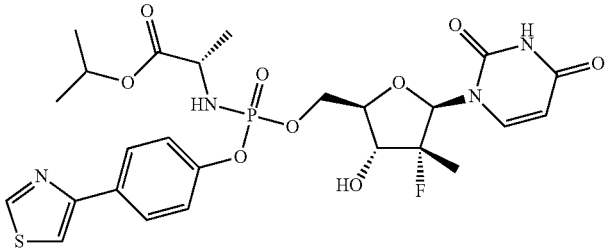 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2cscn2)cc1] | 0.100 |
| Example 39 | 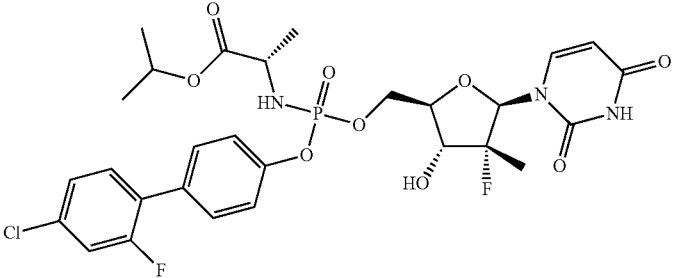 [SMILES: CC(C)OC(=O)[C@H](C)NP(=O)(OC[C@H]1O[C@@H](n2ccc(=O)[nH]c2=O)[C@](C)(F)[C@@H]1O)Oc1ccc(-c2ccc(Cl)cc2F)cc1] | 0.061 |
| Example 40 | 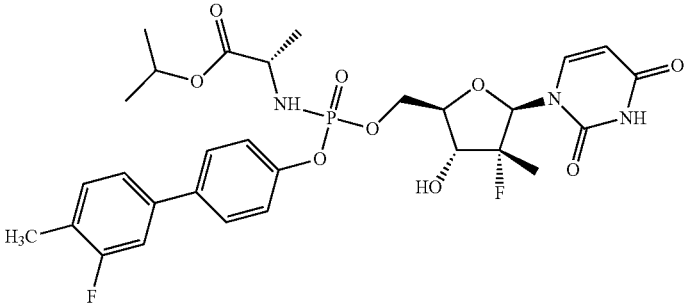 [SMILES: Cc1ccc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)cc1F] | 0.056 |
| Example 41 | 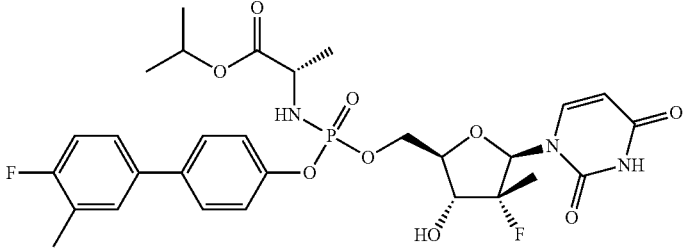 [SMILES: Cc1cc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)ccc1F] | 0.050 |
| Example 42 | 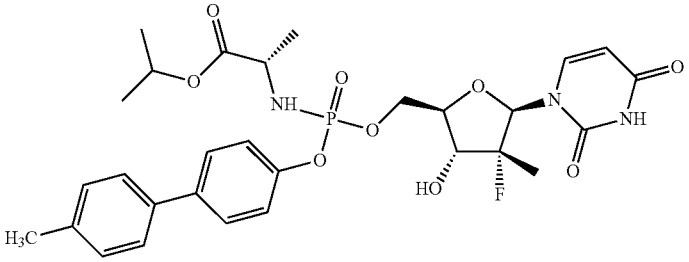 [SMILES: Cc1ccc(-c2ccc(OP(=O)(N[C@@H](C)C(=O)OC(C)C)OC[C@H]3O[C@@H](n4ccc(=O)[nH]c4=O)[C@](C)(F)[C@@H]3O)cc2)cc1] | 0.126 |

TABLE 2-continued

| Example Number | Structure | EC$_{50}$ (μM) |
|---|---|---|
| Example 43 | 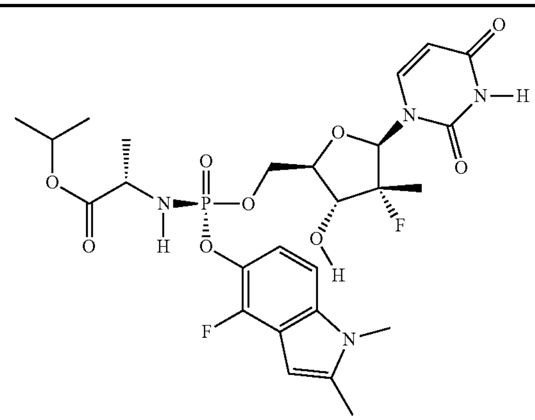 | 0.069 |

The above results have shown that the compounds of the present invention have the ability to inhibit HCV virus very efficiently, and compared to the positive control, have a superior or equal activity based on EC$_{50}$ values.

Experimental Example 2: Antiviral Activity Assay of the Compounds of the Present Invention in the Cell-Culture-Derived Infectious HCV (HCVcc) System 1. Experimental Materials
1.1 Compounds The compound according to the above example 1 was used in this experiment. The compound was formulated into a 10 mM mother liquid with DMSO, diluted to 500 nM by DMEM complete culture medium containing 0.5% of DMSO, followed by 4-fold dilution successively, and six concentrations were obtained. The positive control was diluted to 10 μM by DMEM complete culture medium containing 0.5% of DMSO, followed by 4-fold successively, and six concentrations were obtained.

1.2 Cells

Huh 7.5.1 cells, provided by Shanghai Institute of Materia Medica, Chinese Academy of Sciences.

1.3 Viruses

J399EM (HCV genotype 2a) virus, i.e. a full length HCV mutant strain transfected with EGFP (enhanced green fluorescent protein) was used, which had the same infection capacity as the wild type JFH-1. The NS5A-EGFP fusion protein fluorescence was observed directly in infected cells by inserting EGFP coding sequence in the NS5A region. J399EM was provided by Shanghai Institute of Materia Medica, Chinese Academy of Sciences.

1.4 Reagents

DMEM medium, purchased from Invitrogen Corporation, USA;
Fetal bovine serum (FBS), purchased from Sigma Corporation, USA;
L(+)-Glutamine, purchased from Invitrogen Corporation, USA;
Penicillin-streptomycin (Pen-Strep), purchased from Invitrogen Corporation, USA;
Phosphate buffered saline (PBS), purchased from Hyclone Corporation, USA;
Trypsin, purchased from Invitrogen Corporation, USA;
Dimethyl sulfoxide (DMSO), purchased from Sigma Corporation, USA;
Lysis buffer, purchased from Promega Corporation, USA;
MTT, purchased from Sigma Corporation, USA.

1.4 Instruments

EnVision® MultilabelPlate readers, purchased from Perkin-Elmer Corporation, USA.

2 Experimental Procedures

1) Huh 7.5.1 cells preparation: collecting the Huh7.5.1 cells in logarithmic phase, resuspending in DMEM complete culture medium, seeding into 96-well plates (7×10$^3$ cells/well), and incubating in a 37° C., 5% CO$_2$ incubator for 24 h;
2) virus infection: resuspending J399EM viruses in DMEM complete culture medium, adding the virus supernatant (MOI≈0.1) to the above 96-well plates, and washing with PBS after 8 hours of infection;
3) drug treatment: adding various concentrations of the compounds to the Huh7.5.1 cells infected by J399EM viruses, with each concentration in duplicate; setting the control group with zero percent effect (ZPE) and the control group with hundred percent effect (HPE); replacing the compound with the DMEM complete culture medium containing 0.5% DMSO in ZPE group, and using the cells not infected with viruses in HPE group.
4) cells incubation: incubating the 96-well plates in a 37° C., 5% CO$_2$ incubator for 72 hr;
5) anti-HCV activity detection: reading the relative fluorescence units (RFU) of each well by EnVision® Multi label Plate readers after incubation, and calculating the anti-HCV activity of the compounds using the obtained data according to the following formula:

$$\text{Inhibition \%} = (\text{RFU}_{ZPE} - \text{RFU}_{CPD})/(\text{RFU}_{ZPE} - \text{RFU}_{HPE}) \times 100$$

wherein RFU$_{ZPE}$ represents the relative fluorescence units of the control group with zero percent effect and RFU$_{CPD}$ represents the relative fluorescence units of the corresponding compound group, and RFU$_{HPE}$ represents the relative fluorescence units of the control group with hundred percent effect.

6) Cell viability detection: adding MTT solution to each well, incubating in a 37° C., 5% CO$_2$ incubator for 4 hr, followed by addition of MTT dissolving solution, reading optical density (OD) of each well at 570 nm by the Multi label Plate readers after 6 hr, calculating the cytotoxicity of the compounds using the obtained data according to the following formula:

$$\text{Viability \%} = OD_{CPD}/OD_{ZPE} \times 100$$

wherein $OD_{ZPE}$ represents the optical density of the control group with zero percent effect, and $OD_{CPD}$ represents the optical density of the corresponding compound;

7) Data processing: processing the Inhibition %, Viability % by GraphPad Prism Software respectively, and obtaining the half maximal effective concentration ($EC_{50}$) values and half maximal cytotoxic concentration ($CC_{50}$) values of the compounds against the HVCcc GT2a viruses. The results were listed in Table 3.

TABLE 3

| Example Number | Structure | $EC_{50}$ (µM) | $CC_{50}$ (µM) |
|---|---|---|---|
| Positive control | 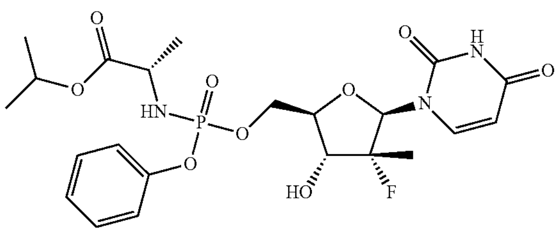 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1] | 0.173 | >10 |
| Example 1 | 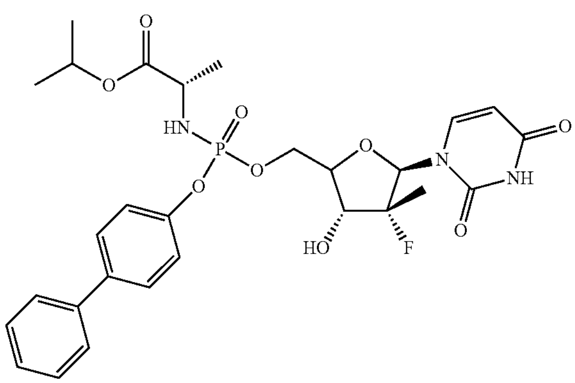 [SMILES: CC(C)OC(=O)[C@H](C)NP(=O)(OCC1O[C@@H](n2ccc(=O)[nH]c2=O)[C@](C)(F)[C@@H]1O)Oc1ccc(-c2ccccc2)cc1] | 0.039 | >10 |

It was seen from Table 3 that the compound of Example 1 of the present invention had excellent antiviral activity and less cell toxicity compared with the positive control in the HCVcc system.

In addition, the experiments of the present invention also showed that using in vitro HCVcc system, the compounds prepared by the present invention, such as the compounds prepared in Examples 2, 5, 12, 16, 18, 28 and 38, had a low half maximal effective concentration ($EC_{50}$) and a high half maximal cytotoxic concentration ($CC_{50}$) against the HCVcc GT2a viruses, which demonstrated good inhibitory activity and small cytotoxicity.

Experimental Example 3: Pharmacokinetic Studies of the Compounds of the Present Invention in SD Rats 1. Experimental Materials
1.1 Compounds
In this experiment, the compound of Example 1 was used, and the positive control drug was the same as above. Each of the compounds was added to 0.5% sodium carboxymethyl cellulose (CMC), and the mixture was vortexed to prepare a 10 mg/mL suspension for intragastric administration.

The standard substance GS-461203 was the metabolite of the tested compounds, and the chemical name was (2'R)-2'-deoxy-2'-fluoro-2'-methyluridinetriphosphate, which was purchased from TriLink BioTechnologies Corporation, USA.

1.2 Animals
Male SD rats, 6-8 weeks old, weighing 237.0-268.4 g, provided by Shanghai Super-B&K laboratory animal Co. Limited.

1.3 Reagents
methanol (chromatographic pure), purchased from Spectrum Corporation, USA;
acetonitrile (chromatographic pure): purchased from Spectrum Corporation, USA.

1.4 Instruments
API 5500 LC-MS, purchased from AB Corporation, USA.

2. Experimental method
1) administration: dividing SD rats into 4 groups, with 18 rats in each group, intragastrically administering with the compound in an amount of 50 mg/kg. Fasting the rats for 10-15 hours prior to intragastric administration, and refeeding four hours after administration;
2) sampling: at 0.5 h, 1 h, 2 h, 4 h, 6 h and 12 h after administration, sacrificing the rats (n=3 at each time point for each group), collecting about 1 g of each rat liver respectively, adding 3 volumes of pre-cooled methanol, homogenizing for 30 s and storing the prepared liver homogenate in −80° C. before analysis.
3) standard curve preparation: taking appropriate amount of GS-461203 stock solution, serially diluting with methanol to prepare standard solutions with concentrations of 30, 27, 10, 5, 2, 1, 0.5, 0.2 and 0.1 μg/mL, parallelly adding 10 μL of each standard solution to 90 μL blank rat liver homogenate to prepare sample standard curves of concentrations of 3000, 2700, 1000, 500, 200, 100, 50, 20 and 10 ng/mL.

4) sample processing: adding 30 μl liver homogenate sample or standard curve sample to 150 μl solution of acetonitrile containing the internal standard (100 ng/mL), vortexing for 2 min, centrifuging for 10 min (6000 revolutions/min), and transferring the supernatant to injection vials;

5) sample data analysis: taking 5 μL supernatant, injecting, and then using UPLC-MS/MS to detect the concentration of GS-461203 in the samples; according to the obtained drug concentration-time data of the liver homogenates, using the non-compartmental model of pharmacokinetic calculation software WinNonlin 6.2.1 to calculate pharmacokinetic parameters of metabolite GS-461203 of each of the tested compounds. The results were listed in Table 4.

TABLE 4

| | GS-461203 | | |
|---|---|---|---|
| | $C_{max}$ (ng/g liver) | $T_{max}$ (hr) | $AUC_{last}$ (ng/g*hr) |
| Positive control | 753 | 2.00 | 5627 |
| Example 1 | 818 | 1.00 | 7106 |

It was seen from the data in Table 4 that the compound of Example 1 according to the present invention was better than that of the positive control in the peak concentration in liver tissue and the area under the plasma drug concentration-time curve of the metabolite, and had greater in vivo exposure level.

The above results show that the compounds of the present invention have the ability to efficiently inhibit HCV virus, and compared to the positive control, have equal or superior effects in $EC_{50}$, less toxicity to the host cells, higher $CC_{50}$, and good security. The compounds of the present invention have good prospects in the treatment of HCV infection.

Although the present invention has been described in detail above, it should be understood by those skilled in the art that various modifications and alterations can be made without departing from the spirit and scope of the present invention. The scope of the present invention is not limited to the foregoing detailed description and is defined by the claims.

What is claimed is:

1. A nucleoside phosphoramidate compound of the following general formula I,

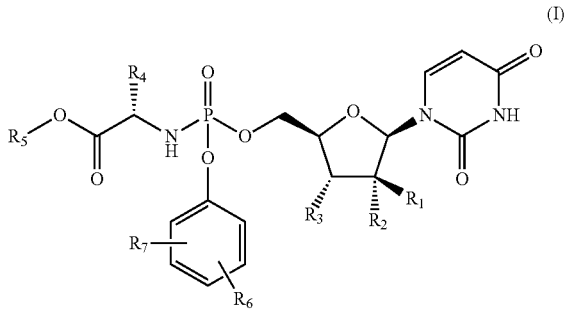

or a salt, or crystal thereof, wherein
(1) $R_1$ is selected from $C_{1-6}$ alkyl;
(2) $R_2$ is selected from halogen;
(3) $R_3$ is selected from OH, H and $C_{1-4}$ alkoxy;
(4) $R_4$ is selected from H, $C_{1-6}$ alkyl and halogenated $C_{1-6}$ alkyl;
(5) $R_5$ is selected from $C_{1-6}$ alkyl and halogenated $C_{1-6}$ alkyl;
(6) $R_6$ is selected from the following moieties:
a) phenyl-Y—, wherein Y is absent or selected from $C_{1-6}$ alkylenyl, $C_{2-6}$ alkenylenyl, $C_{2-6}$ alkynylenyl, $C_{2-6}$ alkenylenyl-(CO)—, $C_{2-6}$ alkynylenyl-(CO)—, O, S, NH— and —N($C_{1-6}$ alkyl), and wherein the phenyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;
b) heterocyclyl-Y—, which is selected from the group consisting of 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, and thieno[3,2-b]thienyl-Y—, wherein Y is absent or selected from $C_{1-6}$ alkylenyl, $C_{2-6}$ alkenylenyl, $C_{2-6}$ alkynylenyl, $C_{2-6}$ alkenylenyl-(CO)—, $C_{2-6}$ alkynylenyl-(CO)—, O, S, —NH— and —N($C_{1-6}$ alkyl) and wherein the heterocyclyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO;
c) $C_{1-6}$ alkyl-O—C(O)—$C_{2-6}$ alkenylenyl- and $C_{1-6}$ alkyl-O—C(O)—$C_{2-6}$ alkenylenyl-C(O)—, wherein the $C_{1-6}$ alkyl is optionally substituted by one or more groups selected from $C_{1-6}$ alkyl, halogen, nitro, $C_{1-6}$ alkoxy, cyano, $C_{2-6}$ alkenyl, $C_{2-6}$ alkynyl, $C_{1-6}$ acylamino, halogenated $C_{1-6}$ alkyl, halogenated $C_{1-6}$ alkoxy, amino, N($C_{1-6}$ alkyl)$_2$ and $C_{1-6}$ alkyl NHCO; and
(7) $R_7$ is selected from H, halogen, $C_{1-6}$ alkyl, halogenated $C_{1-6}$ alkyl, $C_{1-6}$ alkoxy, halogenated $C_{1-6}$ alkoxy, NO$_2$, CN, $C_{1-6}$ alkyl-NH—CO—, hydroxy, mono-$C_{1-6}$ alkylamino, di-$C_{1-6}$ alkylamino, $C_{1-6}$ alkyl-S—, $C_{2-6}$ alkenyl-S—, $C_{2-6}$ alkynyl-S—, $C_{1-6}$ alkyl-SO—, $C_{2-6}$ alkenyl-SO—, $C_{2-6}$ alkynyl-SO—, $C_{1-6}$ alkyl-SO$_2$—, $C_{2-6}$ alkenyl-SO$_2$—, $C_{2-6}$ alkynyl-SO$_2$—, $C_{1-6}$ alkyl-OSO$_2$—, $C_{2-6}$ alkenyl-OSO$_2$—, and $C_{2-6}$ alkenyl-OSO$_2$—; or
(8) $R_6$ and $R_7$ together with the benzene ring to which they are attached form a benzo-annelated five-membered ring or benzo-annelated six-membered ring selected from the group consisting of 1,2,3,4-tetrahydronaphthalene, 2,3-dihydro-1H-indene, indole, benzofuran, quinoxaline, 4H-chromen-4-one, benzo[d]isoxazole, benzo[d]oxazole, benzo[c][1,2,5]thiadiazole, benzo[b]thiophene, and benzodihydropyran-4-one, wherein the benzo-annelated five-membered ring or benzo-annelated six-membered ring is optionally substituted by one or more groups selected from halogen, $C_{1-6}$ alkyl, $C_{1-6}$ alkoxy, halogenated $C_{1-6}$ alkyl, halogenated $C_{1-6}$ alkoxy, phenyl, cyano, $C_{1-6}$ alkyl-OC(O)— and $C_{1-6}$ alkyl-OC(O)—CH$_2$—.

2. The compound according to claim 1, or the salt or crystal thereof, wherein $R_1$ is selected from $C_{1-3}$ alkyl, $R_2$ is F, $R_3$ is selected from OH, H and methoxy, $R_4$ is selected from H and $C_{1-6}$ alkyl, and $R_5$ is selected from $C_{1-6}$ alkyl.

3. The compound according to claim 2, or the salt or crystal thereof, wherein $R_6$ is selected from
   a) phenyl-Y—, wherein Y is absent or selected from $C_{1-4}$ alkylenyl, $C_{2-4}$ alkenylenyl, $C_{2-4}$ alkynylenyl, $C_{2-4}$ alkenylenyl-(CO)—, $C_{2-4}$ alkynylenyl-(CO)—, O, S, —NH— and —N($C_{1-4}$ alkyl), and wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;
   b) heterocyclyl-Y—, which is selected from the group consisting of 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, and thieno[3,2-b]thienyl-Y—, wherein Y is absent or selected from $C_{1-4}$ alkylenyl, $C_{2-4}$ alkenylenyl, $C_{2-4}$ alkynylenyl, $C_{2-4}$ alkenylenyl-(CO)—, $C_{2-4}$ alkynylenyl-(CO)—, O, S, —NH— and —N($C_{1-4}$ alkyl), and wherein the heterocyclyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO; and
   c) $C_{1-4}$ alkyl-O—C(O)—$C_{2-4}$ alkenylenyl- and $C_{1-4}$ alkyl-O—C(O)—$C_{2-4}$ alkenylenyl-C(O)—, wherein the $C_{1-4}$ alkyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO.

4. The compound according to claim 3, or the salt or crystal thereof, wherein $R_6$ is selected from
   a) phenyl, phenyl-$C_{1-3}$ alkylenyl-, phenyl-$C_{2-3}$ alkenylenyl-, phenyl-$C_{2-3}$ alkynylenyl-, phenyl-O—, phenyl-S—, phenyl-NH—, phenyl-N($C_{1-3}$ alkyl)-, phenyl-ethenylenyl-(CO)— and naphthyl-ethenylenyl-(CO)—, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;
   b) 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, thieno[3,2-b]thienyl-Y—, wherein Y is absent or selected from methylenyl, ethylenyl, ethenylenyl, ethynylenyl, ethenylenyl-(CO)—, ethynylenyl-(CO)—, O, S, —NH— and —NCH$_2$—, wherein each of the heterocyclyl groups is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO; and
   c) methyl-OC(O)—=—, ethyl-OC(O)—=—, propyl-OC(O)—=—, isopropyl-OC(O)—=—, butyl-OC(O)—=—, isobutyl-OC(O)—=—, and t-butyl-OC(O)—=—.

5. The compound according to claim 2, or the salt or crystal thereof, wherein $R_6$ group "phenyl-Y—" or "heterocyclyl-Y—" and the oxygen group both of which are attached to the benzene ring are at the para- or meta-position to each other.

6. The compound according to claim 2, or the salt or crystal thereof, wherein $R_1$ is CH$_3$, $R_2$ is F, $R_3$ is OH, $R_4$ is CH$_3$, and $R_5$ is isopropyl.

7. The compound according to claim 1, or the salt or crystal thereof, wherein $R_6$ is selected from
   a) phenyl-Y—, wherein Y is absent or selected from $C_{1-4}$ alkylenyl, $C_{2-4}$ alkenylenyl, $C_{2-4}$ alkynylenyl $C_{2-4}$ alkylenyl-(CO)—, $C_{2-4}$ alkynylenyl-(CO)—, O, S, —NH— and —N($C_{1-4}$ alkyl), and wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;
   b) heterocyclyl-Y—, which is selected from the group consisting of 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazol-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, and thieno[3,2-b]thienyl-Y—, wherein Y is absent or selected from $C_{1-4}$ alkylenyl, $C_{2-4}$ alkenylenyl, $C_{2-4}$ alkynylenyl, $C_{2-4}$ alkenylenyl-(CO)—, $C_{2-4}$ alkynylenyl-(CO)—, O, S, —NH— and —N($C_{1-4}$ alkyl), and wherein the heterocyclyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO; and
   c) $C_{1-4}$ alkyl-O—C(O)—$C_{2-4}$ alkenylenyl- and $C_{1-4}$ alkyl-O—C(O)—$C_{2-4}$ alkenylenyl-C(O)—, wherein the $C_{1-4}$ alkyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, N($C_{1-4}$ alkyl)$_2$ and $C_{1-4}$ alkyl NHCO.

8. The compound according to claim 7, or the salt or crystal thereof, wherein $R_6$ is selected from
   a) phenyl, phenyl-$C_{1-3}$ alkylenyl-, phenyl-$C_{2-3}$ alkenylenyl-, phenyl-$C_{2-3}$ alkynylenyl-, phenyl-O—, phenyl-S—, phenyl-NH—, phenyl-N($C_{1-3}$ alkyl)-, phenylethenylenyl-(CO)— and naphthyl-ethenylenyl-(CO)—, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO, or the phenyl and a group selected from phenyl, oxazolyl, pyrazinyl and pyrrolyl taken together form a naphthyl, benzoxazolyl, benzo[b]pyrazinyl or benzo[b]pyrrolyl;

b) 1H-imidazolyl-Y—, 1,2,4-triazolyl-Y—, 1,2,3-triazolyl-Y—, thiazolyl-Y—, 1,2,3-thiadiazolyl-Y—, 1,2,4-thiadiazolyl-Y—, 1,3,4-thiadiazolyl-Y—, oxazolyl-Y—, 1,2,4-oxadiazolyl-Y—, 1,2,3-oxadiazolyl-Y—, 1,3,4-oxadiazolyl-Y—, pyrimidinyl-Y—, pyrazinyl-Y—, pyridazinyl-Y—, quinoxalinyl-Y—, 4H-chromen-4-one-Y—, pyridyl-Y—, thienyl-Y—, thieno[3,2-b]thienyl-Y—, wherein Y is absent or selected from methylenyl, ethylenyl, ethenylenyl, ethynylenyl, ethenylenyl-(CO)—, ethynylenyl-(CO)—, O, S, —NH— and —NCH$_2$—, wherein each of the heterocyclyl groups is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO; and c) methyl-OC(O)—=—, ethyl-OC(O)—=—, propyl-OC(O)—=—, isopropyl-OC(O)—=—, butyl-OC(O)—=—, isobutyl-OC(O)—=— and t-butyl-OC(O)—=—.

9. The compound according to claim 8, or the salt or crystal thereof, wherein $R_6$ is selected from a) phenyl, phenyl-(CH$_2$)—, phenyl-=-, phenyl-=-C(O)— and phenyl-=-, wherein the phenyl is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO, or the phenyl and a group selected from oxazolyl, pyrazinyl and pyrrolyl taken together form a benzoxazolyl, benzo[b]pyrazinyl or benzo[b]pyrrolyl;

b) 1H-imidazolyl, 1,2,4-triazolyl, 1,2,3-triazolyl, thiazolyl, 1,2,3-thiadiazolyl, 1,2,4-thiadiazolyl, 1,3,4-thiadiazolyl, oxazolyl, 1,2,4-oxadiazolyl, 1,2,3-oxadiazolyl, 1,3,4-oxadiazolyl, pyrimidinyl, pyrazinyl, pyridazinyl, quinoxalinyl, 4H-chromen-4-one, pyridyl, thieno[3,2-b]thienyl, 1H-imidazolyl-(CH$_2$)—, 1,2,4-triazolyl-(CH$_2$)—, 1,2,3-triazolyl-(CH$_2$)—, thiazolyl-(CH$_2$)—, 1,2,3-thiadiazolyl-(CH$_2$)—, 1,2,4-thiadiazolyl-(CH$_2$)—, 1,3,4-thiadiazolyl-(CH$_2$)—, oxazolyl-(CH$_2$)—, 1,2,4-oxadiazolyl-(CH$_2$)—, 1,2,3-oxadiazolyl-(CH$_2$), 1,3,4-oxadiazolyl-(CH$_2$)—, pyrimidinyl-(CH$_2$)—, pyrazinyl-(CH$_2$)—, pyridazinyl-(CH$_2$)—, quinoxalinyl-(CH$_2$)—, 4H-chromen-4-one-(CH$_2$)—, pyridyl-(CH$_2$)—, thieno[3,2-b]thienyl-(CH$_2$)—, 1H-imidazolyl-=-, 1,2,4-triazolyl-=-, 1,2,3-triazolyl-=-, thiazolyl-=-, 1,2,3-thiadiazolyl-=-, 1,2,4-thiadiazolyl-=-, 1,3,4-thiadiazolyl-=-, oxazolyl-=-, 1,2,4-oxadiazolyl-=-, 1,2,3-oxadiazolyl-=-, 1,3,4-oxadiazoly-=-, pyrimidinyl-=-, pyridazinyl-=-, pyridazinyl-=-, quinoxalinyl-=-, 4H-chromen-4-one-=-, pyridyl-=-, thieno[3,2-b]thienyl-=-, 1H-imidazolyl-≡-, 1,2,4-triazolyl-≡-, 1,2,3-triazolyl-≡-, thiazolyl-≡-, 1,2,3-thiadiazolyl-≡-, 1,2,4-thiadiazolyl-≡-, 1,3,4-thiadiazolyl-≡-, oxazolyl-≡-, 1,2,4-oxadiazolyl-≡-, 1,2,3-oxadiazolyl-≡-, 1,3,4-oxadiazolyl-≡-, pyrimidinyl-≡-, pyrazinyl-≡-, pyridazinyl-≡-, quinoxalinyl-≡-, 4H-chromen-4-one-≡-, pyridyl-≡-, or thieno[3,2-b]thienyl-≡-, wherein each of the heterocyclyl groups is optionally substituted by one or more groups selected from $C_{1-4}$ alkyl, halogen, nitro, $C_{1-4}$ alkoxy, cyano, $C_{2-4}$ alkenyl, $C_{2-4}$ alkynyl, $C_{1-4}$ acylamino, halogenated $C_{1-4}$ alkyl, halogenated $C_{1-4}$ alkoxy, amino, $N(C_{1-4}$ alkyl$)_2$ and $C_{1-4}$ alkyl NHCO; and c) methyl-OC(O)—=—.

10. The compound according to claim 7, or the salt or crystal thereof, wherein $R_1$ is $CH_3$, $R_2$ is F, $R_3$ is OH, $R_4$ is $CH_3$, and $R_5$ is isopropyl.

11. The compound according to claim 1, or the salt or crystal thereof, wherein $R_6$ group "phenyl-Y—" or "heterocyclyl-Y—" and the phenolic oxygen group both of which are attached to the benzene ring are at the para- or meta-position to each other.

12. The compound according to claim 1, or the salt or crystal thereof, wherein $R_1$ is $CH_3$, $R_2$ is F, $R_3$ is OH, $R_4$ is $CH_3$, and $R_5$ is isopropyl.

13. The compound according to claim 12, or the salt or crystal thereof, wherein $R_6$ is phenyl or benzyl.

14. The compound according to claim 1, or the salt or crystal thereof, wherein the compound is selected from

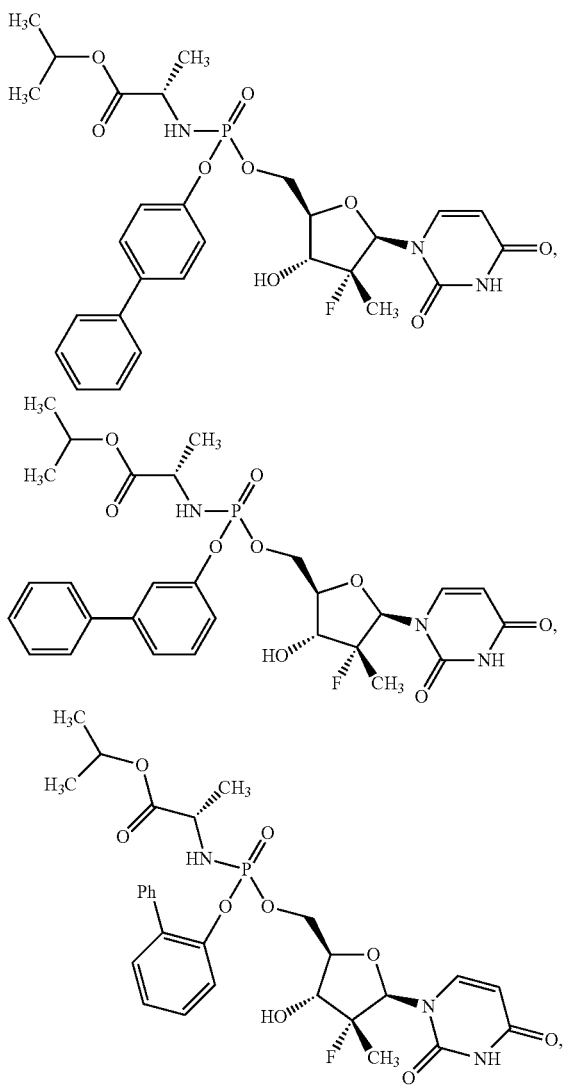

91
-continued
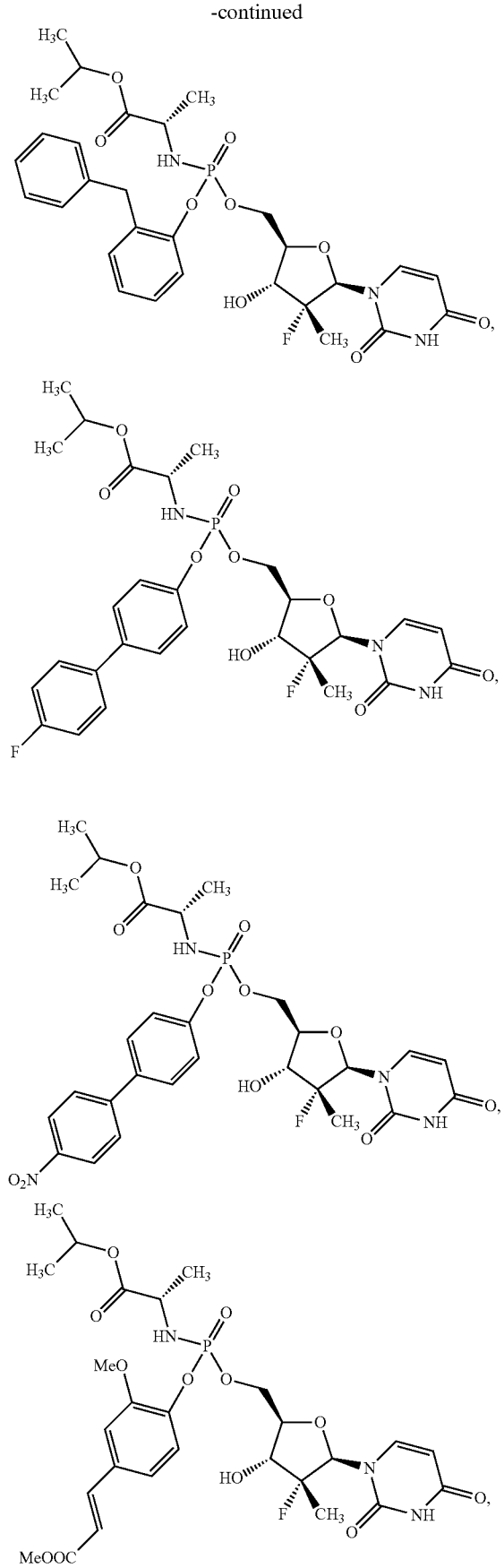
92
-continued
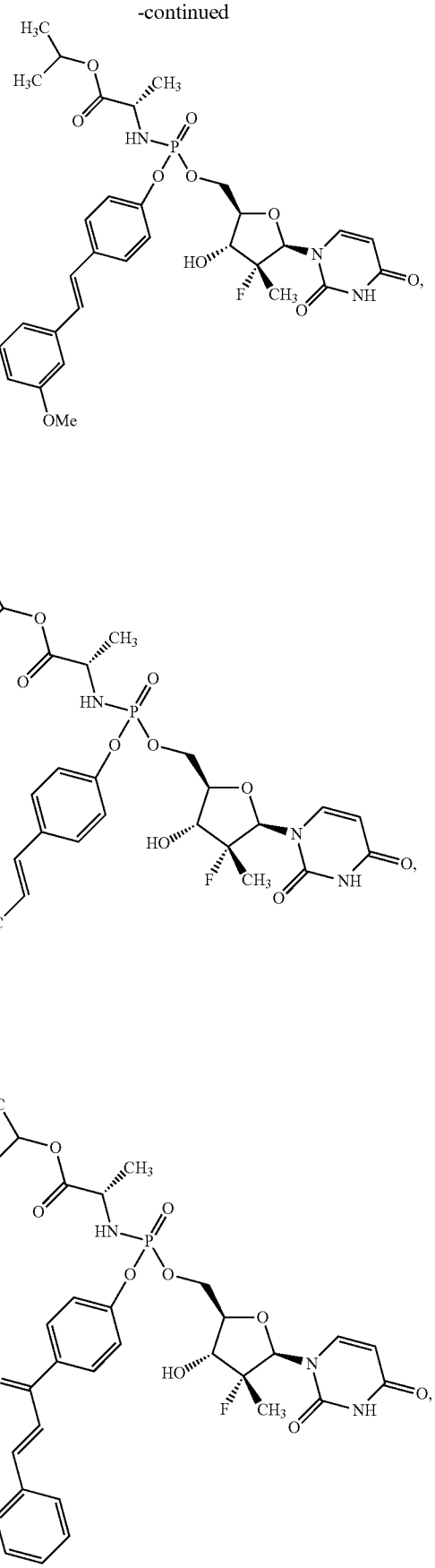

93
-continued
94
-continued
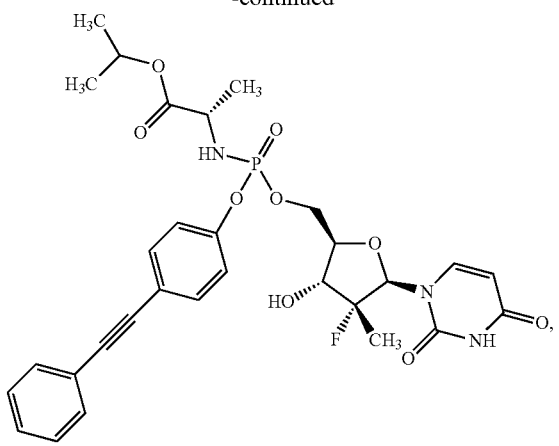
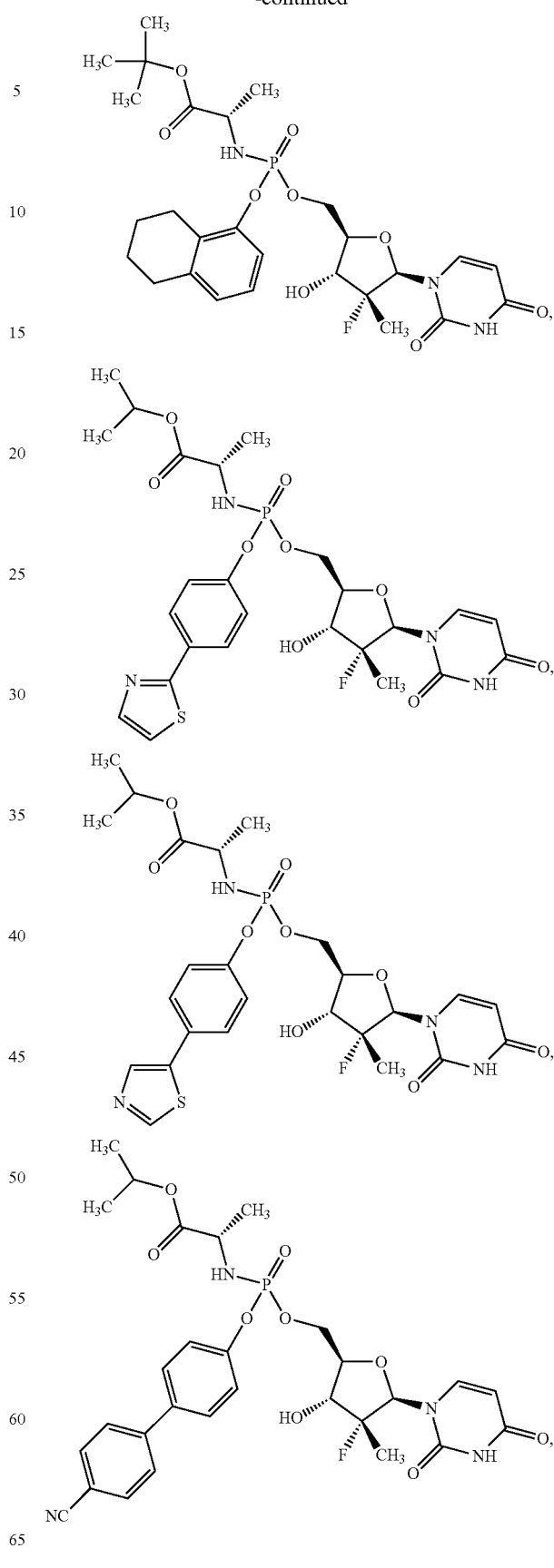

95
-continued
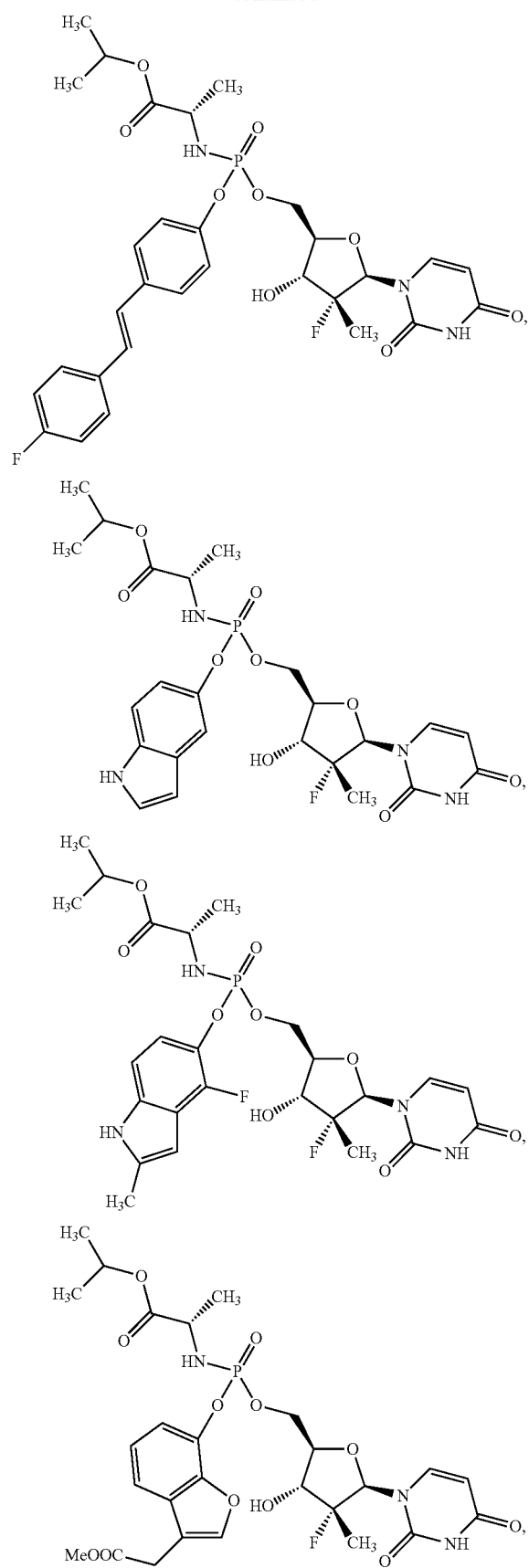
96
-continued
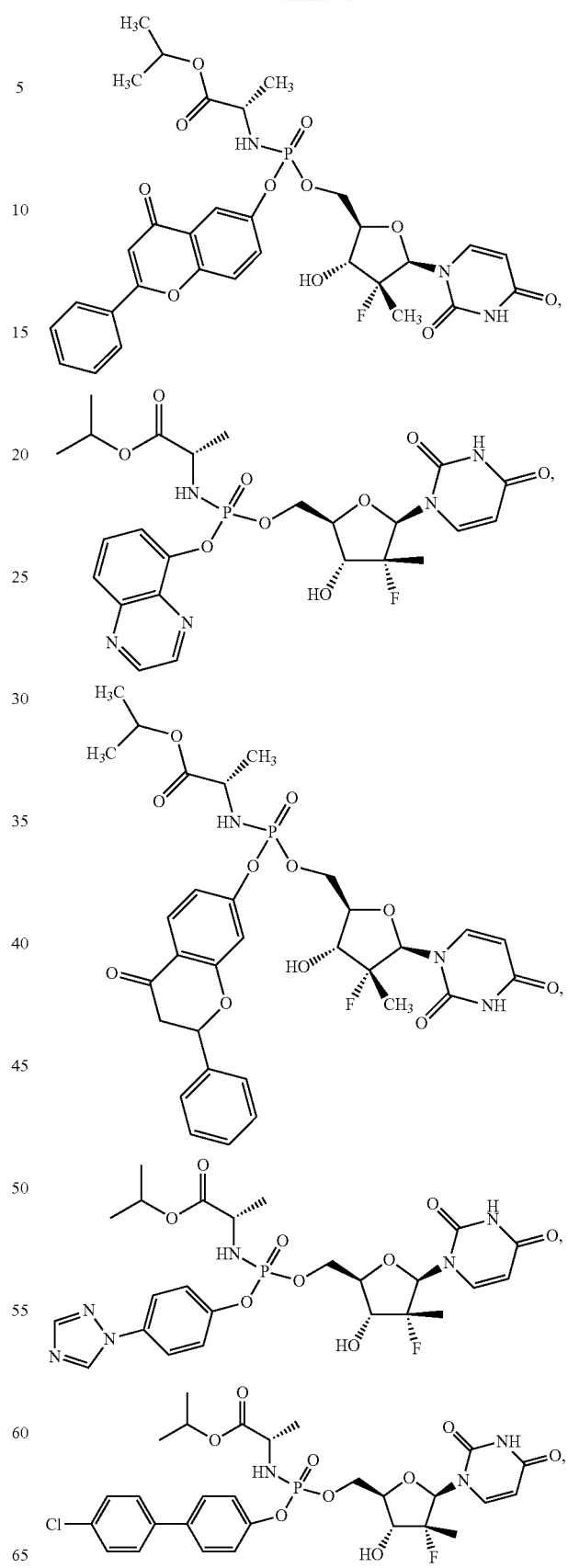

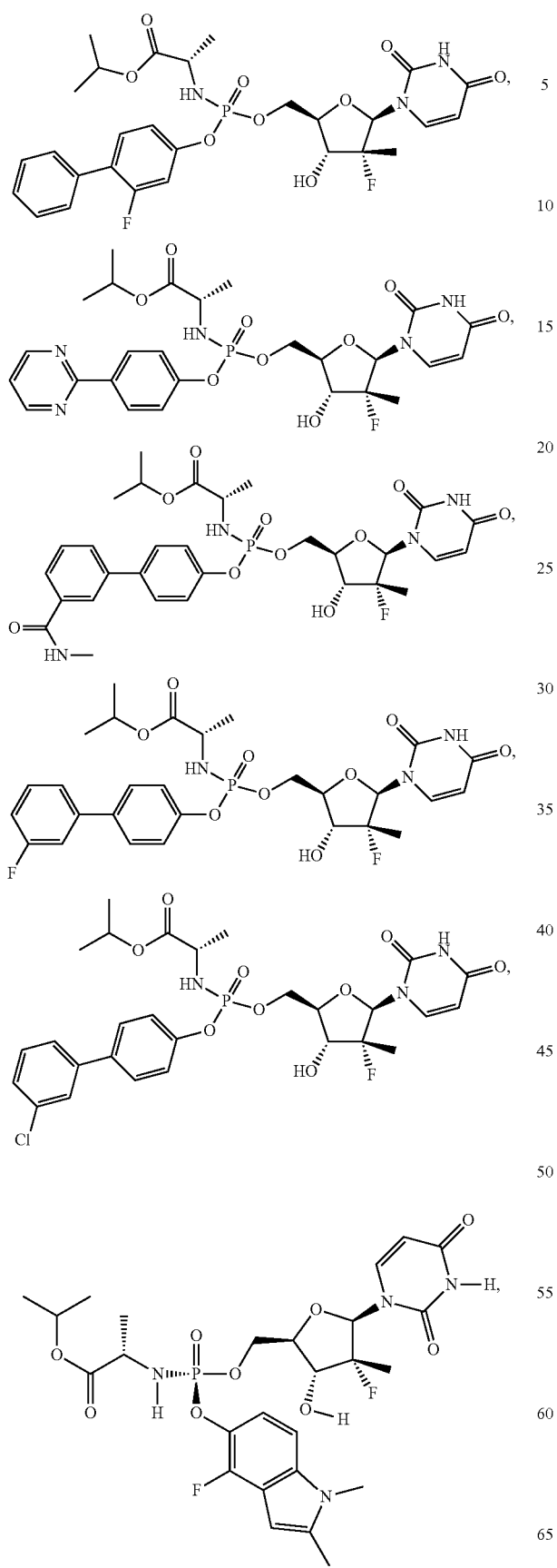

-continued

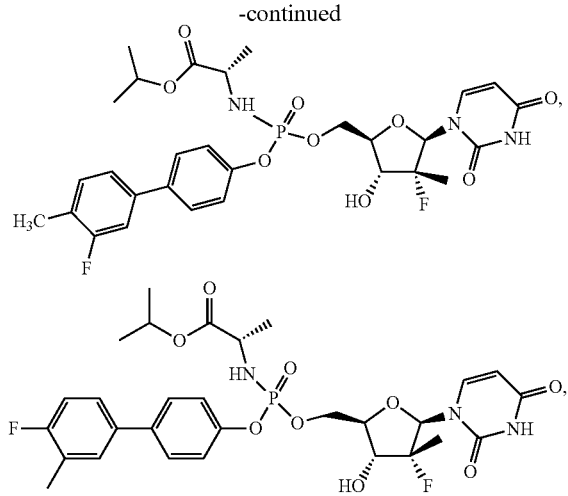

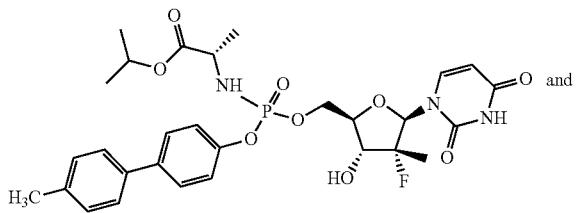

-continued

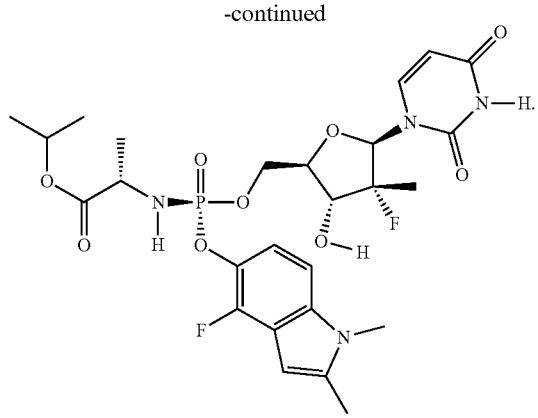

15. A pharmaceutical composition comprising the compound according to claim 14, or the salt or crystal thereof, and a pharmaceutically acceptable carrier.

16. A pharmaceutical composition, comprising the compound according to claim 1, or the salt or crystal thereof and a pharmaceutically acceptable carrier.

17. A method for treatment of hepatitis C viral infection, comprising administering a therapeutically effective amount of the pharmaceutical composition according to claim 16 to a subject in need thereof.

18. A method for treatment of hepatitis C viral infection comprising administering a therapeutically effective amount of the compound according to claim 1, or the salt or crystal thereof to a subject in need thereof.

\* \* \* \* \*